(12) United States Patent
Giovannini et al.

(10) Patent No.: US 8,648,070 B2
(45) Date of Patent: Feb. 11, 2014

(54) BICYCLIC RING SYSTEM SUBSTITUTED SULFONAMIDE FUNCTIONALISED PHENOLS AS MEDICAMENTS

(75) Inventors: Riccardo Giovannini, Verona (IT); Dieter Hamprecht, Pozzolengo (IT); Barbara Kistler, Pfungstadt (DE); Iain Lingard, Monza (IT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/324,248

(22) Filed: Dec. 13, 2011

(65) Prior Publication Data

US 2012/0316159 A1    Dec. 13, 2012

(30) Foreign Application Priority Data

Dec. 17, 2010    (EP) .................................. 10 195 642

(51) Int. Cl.
*A61K 31/535* (2006.01)
*C07D 265/36* (2006.01)
*C07D 241/36* (2006.01)
*C07D 265/00* (2006.01)
*C07D 498/02* (2006.01)
*C07D 221/00* (2006.01)

(52) U.S. Cl.
USPC ..................... 514/230.5; 514/278; 514/235.8; 514/249; 544/105; 544/349; 544/71; 546/16

(58) Field of Classification Search
USPC ............ 514/230.5, 235.8, 249, 278; 544/105, 544/349, 71; 546/16
See application file for complete search history.

(56) References Cited

U.S. PATENT DOCUMENTS

2004/0097547 A1    5/2004    Taveras et al.

FOREIGN PATENT DOCUMENTS

| WO | 02057230 A1 | 7/2002 |
| WO | WO 02/057230 A1 * | 7/2002 |
| WO | 2008148790 A1 | 12/2008 |
| WO | WO 2008/148790 A1 * | 12/2008 |
| WO | 2010015613 A1 | 2/2010 |
| WO | WO 2010/015613 A1 * | 2/2010 |
| WO | 2010063802 A1 | 6/2010 |
| WO | WO 2010/063802 A1 * | 6/2010 |

OTHER PUBLICATIONS

International Search Report and Written Opinion for PCT/EP2011/073026 mailed Mar. 16, 2012.
International Search Report and Written Opinion for PCT/EP2011/073025 mailed Mar. 14, 2012.

\* cited by examiner

*Primary Examiner* — Blessing M Fubara
(74) *Attorney, Agent, or Firm* — Michael P. Morris; Edward S. Lazer

(57) ABSTRACT

This invention relates to bicyclic ring system substituted sulfonamide functionalized phenols of general formula 1,

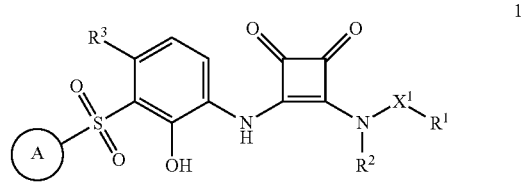

their use as inhibitors of CXCR2 activity, pharmaceutical compositions containing the same, and methods of using the same as agents for treatment and/or prevention of respiratory or gastrointestinal complaints or diseases, inflammatory diseases of the joints, skin, or eyes, diseases of the peripheral or central nervous system or cancers, as well as pharmaceutical compositions which contain these compounds.

6 Claims, No Drawings

BICYCLIC RING SYSTEM SUBSTITUTED SULFONAMIDE FUNCTIONALISED PHENOLS AS MEDICAMENTS

FIELD OF THE INVENTION

This invention relates to bicyclic ring system substituted sulfonamide functionalized phenols and their use as inhibitors of CXCR2 activity, pharmaceutical compositions containing the same, and methods of using the same as agents for treatment and/or prevention of respiratory diseases or gastrointestinal complaints or diseases, inflammatory diseases of the joints, skin, or eyes, diseases of the peripheral or central nervous system or cancers, as well as pharmaceutical compositions which contain these compounds.

BACKGROUND INFORMATION

WO2010/063802 discloses acyclic and monocyclic sulfonamide functionalized phenolic squarates for use as CXCR2 receptor antagonists WO02/057230 discloses acyclic and monocyclic sulfonamide functionalized phenolic squarates for use as interleukin-8 receptor antagonists US2007/067088 discloses bicyclic sulfonamide functionalized phenolic ureas for use as interleukin-8 receptor antagonists

BRIEF SUMMARY OF THE INVENTION

Cellular movement and placement represents a fundamental property of cells of the immune system. It enables their mobilization and expansion to sites of pathogen challenge. Cell movement is also essential for the complex T cell, B cell and dendritic cell interactions to orchestrate the immune response. For cell migration chemoattractants that signal through seven-transmembrane-G-protein-coupled receptors are of central importance.

The most important facilitators of leukocyte migration are chemoattractant cytokines (chemokines) that bind a large subfamily of the G protein-coupled receptors.

Virtually all cell types, including T and B lymphocytes, natural killer (NK) cells, neutrophils, eosinophils, basophils, dendritic cells (DC) and nonleukocytic cells, such as endothelial cells, fibroblasts, smooth muscle cells, are able to respond to chemotactic stimuli.

Chemokines have been classified into 4 subfamilies based on the presence of cysteines at the N-terminal part of the protein. CXC, CC, CX3C and C. CXC chemokines can be further subclassified into Glutamin-Leucin-Arginine containing (ELR+) and ELR− chemokines (not containing this tripeptide motif). All members of the ELR+ family of chemokines (CXCL1-3 and CXCL5-8) bind to and activate the CXC chemokines receptor 2 (CXCR2), two members (CXCL6 and 8) additionally bind and activate CXCR1. CXCR2 is expressed in the myeloid compartment (e.g. neutrophils, monocytes). It has attracted particular attention, as it has been shown to play a crucial role in the development and promotion of numerous inflammatory diseases and tumor progression. In many animal models, functional blockade of CXCR2 has been shown to dampen inflammatory processes.

In vitro assays of chemotaxis in general reflect in vivo inflammatory responses and are therefore regarded as correlates of cellular immunity. Therefore it would be desirable to design CXCR2 antagonists that are particularly efficacious in CXCR2 dependent chemotaxis.

The present invention describes low molecular weight bicyclic ring system substituted sulfonamide functionalized phenols with CXCR2 antagonist activity. It has been surprisingly found that the compounds of the present invention have a superior efficacy in inhibition of CXCR2 dependent chemotaxis. In addition, compounds of the present invention have been found to have satisfactory pharmacokinetic properties.

DETAILED DESCRIPTION OF THE INVENTION

A compound of formula 1,

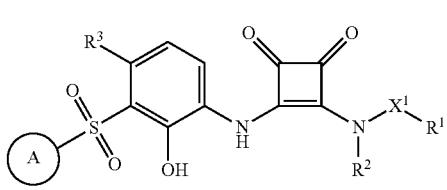

wherein
$R^1$ is an 5-10 membered aromatic, heteroaromatic, non aromatic cyclic or heterocyclic, single or condensed multiring system, optionally substituted by 1-4 residues selected from halogen or $C_{1-6}$-alkyl, optionally substituted with one or more F atoms;
$X^1$ is absent or methylene optionally substituted with $C_{1-5}$-alkyl, said alkyl optionally substituted with one or more F atoms, $C_{1-4}$-alkyl-O—, CN or $C_{3-8}$-cycloalkyl, wherein optionally one carbon atom is replaced by an O;
$R^2$ is H;
$R^3$ is H, halogen, CN, $C_{1-6}$-alkyl, optionally substituted with one or more F atoms; preferably $R^3$ is H or Cl;
A is a N-linked 7-13 membered non-aromatic bicyclic system in which the two rings are either condensed to each other or joined in a spiro system and in which if present one CH group can be optionally replaced by N and one, two three or four $CH_2$ groups in said system are optionally replaced by NH, CO, O, S, SO, $SO_2$, and one, two three or four positions on said ring system are optionally substituted with one or more F atoms, $C_{1-6}$-alkyl, optionally substituted with one or more F atoms, $C_{1-6}$-alkyl-OC(O)—, HO—$C_{1-6}$-alkyl or $C_{1-6}$-alkyl-O—$C_{1-6}$-alkyl- and in which optionally two of these substituents are joined to form an additional ring
or a pharmaceutically acceptable salt thereof.

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like OH, $NH_2$, SO, $SO_2$, CN (cyano), COOH, $CF_3$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$- alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk is may be used in sub-formulas to indicate the bond which is connected to the core molecule as defined.

For example, the term "3-carboxypropyl-group" represents the following substituent:

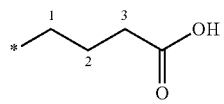

wherein the carboxy group is attached to the third carbon atom of the propyl group. The terms "1-methylpropyl-", "2,2-dimethylpropyl-" or "cyclopropylmethyl-" group represent the following groups:

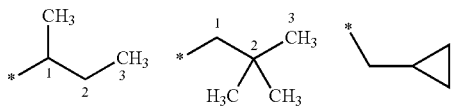

The asterisk may be used in sub-formulas to indicate the bond which is connected to the core molecule as defined.

Many of the followings terms may be used repeatedly in the definition of a formula or group and in each case have one of the meanings given above, independently of one another.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine(2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine(2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

The term halogen generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "carbocyclyl" as used either alone or in combination with another radical, means a mono- bi- or tricyclic ring structure consisting of 3 to 14 carbon atoms. The term "carbocycle" refers to fully saturated and aromatic ring systems and partially saturated ring systems. The term "carbocycle" encompasses fused, bridged and spirocyclic systems.

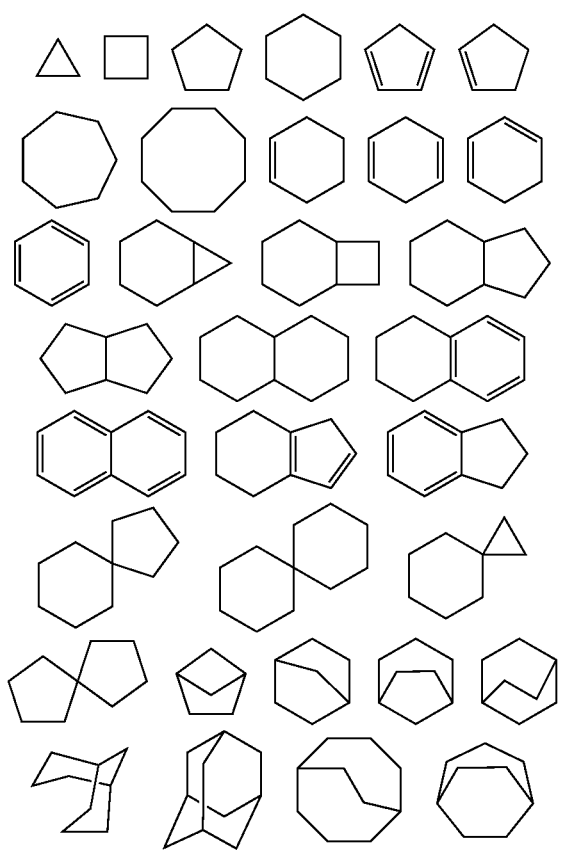

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" means a saturated or unsaturated mono- or polycyclic-ring systems including aromatic ring system containing one or more heteroatoms selected from N, O or $S(O)_r$, wherein r=0, 1 or 2, consisting of 3 to 14 ring atoms wherein none of the heteroatoms is part of the aromatic ring. The term "heterocycle" is intended to include all the possible isomeric forms.

Thus, the term "heterocyclyl" includes the following exemplary structures which are not depicted as radicals as each form may be attached through a covalent bond to any atom so long as appropriate valences are maintained:

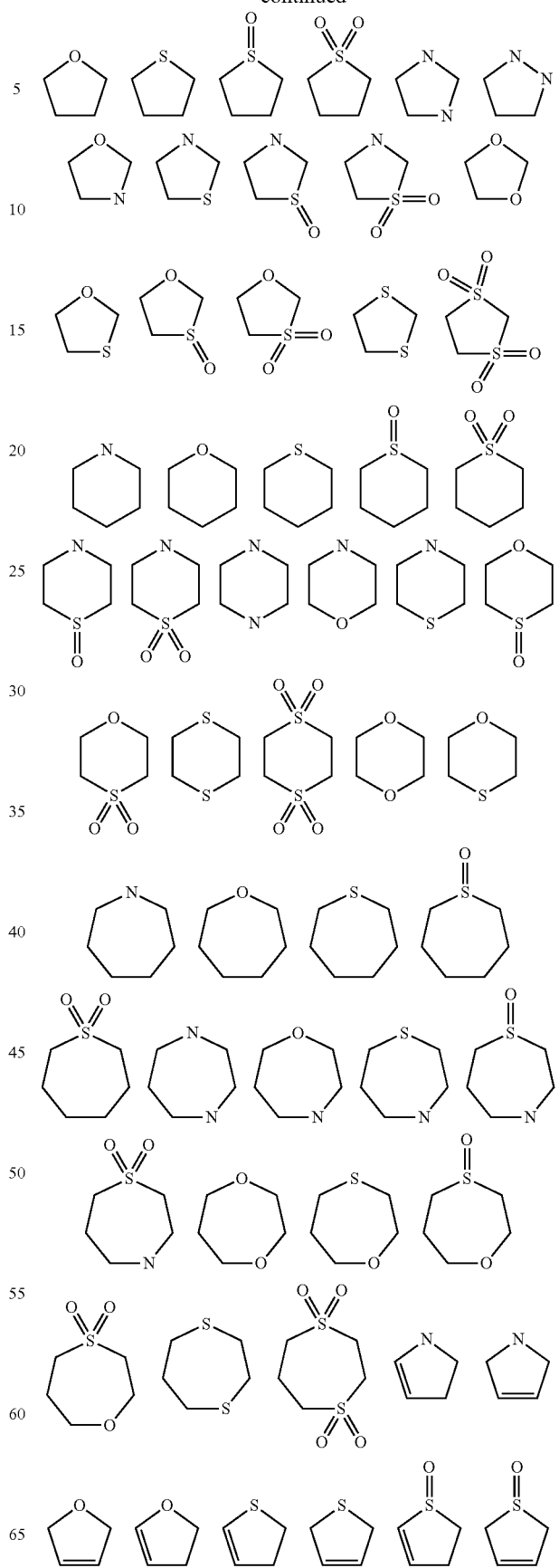

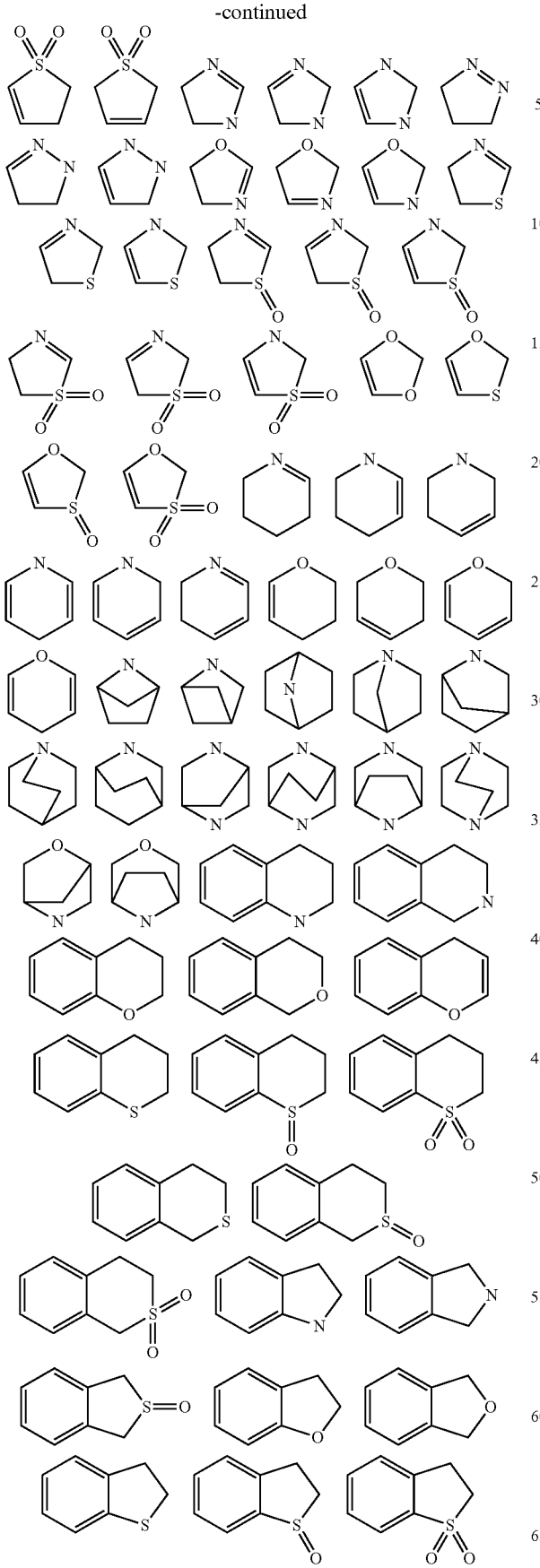
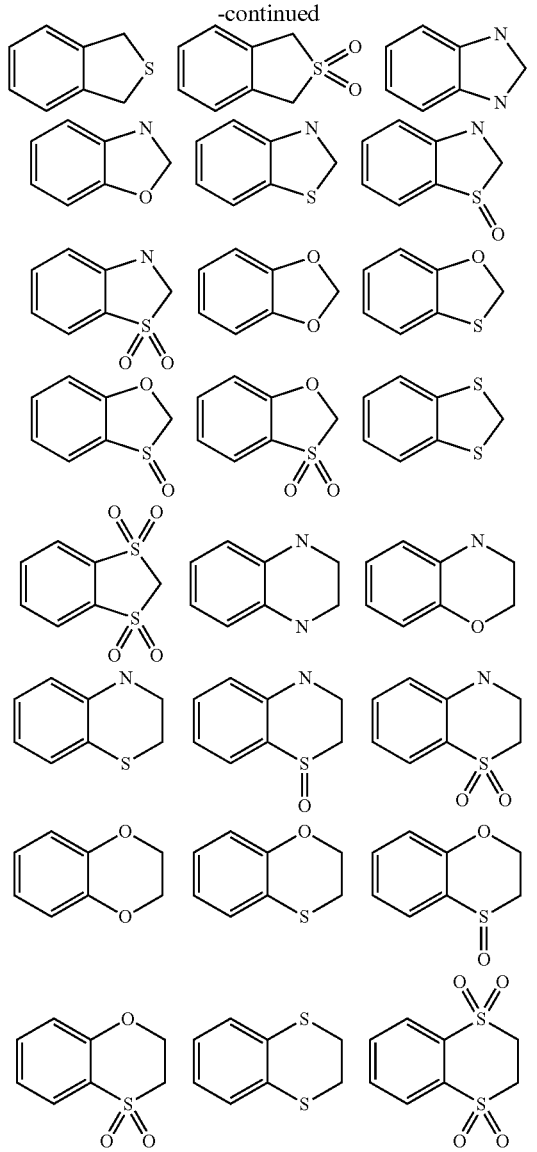

The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

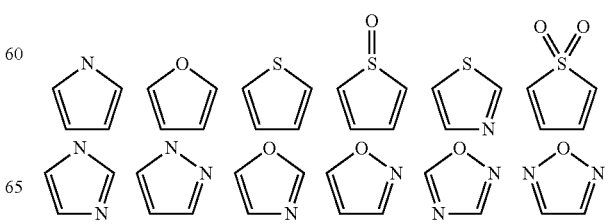

-continued

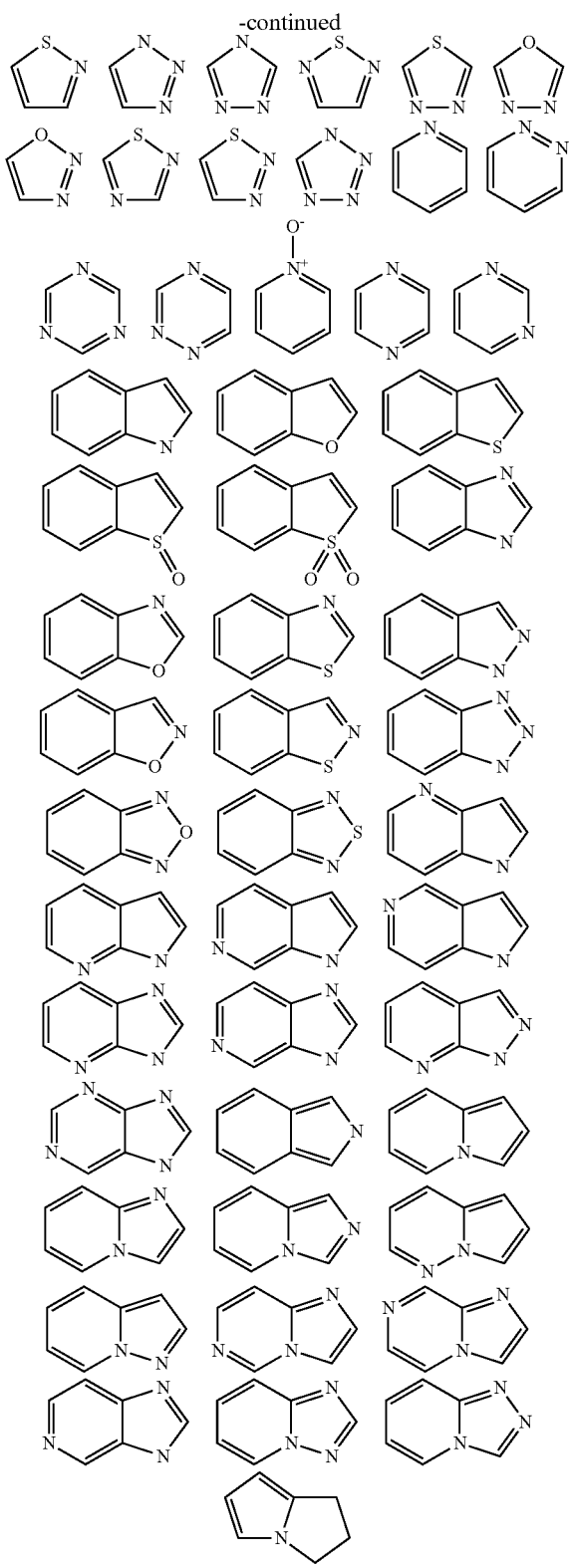

PREFERRED EMBODIMENTS

Preferred are the above mentioned compounds of formula 1 wherein $R^1$ is an 5 or 6 membered aromatic, hetero aromatic, non aromatic cyclic or heterocyclic ring system, optionally substituted by one, two or three residues selected from halogen or $C_{1-6}$-alkyl, optionally substituted with one or more F atoms.

Preferred are the above mentioned compounds of formula 1 wherein $R^1$ is an 5 or 6 membered aryl, heterocyclyl or heteroaryl ring optionally substituted by one, two or three residues selected from halogen or $C_{1-6}$-alkyl, optionally substituted with one or more F atoms.

Preferred are the above mentioned compounds of formula 1 wherein $R^1$ is phenyl or furanyl, optionally substituted by one or two residues selected from halogen or $C_{1-6}$-alkyl, optionally substituted with one or more F atoms.

Preferred are the above mentioned compounds of formula 1 wherein A is a N-linked four-, five- or six membered non-aromatic ring, with an additional condensed or spiro attached four-, five- or six membered ring, forming a bicyclic heterocyclic ring system, wherein
  if present one CH group is optionally replaced by N; and
  one, two or three $CH_2$ groups are optionally replaced by $C_{1-6}$-alkyl-CH—, $(C_{1-6}$-alkyl$)_2$-C—, $C_{1-6}$-alkyl-OC(O)CH—, CO, O, NH, $(C_{1-6}$-alkyl)N—, $SO_2$, wherein $C_{1-6}$-alkyl groups are optionally substituted by OH.

Preferred are the above mentioned compounds of formula 1 wherein A is a bicyclic heterocyclic system of the formula

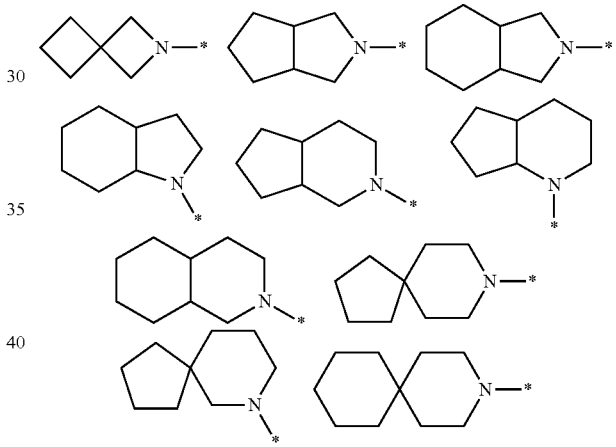

wherein
  if present one CH group is optionally replaced by N; and
  one, two or three $CH_2$ groups are optionally replaced by $C_{1-6}$-alkyl-CH—, $(C_{1-6}$-alkyl$)_2$-C—, $C_{1-6}$-alkyl-OC(O)CH—, CO, O, NH, $(C_{1-6}$-alkyl)N—, $SO_2$, wherein $C_{1-6}$-alkyl groups are optionally substituted by OH Preferred are the above mentioned compounds of formula 1 wherein
$R^1$ is selected from the group consisting of phenyl, furanyl, optionally substituted by one or two residues selected from halogen or $C_{1-6}$-alkyl, optionally substituted with F;
$X^1$ is absent or a branched or unbranched $C_{1-4}$-alkyl; said alkyl optionally substituted with one or more F atoms; preferably absent or $CH(CH_2CH_3)$;
$R^2$ is H;
$R^3$ is H, halogen, CN, $C_{1-6}$-alkyl, optionally substituted with F; preferably $R^3$ is H or Cl;
A is a N-linked four-, five- or six membered non-aromatic ring, with an additional condensed or spiro attached four-, five- or six membered ring, forming a bicyclic heterocyclic ring system, wherein
  if present one CH group is optionally replaced by N; and one, two or three CH$_2$ groups are optionally replaced by C$_{1-6}$-alkyl-CH—, (C$_{1-6}$-alkyl)$_2$-C—, C$_{1-6}$-alkyl-OC(O)CH—, CO, O, NH, (C$_{1-6}$-alkyl)N—, SO$_2$, wherein C$_{1-6}$-alkyl groups are optionally substituted by OH or a pharmaceutically acceptable salt thereof.

Preferred are the above mentioned compounds of formula 1 wherein

R$^1$ is selected from the group consisting of phenyl, furanyl, optionally substituted by one or two residues selected from halogen or C$_{1-4}$-alkyl, optionally substituted with F;

X$^1$ is absent or a branched or unbranched C$_{1-4}$-alkyl; said alkyl optionally substituted with one or more F atoms; preferably absent or CH(CH$_2$CH$_3$);

R$^2$ is H;

R$^3$ is H, halogen, CN, C$_{1-4}$-alkyl, optionally substituted with F; preferably R$^3$ is H or Cl;

A is a N-linked four-, five- or six membered non-aromatic ring, with an additional condensed or spiro attached four-, five- or six membered ring, forming a bicyclic heterocyclic ring system, wherein if present one CH group is optionally replaced by N; and one, two or three CH$_2$ groups are optionally replaced by C$_{1-6}$-alkyl-CH—, (C$_{1-6}$-alkyl)$_2$-C—, C$_{1-6}$-alkyl-OC(O)CH—, CO, O, NH, (C$_{1-6}$-alkyl)N—, SO$_2$, wherein C$_{1-6}$-alkyl groups are optionally substituted by OH or a pharmaceutically acceptable salt thereof.

Preferred are the above mentioned compounds of formula 1 wherein

R$^1$ is selected from the group consisting of phenyl, furanyl, optionally substituted by one or two residues selected from Me, CF$_3$, F, Cl, X$^1$ is absent or a branched or unbranched C$_{1-4}$-alkyl; said alkyl optionally substituted with one or more F atoms; preferably absent or CH(CH$_2$CH$_3$);

R$^2$ is H;

R$^3$ is H, Cl, CN, CF$_3$; preferably H or Cl; preferably Cl;

A is a bicyclic heterocyclic system of the formula

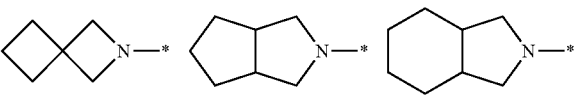

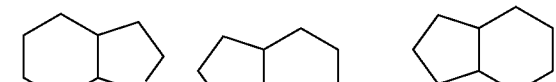

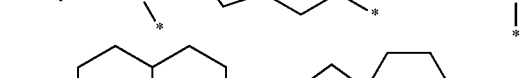

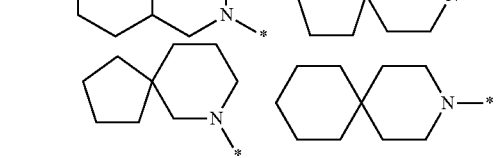

wherein if present one CH group is optionally replaced by N; and one, two or three CH$_2$ groups are optionally replaced by CHMe, CMe$_2$, CHCH$_2$OH, CHCOOMe, CO, O, NH, NMe, SO$_2$ or a pharmaceutically acceptable salt thereof.

Preferred are the above mentioned compounds of formula 1 wherein

R$^1$ is selected from the group consisting of phenyl, furanyl, optionally substituted by one or two residues selected from Me, CF$_3$, F, Cl;

X$^1$ is absent or a branched or unbranched C$_{1-4}$-alkyl; said alkyl optionally substituted with one or more F atoms; preferably absent or CH(CH$_2$CH$_3$);

R$^2$ is H;

R$^3$ is H, Cl, CN, CF$_3$; preferably H or Cl; preferably Cl;

A is a bicyclic heterocyclic system of the formula

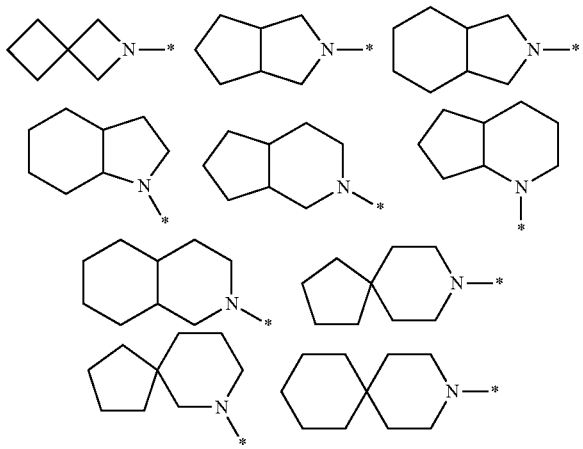

wherein if present one CH group is optionally replaced by N; and one or two CH$_2$ group is groups are optionally replaced by CO, O or NH or a pharmaceutically acceptable salt thereof.

Preferred are the above mentioned compounds of formula 1 wherein

R$^1$ is selected from the group consisting of phenyl, furanyl, optionally substituted by one or two residues selected from Me, CF$_3$, F, Cl;

X$^1$ is absent or a branched or unbranched C$_{1-4}$-alkyl; said alkyl optionally substituted with one or more F atoms; preferably absent or CH(CH$_2$CH$_3$);

R$^2$ is H;

R$^3$ is H, Cl, CN, CF$_3$; preferably H or Cl; preferably Cl

A is a bicyclic heterocyclic system of the formula

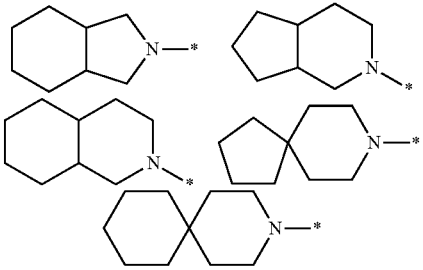

wherein if present one CH group is optionally replaced by N; and one or two CH$_2$ group is groups are optionally replaced by CO, O or NH or a pharmaceutically acceptable salt thereof.

Preferred are the above mentioned compounds of formula 1 wherein $R^1$ is selected from the group consisting of phenyl, furanyl, optionally substituted by one or two residues selected from Me, $CF_3$, F, Cl;
$X^1$ is absent or a branched or unbranched $C_{1-4}$-alkyl; said alkyl optionally substituted with one or more F atoms; preferably absent or $CH(CH_2CH_3)$;
$R^2$ is H;
$R^3$ is H, Cl, CN, $CF_3$; preferably H or Cl; preferably Cl
A is a bicyclic heterocyclic system of the formula

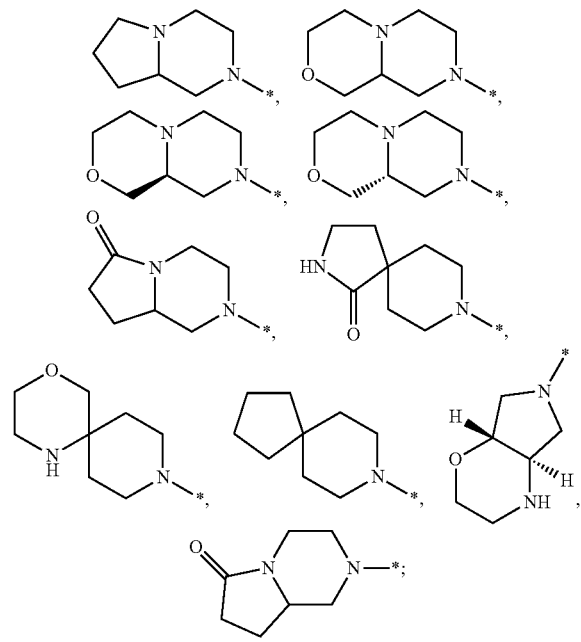

or a pharmaceutically acceptable salt thereof.

Preferred are the above mentioned compounds of formula 1 wherein
$R^1$ is selected from the group consisting of phenyl, furanyl, optionally substituted by one or two residues selected from Me, $CF_3$, F, Cl;
$X^1$ is absent or a branched or unbranched $C_{1-4}$-alkyl; said alkyl optionally substituted with one or more F atoms; preferably absent or $CH(CH_2CH_3)$;
$R^2$ is H;
$R^3$ is H, Cl, CN, $CF_3$; preferably H or Cl; preferably Cl
A is a bicyclic heterocyclic system of the formula

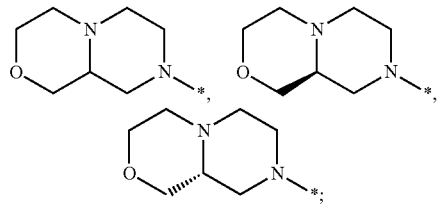

or a pharmaceutically acceptable salt thereof.
Preferred are the above mentioned compounds of formula 1 wherein
$R^1$ is selected from the group consisting of phenyl, furanyl, optionally substituted by one or two residues selected from Me, $CF_3$, F, Cl;
$X^1$ is absent or a branched or unbranched $C_{1-4}$-alkyl; said alkyl optionally substituted with one or more F atoms; preferably absent or $CH(CH_2CH_3)$;
$R^2$ is H;
$R^3$ is H, Cl, CN, $CF_3$; preferably H or Cl; preferably Cl
A is a bicyclic heterocyclic system of the formula

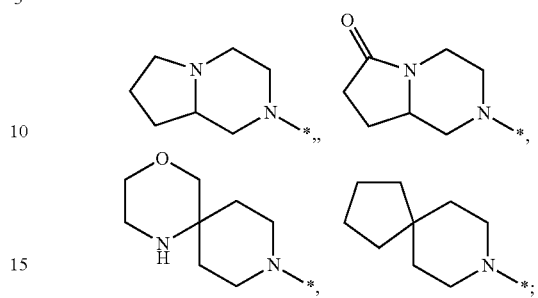

or a pharmaceutically acceptable salt thereof.

Preferred are the above mentioned compounds of formula 1 wherein
$R^1$ is selected from the group consisting of phenyl, furanyl, optionally substituted by one or two residues selected from Me, $CF_3$, F, Cl;
$X^1$ is absent or a branched or unbranched $C_{1-4}$-alkyl; said alkyl optionally substituted with one or more F atoms; preferably absent or $CH(CH_2CH_3)$;
$R^2$ is H;
$R^3$ is H, Cl, CN, $CF_3$; preferably H or Cl; preferably Cl
A is a bicyclic heterocyclic system of the formula

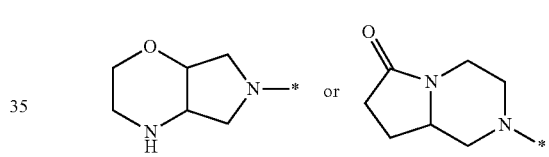

or a pharmaceutically acceptable salt thereof.

Preparation

General Procedures
Compounds of general formula (Z);

Formula (Z)

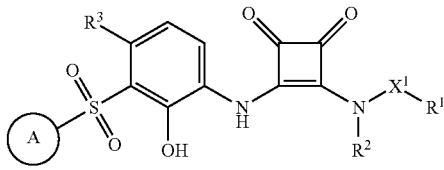

can be synthesised according to the following general procedures using suitable reagents and methods known to those skilled in the art:

A suitable bicyclic amine, optionally protected with protecting group P where necessary, can be reacted with 2-tert-butyl-6-chloro-benzooxazole-7-sulfonyl chloride or a similar reagent in the presence of a suitable base to give intermediate A. Hydrolysis under acid conditions gives intermediate B which can be converted by reaction with 3,4-diethoxy-3-cyclobutene-1,2-dione or a similar reagent to give Intermediate C. Treatment with a suitable amine under either basic or acid catalysed conditions leads to intermediate D. Protecting groups (if used) can then be removed to give the required Product as shown in general Scheme 1 below.

Suitable protecting groups P for the syntheses described above and suitable conditions for their use can be chosen by

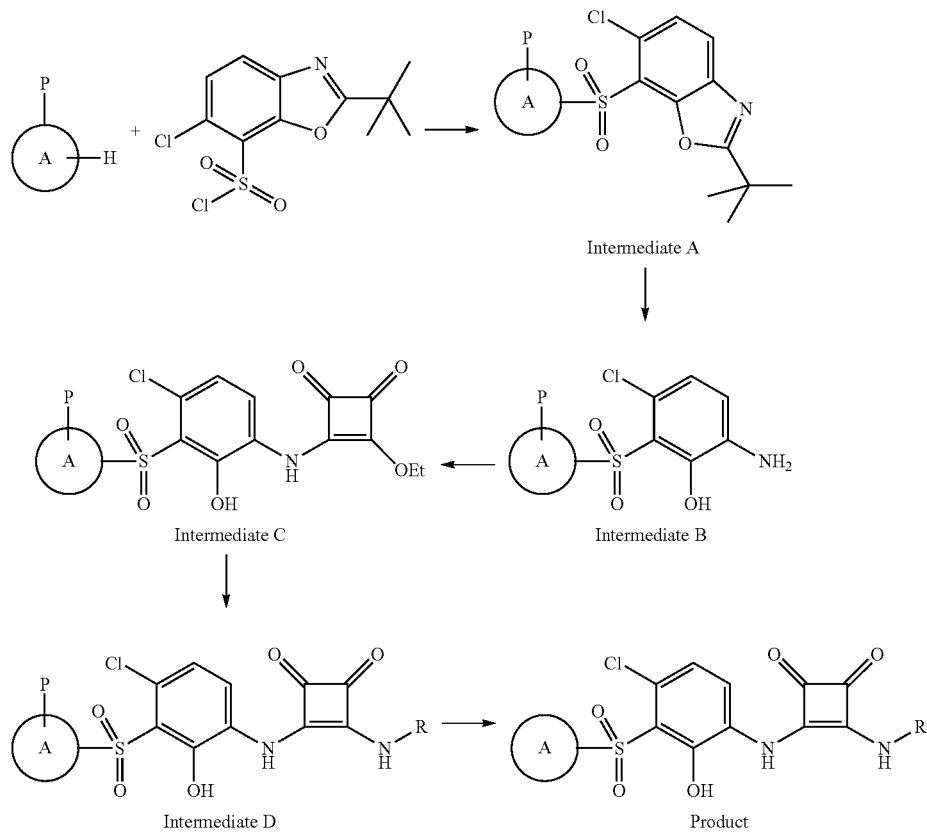

Alternatively, a suitable amine can be reacted with 3,4-diethoxy-3-cyclobutene-1,2-dione or a similar reagent to give Intermediate E, which can then be reacted with intermediate B, synthesised as described in Scheme 1 to give Intermediate D Protecting groups (if used) can then be removed to give the required Product as shown in the general Scheme 2 below.

those skilled in the art from examples described in "Protecting Groups, 3$^{rd}$ Edition", Philip J. Kocienski, Theime, 2005 or "Greene's Protective Groups in Organic Synthesis, 4th Edition", Peter G. M. Wuts, Theadora W. Greene, John Wiley and Sons, 2007.

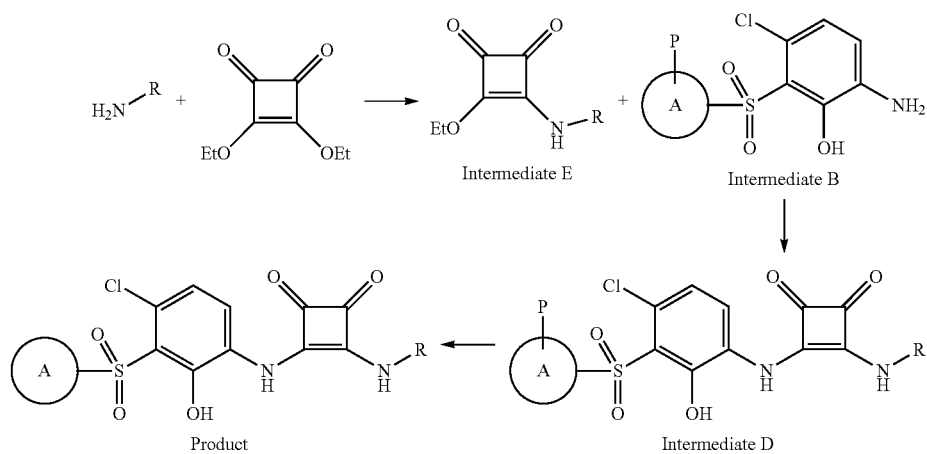

ABBREVIATIONS

| | |
|---|---|
| ACN | acetonitrile |
| APCI | atmospheric pressure chemical ionization (in MS) |
| BOP | Benzotriazole-1-yl-oxy-tris-(dimethylamino)-phosphonium hexafluorophosphate |
| br | broad (NMR) |
| Ctrl | control |
| DAD | diode array detector |
| DCM | dichloromethane |
| d | doublet (NMR) |
| DMA | N,N-dimethylacetamide |
| DMF | N,N-dimethylformamide |
| DMSO | dimethyl sulfoxide |
| EI | electron impact (in MS) |
| ES | electrospray (in MS) |
| GC/MS | gas chromatography with mass spectrometric detection |
| h | hour(s) |
| HATU | O-(7-azabenzotriazol-1-yl)-N,N,N',N'-tetramethyluronium hexafluoro-phosphate |
| HPLC | high performance liquid chromatography |
| HPLC/MS | coupled high performance liquid chromatography-mass spectrometry |
| m | multiplet (NMR) |
| min | minutes |
| MS | mass spectrometry |
| NMR | nuclear magnetic resonance |
| NM | N-Methyl-2-pyrrolidinone |
| PyBOP | (Benzotriazol-1-yloxy)tripyrrolidinophosphonium hexafluorophosphate |
| $R_t$ | retention time (in HPLC) |
| s | singlet (NMR) |
| SCX | Strong Cation Exchange |
| sec | secondary |
| t | triplet (NMR) |
| TBTU | O-(1H-benzo-1,2,3-triazol-1-yl)-N,N,N',N'-tetramethyluronium tetrafluoroborate |
| tert | tertiary |
| TFA | trifluoroacetic acid |
| THF | tetrahydrofuran |
| TLC | thin-layer chromatography |
| UV | ultraviolet absorption |

Analytical Methods
HPLC-MS

HPLC-MS and UPLC-MS are performed according to the following methods:

UPLC Method 1

| Instrument: | LC/MS Waters Acquity UPLC System DAD, SQD single quadrupole |
|---|---|
| Column: | HSS C18 1.8 μm 2.1 × 50 mm, Temp 35° C. |
| Mobile phase: | A = $H_2O$ 90% + 10% $CH_3CN$ + $CF_3COOH$ 0.1%<br>B = $CH_3CN$ 90% + $H_2O$ 10% |

| Time in min | % A | % B | flow rate in ml/min |
|---|---|---|---|
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

| Detection: | UV 254 nm |
|---|---|
| Detection: | SQD, single quadrupole |
| Ion source: | ES+/ES− |
| Scan range: | 90-900 amu |

UPLC Method 2

| Instrument: | LC/MS Waters Acquity UPLC System DAD, SQD single quadrupole |
|---|---|
| Column: | BEH C18 1.7 μm 2.1 × 50 mm, Temp 35° C. |
| Mobile phase: | A = $H_2O$ 90% + 10% $CH_3CN$ + $NH_4COOH$ 5 mM<br>B = $CH_3CN$ 90% + $H_2O$ 10% |

| Time in min | % A | % B | flow rate in ml/min |
|---|---|---|---|
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

| Detection: | UV 254 nm |
|---|---|
| Detection: | SQD, single quadrupole |
| Ion source: | ES+/ES− |
| Scan range: | 90-900 amu |

UPLC Method 3

| Instrument: | LC/MS Waters Acquity UPLC System DAD, SQD single quadrupole |
|---|---|
| Column: | HSS C18 1.8 μm 2.1 × 50 mm, Temp 35° C. |
| Mobile phase: | A = $H_2O$ 90% + 10% $CH_3CN$ + $CF_3COOH$ 0.1%<br>B = $CH_3CN$ 90% + $H_2O$ 10% |

| Time in min | % A | % B | flow rate in ml/min |
|---|---|---|---|
| 0.00 | 100 | 0 | 0.70 |
| 0.70 | 0 | 100 | 0.70 |
| 2.30 | 0 | 100 | 0.70 |
| 2.40 | 100 | 0 | 0.70 |
| 2.60 | 100 | 0 | 0.70 |

| Detection: | UV 254 nm |
|---|---|
| Detection: | SQD, single quadrupole |
| Ion source: | ES+/ES− |
| Scan range: | 90-900 amu |

HPLC Method 4

| Instrument: | LC/MS Waters. Hplc Alliance 2695 DAD, ZQ Quadrupole. |
|---|---|
| Column: | Zorbax Eclipse Plus C18, 3.5 μm, 4.6 × 50 mm |
| Mobile phase: | A = $H_2O$ 90% + $NH_4COOH$ 5 mM + 10% acetonitrile<br>B = acetonitrile |
| Flow rate: | 1300 uL/min |
| Gradient: | A/B(90:10), then to A/B (10:90) in 3.50 minutes for 1 minute |
| Detection: | UV @ 254 nm |
| Detection: | Waters ZQ, Quadrupole |
| Ion source: | ES |
| Scan range: | 120-900 |

HPLC Method 5

| Instrument: | LC/MS Waters. Hplc Alliance 2695 DAD, ZQ Quadrupole. |
|---|---|
| Column: | Gemini C18, 3 um 3 um, 4.6 × 506 × 50 mm |
| Mobile phase: | A = $H_2O$ 90% + 0.1% TFA + 10% acetonitrile<br>B = acetonitrile |
| Flow rate: | 1300 uL/min |
| Gradient: | A/B(70:30), then to A/B (10:90) in 3.50 minutes for 1 minute |

-continued

| Detection: | UV @ 254 nm |
| Detection: | Waters ZQ, Quadrupole |
| Ion source: | ES |
| Scan range: | 120-900 |

HPLC Method 6

| Instrument: | LC/MS ThermoFinnigan HPLC Surveyor DAD, MSQ single quadrupole |
| Column: | Synergi Hydro RP80A, 4 μm, 4.6 × 100 mm |
| Mobile phase: | A = $H_2O$ 90% + 10% acetonitrile + $NH_4COOH$ 10 mM<br>B = acetonitrile 90% + $H_2O$ 10% + $NH_4COOH$ 10 mM |

| Time in min: | % A | % B | Flow rate in ml/min |
|---|---|---|---|
| 0.00 | 100 | 0 | 1.2 |
| 1.50 | 100 | 0 | 1.2 |
| 11.5 | 0 | 100 | 1.2 |
| 13 | 0 | 100 | 1.2 |
| 13.5 | 100 | 0 | 1.2 |
| 15 | 100 | 0 | 1.2 |

| Detection: | UV 254 nm |
| Detection: | Finnigan MSQ, single quadrupole |
| Ion source: | APCI+/APCI− |
| Scan range: | 100-900 amu |

HPLC Method 7

| Instrument: | LC/MS ThermoFinnigan HPLC Surveyor DAD, LCQDuo Ion Trap |
| Column: | Simmetry Shield RP8, 5 μm, 4.6 × 150 mm |
| Mobile phase: | A = $H_2O$ 90% + 10% acetonitrile + HCOOH 0.1%<br>B = acetonitrile 90% + $H_2O$ 10% + HCOOH 0.1% |

| Time in min: | % A | % B | Flow rate in ml/min |
|---|---|---|---|
| 0.00 | 95 | 5 | 1 |
| 1.50 | 95 | 5 | 1 |
| 11.5 | 5 | 95 | 1 |
| 13 | 5 | 95 | 1 |
| 13.3 | 95 | 5 | 1 |
| 15 | 95 | 5 | 1 |

| Detection: | UV 254 nm |
| Detection: | Finnigan LCQDuo, Ion Trap |
| Ion source: | ES+ |
| Scan range: | 100-900 amu |

GC-MS
GC-MS were performed under the following conditions:
GCMS Method 8

| Instrument: | GC/MS Thermo Scientific TRACE GC ULTRA, DSQ II MS single quadrupole |
| Column: | Agilent DB-5MS, 25 m × 0.25 mm × 0.25 μm |
| Carrier gas: | Helium, 1 ml/min costant flow |
| Oven Program: | 50° C., to 100° C. in 10° C./min,<br>to 200° C. in 20° C./min,<br>to 320° C. in 30° C./min (hold 10 min). |
| Detection: | DSQ II MS single quadrupole |
| Ion source: | EI |
| Scan range: | 50-450 amu |

NMR
NMR are recorded on Varian 400 MHz or Varian Inova 500 MHz instruments. Chemical shifts are expressed in parts per million (ppm) relative to tetramethylsilane using the solvent residual peak as internal standard

SYNTHETIC EXAMPLES

All materials used are purchased from commercial sources unless otherwise stated. References are given for the syntheses of non commercially available reagents Flash chromatography is performed on prepacked silica gel columns from Biotage using FlashVac (IST), Flashmaster (Argonaut) SP1 or Isolera (Biotage) manual and automatic purification systems.

SCX columns are purchased from Biotage or Phenomenex and are washed with methanol prior to use.

Reactions are monitored by TLC using suitable solvents and visualisation by UV absorbance or a suitable staining reagent.

Semi-preparative reverse phase HPLC is performed on a C18 column using a gradient of acetonitrile:0.5% TFA in water, 1:9-9:1 or a gradient of acetonitrile:0.5% NH4COOH in water, 1:9-9:1. Automatic fraction collection is triggered by mass spectrometry.

Synthesis of Example 1

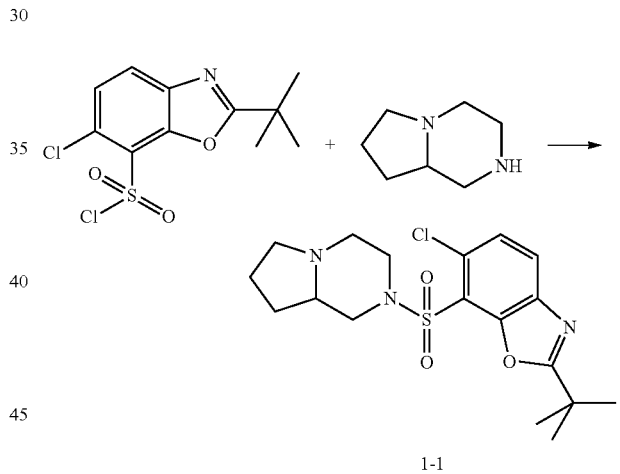

1-1

A solution of octahydro-pyrrolo[1,2-a]pyrazine (500 mg, 3.96 mmol) in tetrahydrofuran (6 mL) is cooled to 0° C. and triethylamine (552 μL, 3.96 mmol) and a solution of 2-tert-butyl-6-chloro-benzooxazole-7-sulfonyl chloride (1.22 g, 3.96 mmol, US2003216375) in tetrahydrofuran (4 mL) is added. The reaction mixture is stirred at room temperature overnight. Volatiles are evaporated under reduced pressure and the residue is partitioned between water and ethyl acetate and the aqueous layer extracted with ethyl acetate. The organic layers are combined, dried over $MgSO_4$, and the solvent removed under vacuum. The residue is purified by flash chromatography (Silica Gel, gradient: cyclohexane/ethyl acetate from 60:40 to 50:50) to give compound 1-1.

Yield: 1.47 g

ES mass spectrum: $[M+H]^+=398$

Retention time HPLC: 1.26 min (UPLC method 2)

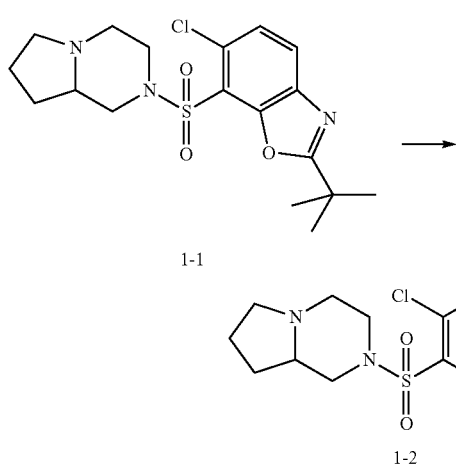

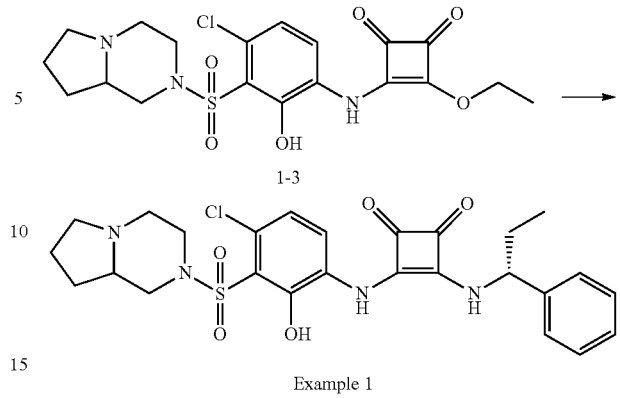

To a solution of compound 1-4 (493 mg, 1.24 mmol) in dioxane (4 mL) are added water (800 μL) and sulphuric acid (800 μL) and the mixture is heated under reflux overnight. The solution is cooled to 0° C., basified with 32% NaOH in water and then filtered and extracted four times with ethyl acetate. The organic layers are combined, dried over MgSO4, and the solvent removed under vacuum to give compound 1-2.

Yield: 347 mg

ES mass spectrum: [M+H]+=332

Retention time HPLC: 1.01 min (UPLC method 2)

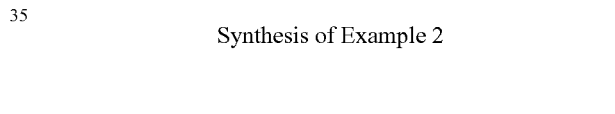

Compound 1-2 (347 mg, 1.046 mmol) is dissolved in ethanol (7 mL), 3,4-diethoxy-cyclobut-3-ene-1,2-dione (154 μL, 1.050 mmol) and triethylamine (146.35 μL, 1.050 mmol) are added and the solution refluxed for 2 h. Volatiles are evaporated under reduced pressure and the residue is partitioned between water and dichloromethane and the aqueous layer extracted with dichloromethane. The organic layers are combined, dried, and the solvent is removed under vacuum. The residue is purified by flash chromatography (Silica Gel, dichloromethane:ethanol 90:2) to give compound 1-3.

Yield: 209 mg

ES mass spectrum: [M+H]+=456

Retention time HPLC: 0.89 min (UPLC method 2)

A mixture of compound 1-3 (100 mg, 0.22 mmol) and (R)-1-phenyl-propylamine (32 μL, 0.22 mmol) in ethanol (8 mL) are heated under reflux for 4 h and then stirred at room temperature overnight. The solvent is evaporated under reduced pressure and the residue purified via semi-preparative reversed phase HPLC to give Example 1.

Yield: 70 mg

ES mass spectrum: [M+H]+=545

Retention time HPLC: 9.14 min (HPLC method 6)

1H NMR (Varian 400 MHz. DMSO-d6; 28° C.) 9.42 (1H, s); 8.79 (1H, d); 7.90 (1H, d); 7.42-7.34 (4H, m); 7.30 (1H, m); 6.85 (1H, br); 5.10 (1H, m); 3.80 (1H, d); 3.65 (1H, d); 3.06 (3H, m); 2.76 (1H, m); 2.28 (3H, m); 2.00-1.80 (3H, m); 1.71 (2H, m); 1.67 (2H, m); 0.91 (3H, t) 1H not observed.

Synthesis of Example 2

Compound 1-3 (50 mg, 0.11 mmol) is allowed to react with (R)-1-(5-methyl-furan-2-yl)propylamine (31 mg, 0.22 mmol, Journal of Medicinal Chemistry, 2006, vol. 49, p. 7603-7606) in a manner analogous to that used for the synthesis of compound 1-4 to give Example 2

Yield: 40 mg

ES mass spectrum: [M+H]+=547

Retention time HPLC: 9.20 min (HPLC method 6)

1H NMR (Varian Inova 500 MHz. DMSO-d6; 27° C.) 10.50 (1H, br); 9.41 (1H, s); 8.77 (1H, d); 7.94 (1H, d); 6.91 (1H, br); 6.24 (1H, d); 6.03 (1H, m); 5.12 (1H, m); 3.80 (1H, d); 3.65 (1H, d); 3.05 (3H, m); 2.74 (1H, m); 2.26 (3H, s); 2.26 (2H, br); 1.97-1.78 (3H, m); 1.74 (2H, m); 1.33 (1H, m); 0.91 (3H, t) 1H not observed.

Synthesis of Example 3

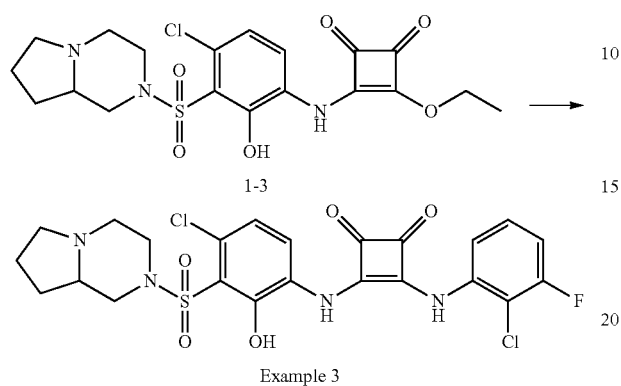

Compound 1-3 (50 mg, 0.11 mmol) is suspended in absolute ethanol (4 mL) and 2-chloro-3-fluoro aniline (160 mg, 9.72 mmol) and 37% hydrochloric acid (3 drops) are added. The mixture is stirred at reflux for 6 hours then cooled to room temperature and neutralised with 10% sodium hydroxide solution. The solvent is removed, the residue partitioned between water and ethyl acetate, the phases separated and the aqueous phase extracted twice with ethyl acetate. The combined organic extracts are washed with brine, dried over magnesium sulphate and the solvent removed. The residue is purified by flash chromatography (silica gel, DCM/methanol/ammonium hydroxide 90:5:1) and the product obtained triturated with ethanol to give Example 3.
  Yield: 14 mg
  ES mass spectrum: [M+H]$^+$=555
  Retention time HPLC: 8.72 min (HPLC method 6)
  1H NMR (Varian Inova 500 MHz. DMSO-d6; 27° C.) 10.35 (1H, br); 10.17 (1H, br); 7.70 (1H, br); 7.38 (2H, m); 7.16 (1H, m) 6.90 (1H, br); 3.82 (1H, d); 3.66 (1H, d); 3.06 (3H, s, br); 2.82 (1H, m); 2.27 (2H, m); 1.85-1.70 (3H, m); 1.34 (2H, m). 1H not observed.

Synthesis of Example 4

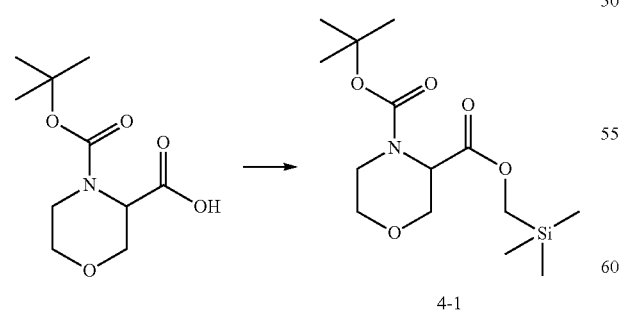

Morpholine-3,4-dicarboxylicacid 4-tert-butyl ester (4 g, 17.3 mmol) is dissolved in dry diethyl ether (40 mL) under nitrogen and trimethylsilyldiazomethane (2 M in diethyl ether, 16 mL, 32 mmol) is added. The mixture is stirred for 2 hours then methanol (4 mL) is added and the mixture stirred overnight. The solvent is evaporated to give crude compound 4-1
  Yield: 5.49 g
  EI mass spectrum: [M]$^+$=317
  Retention time GC: 10.81 min (GCMS method 8)

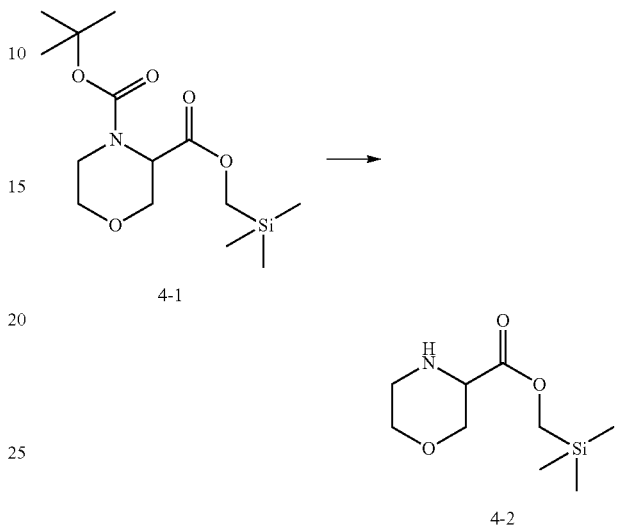

Compound 4-1 (5.49 g, 17.3 mmol) is dissolved in DCM (40 mL) and trifluoroacetic acid (10 mL) is added and the mixture stirred for 5 hours. The solution is loaded onto 2×50 g SCX cartridges, washed with methanol (200 mL) and then eluted with 1 M ammonia solution in methanol (200 mL). The solvent is removed under reduced pressure to give crude compound 4-2.
  Yield: 3.3 g
  EI mass spectrum: [M]$^+$=217
  Retention time GC: 8.56 min (GCMS method 8)

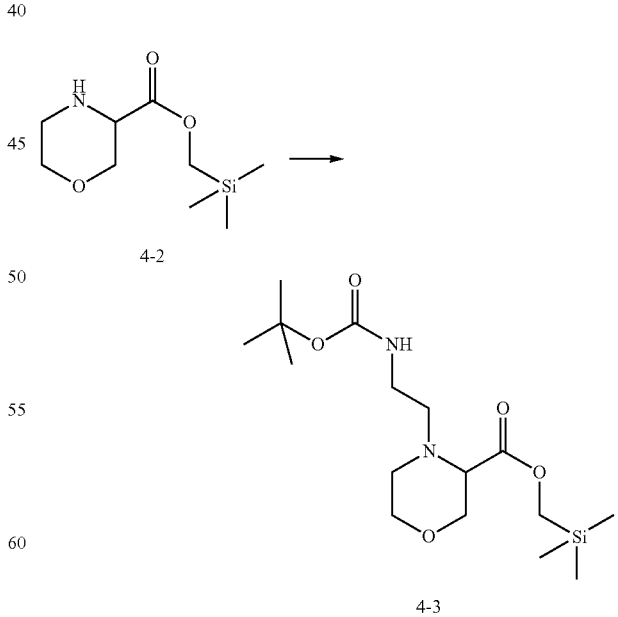

Compound 4-2 (3.3 g, 15.18 mmol) is dissolved in 1,2-dichloroethane (50 mL) under nitrogen atmosphere and tert-butyl-N-(2-oxoethyl)carbamate (3.63 g, 22.78 mmol) and sodium triacetoxyborohydride (9 g, 42.5 mmol) are added. The mixture is stirred for 16 hours at room temperature, then 6 hours at 60° C. then 3 days at room temperature. The solution is loaded onto 2×50 g SCX cartridges, washed with methanol (200 mL) and then eluted with 1 M ammonia solution in methanol (250 mL). The solvent is removed under reduced pressure to give crude compound 4-3.

Yield: 2.82 g

EI mass spectrum: [M]$^+$=360

Retention time GC: 13.06 min (GCMS method 8)

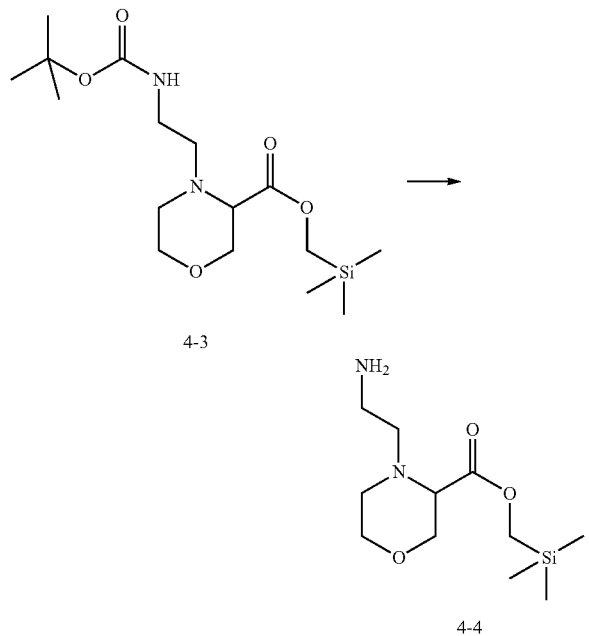

4-3

4-4

Compound 4-3 (2.82 g, 7.82 mmol) is dissolved in DCM (40 mL) and trifluoroacetic acid (20 mL) is added at 0° C. The mixture is stirred at 0° C. for 30 minutes then at room temperature for 4 hours. The solution is loaded onto 2×50 g SCX cartridges, washed with methanol (200 mL) and then eluted with 1 M ammonia solution in methanol (250 mL). The solvent is removed under reduced pressure to give crude compound 4-4.

Yield: 2.0 g

ES mass spectrum: [M-OCH$_2$SiMe$_3$]$^+$=157

Retention time HPLC: 1.24 min (HPLC method 6)

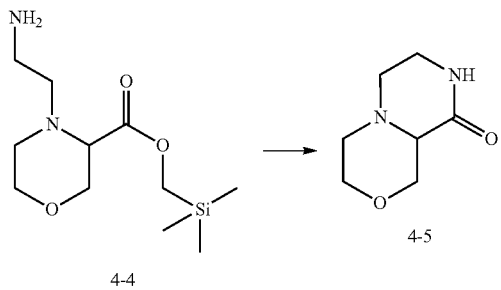 [SMILES: C[Si](C)(C)COC(=O)C1COCCN1CCN ; O=C1NCCN2CCOCC12]

4-4

4-5

Compound 4-4 (2.0 g, 7.68 mmol) is dissolved in methanol (80 mL) and heated at 40° C. for 3 hours. The solvent is removed and the residue purified by flash chromatography (Silica Gel, dichloromethane:methanol 95:5) to give compound 4-5.

Yield: 480 mg

EI mass spectrum: [M]$^+$=156

Retention time GC: 9.57 min (GCMS method 8)

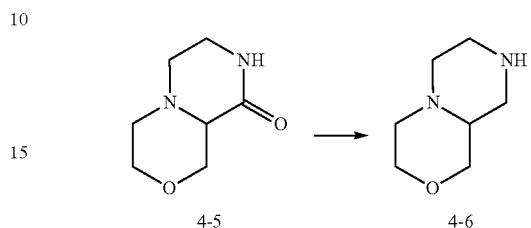

4-5

4-6

Compound 4-5 (150 mg, 0.96 mmol) is suspended in dry THF (5 mL) and borane THF complex (1 M in THF, 9.6 mL, 9.6 mmol) is added. The mixture is heated at 90° C. for 28 hours. The mixture is loaded onto a 10 g SCX cartridge, washed with methanol and then eluted with 2 M ammonia solution in methanol. The solvent is removed under reduced pressure, the residue cooled in an ice bath and hydrogen chloride (6 M in dioxane, 10 mL) added. The mixture is heated at 60° C. for 4 hours and the solvent removed. The mixture is loaded onto a 10 g SCX cartridge, washed with methanol and then eluted with 1 M ammonia solution in methanol. The solvent is removed under reduced pressure to give compound 4-6.

Yield: 70 mg

EI mass spectrum: [M]$^+$=142

Retention time GC: 6.77 min (GCMS method 8)

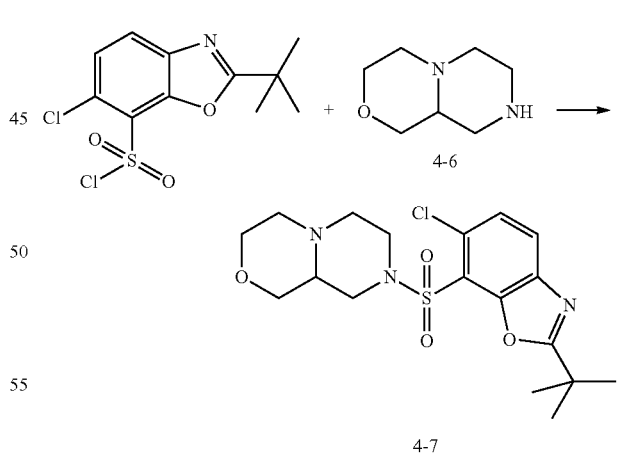

4-6

4-7

Compound 4-6 (150 mg, 1.05 mmol) is treated in a manner analogous to that described for the preparation of Compound 1-1 to give compound 4-7.

Yield: 420 mg

ES mass spectrum: [M+H]$^+$=414

Retention time UPLC: 1.14 min (UPLC method 2)

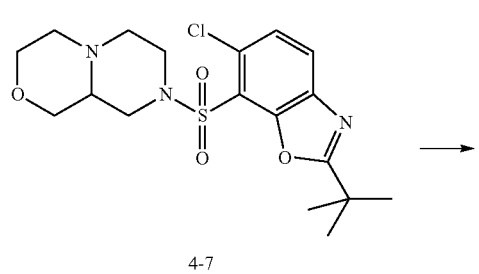

4-7

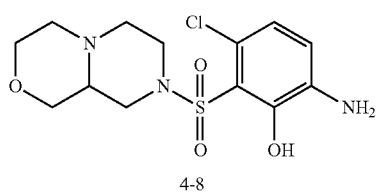

4-8

Compound 4-7 (420 mg, 1.01 mmol) is treated in a manner analogous to that described for the preparation of Compound 1-2 to give compound 4-8.

Yield: 330 mg

ES mass spectrum: [M+H]$^+$=348

Retention time UPLC: 0.89 min (UPLC method 2)

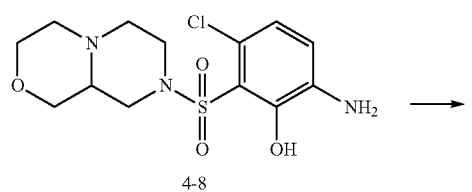

4-8

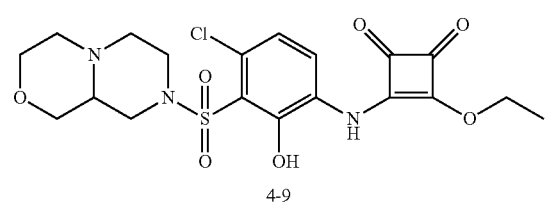

4-9

Compound 4-8 (150 mg, 0.43 mmol) is treated in a manner analogous to that described for the preparation of Compound 1-3 to give compound 4-9.

Yield: 173 mg

ES mass spectrum: [M+H]$^+$=472

Retention time UPLC: 0.90 min (UPLC method 2)

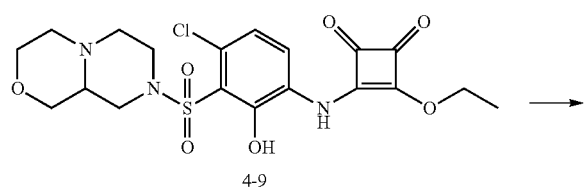

4-9

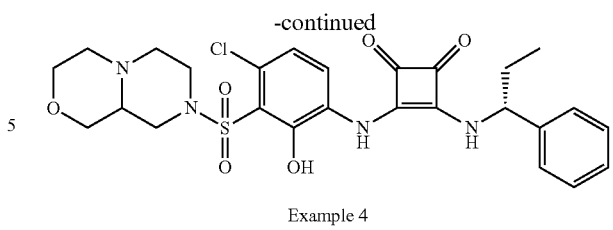

Example 4

Compound 4-9 (60 mg, 0.13 mmol) is treated in a manner analogous to that described for the preparation of Example 1 to give Example 4.

Yield: 40 mg

ES mass spectrum: [M+H]$^+$=561

Retention time HPLC: 9.46 min (HPLC method 7)

1H NMR (Varian 400 MHz. DMSO-d6; 28° C.) 9.44 (1H, br); 8.98 (1H, d); 7.71 (2H, br); 7.64 (1H, d); 7.41-7.36, (5H, m); 5.09 (1H, m); 3.68 (2H, m); 3.61-3.48 (2H, m); 3.04 (2H, m); 2.72 (2H, m); 2.59 (1H, m); 2.20-2.04 (3H, m); 1.79 (3H, m); 0.88 (3H, t).

Synthesis of Example 5

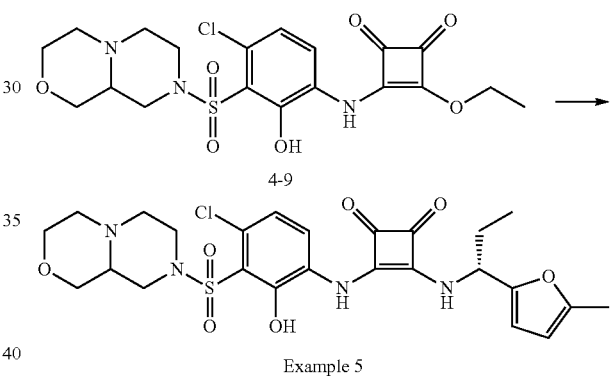

4-9

Example 5

Compound 4-9 (60 mg, 0.13 mmol) is treated in a manner analogous to that described for the preparation of Example 2 to give Example 5.

Yield: 35 mg

ES mass spectrum: [M+H]$^+$=565

Retention time HPLC: 8.70 min (HPLC method 6)

1H NMR (Varian Inova 500 MHz. DMSO-d6; 27° C.) 9.41 (1H, s); 8.76 (1H, d); 7.97 (1H, d); 6.25 (1H, d); 6.04 (1H, d); 5.10 (1H, m); 3.67 (3H, m); 3.50 (3H, m); 3.01 (2H, m); 2.70 (2H, m); 2.55 (2H, m); 2.26 (3H, s); 2.14 (3H, m); 1.90 (2H, m); 0.91 (3H, t).

Synthesis of Example 6

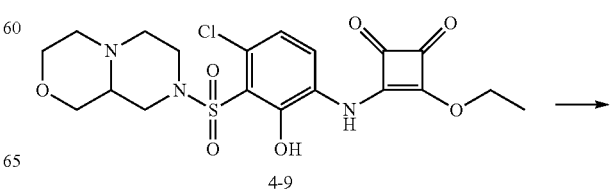

4-9

-continued

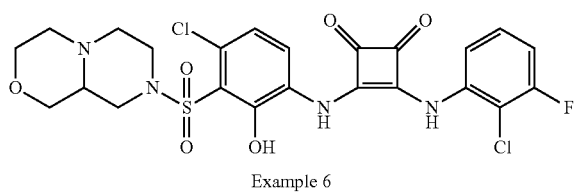

Example 6

Compound 4-9 (60 mg, 0.13 mmol), 2-chloro-3-fluoroaniline (93 mg, 0.64 mmol) and triethylamine (27 µL, 0.19 mmol) are suspended in ethanol (3 mL) and heated at reflux for 3 days. The solvent is removed and the residue purified by flash chromatography (silica gel, gradient 0-100% EtOAc in cyclohexane) then by preparative TLC (5% methanol in DCM) to give Example 6.

Yield: 18 mg

ES mass spectrum: $[M+H]^+=571$

Retention time HPLC: 9.24 min (HPLC method 7)

1H NMR (Varian Inova 500 MHz. DMSO-d6; 27° C.) 10.2 (3H, br); 7.75 (2H, m br); 7.39 (2H, m); 7.18 (1H, m); 3.67 (3H, m); 3.50 (2H, m); 3.03 (2H, m); 2.76 (1H, m); 2.63 (2H, m); 2.18 (3H, m).

Synthesis of Example 7

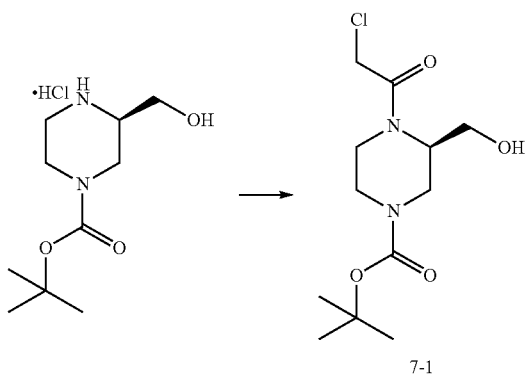 [SMILES: CC(C)(C)OC(=O)N1CCN[C@@H](CO)C1 ; Cl ; CC(C)(C)OC(=O)N1CCN(C(=O)CCl)[C@@H](CO)C1]

(R)-4-N-Boc-2-Hydroxymethyl-piperazine hydrochloride (1 g, 3.96 mmol) and triethylamine (1.65 mL, 11.87 mmol) are suspended in DCM (5 mL) and cooled to 0° C. Chloroacetyl chloride (0.35 mL, 4.35 mmol) is added and the mixture stirred overnight at room temperature. The solvent is evaporated under reduced pressure to give crude compound 7-1.

Yield: 1.2 g

ES mass spectrum: $[M-tBu+H]^+=237$

Retention time HPLC: 0.87 min (UPLC method 1).

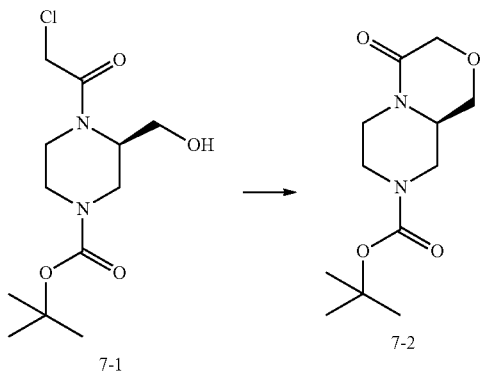 [SMILES: CC(C)(C)OC(=O)N1CCN(C(=O)CCl)[C@@H](CO)C1 ; CC(C)(C)OC(=O)N1CCN2C(=O)COC[C@H]2C1]

Compound 7-1 (1.2 g, 4.1 mmol) is suspended in THF (7 mL) and potassium tert-butoxide (552 mg, 4.92 mmol) is added. The mixture is stirred for 4 hours at room temperature and then the solvent is removed under reduced pressure. The residue is purified by flash chromatography (Silica Gel, gradient, cyclohexane:ethyl acetate, 100:0-0:100) to give compound 7-2.

Yield: 410 mg

EI mass spectrum: $[M]^+=256$

Retention time GC: 11.91 min (GCMS method 8).

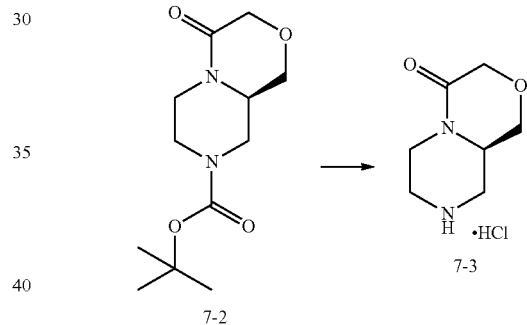

Compound 7-2 (410 mg, 1.6 mmol) is suspended in DCM (7 mL) and hydrogen chloride (4 M in dioxane, 20 mL) is added. The mixture is stirred for 90 minutes and then the solvent evaporated under reduced pressure to give compound 7-3.

Yield: 300 mg

ES mass spectrum: $[M+H]^+=157$

Retention time UPLC: 0.25 min (UPLC method 1).

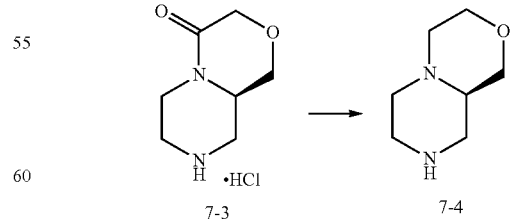

Compound 7-3 (300 mg, 1.56 mmol) is suspended in dry THF (5 mL) and borane:THF complex (1 M in THF, 10 mL, 10 mmol) is added. The mixture is heated at 90° C. overnight then cooled to 0° C. and 10 M hydrochloric acid (10 mL)

added. The resulting mixture is stirred at 60° C. for 4 hours and then concentrated under vacuum. The mixture is loaded onto an SCX cartridge, washed with methanol and eluted with 2 M NH₃ in methanol. The solvent is removed to give compound 7-4.

Yield: 210 mg

ES mass spectrum: [M]⁺=142

Retention time GC: 7.36 min (3A.2).

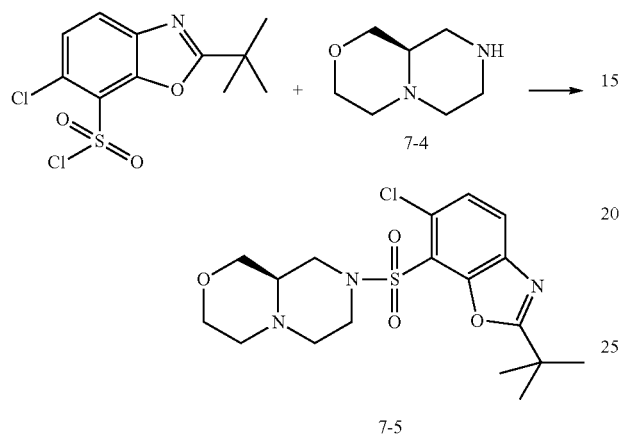

Compound 7-4 (115 mg, 0.81 mmol) is treated in a manner analogous to that described for the preparation of Compound 1-1 to give compound 7-5

Yield: 240 mg

ES mass spectrum: [M+H]⁺=414

Retention time UPLC: 1.14 min (UPLC method 2)

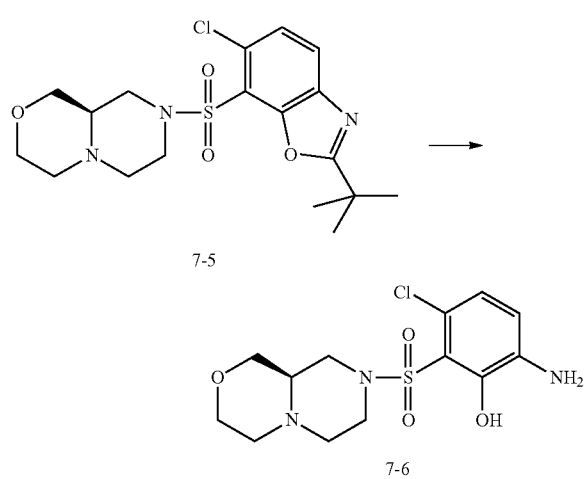

Compound 7-5 (240 mg, 0.58 mmol) is treated in a manner analogous to that described for the preparation of Compound 1-2 to give compound 7-6.

Yield: 190 mg

ES mass spectrum: [M+H]⁺=348

Retention time UPLC: 0.88 min (UPLC method 2)

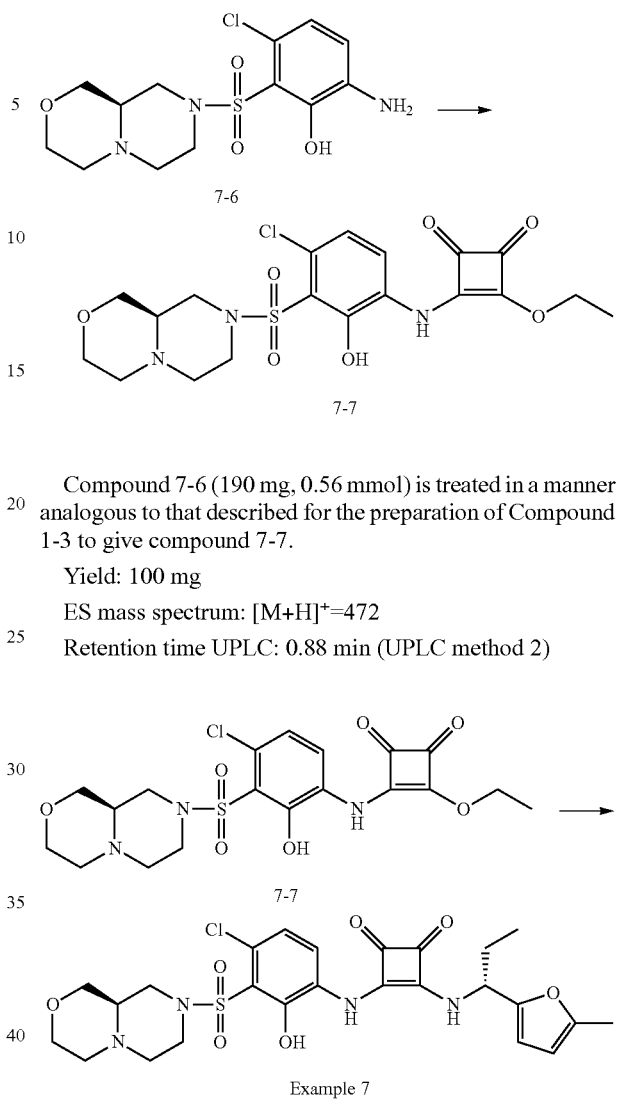

Compound 7-6 (190 mg, 0.56 mmol) is treated in a manner analogous to that described for the preparation of Compound 1-3 to give compound 7-7.

Yield: 100 mg

ES mass spectrum: [M+H]⁺=472

Retention time UPLC: 0.88 min (UPLC method 2)

Example 7

Compound 7-7 (50 mg, 0.11 mmol) is treated in a manner analogous to that described for the preparation of Example 2 to give Example 7.

Yield: 21 mg

ES mass spectrum: [M+H]⁺=565

Retention time HPLC: 9.27 min (HPLC method 7)

1H NMR (Varian 400 MHz. DMSO-d6; 28° C.) 10.4 (1H, br); 9.40 (1H, s); 8.75 (1H, d); 7.98 (1H, d); 7.06 (1H, br); 6.25 (1H, d); 5.99 (1H, d); 5.12 (1H, m); 3.70 (3H, m); 3.45 (2H, m); 2.99 (2H, m); 2.75 (1H, m); 2.56-2.60 (2H, m); 2.12-2.26 (6H, m); 1.86 (2H, m); 0.86 (3H, t).

Synthesis of Example 8

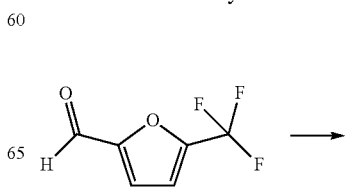

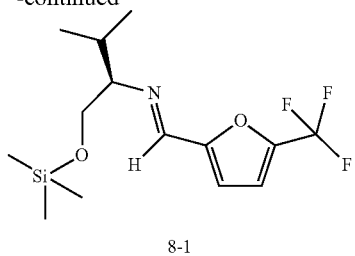

8-1

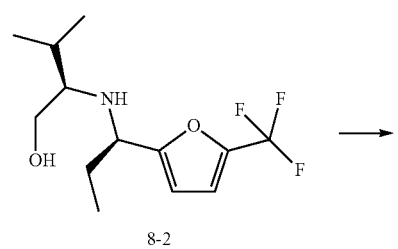

8-2

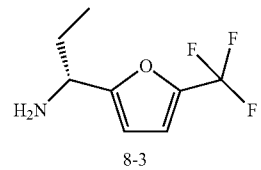

8-3

5-Trifluoromethyl-2-furaldehyde (998 mg, 6.08 mmol), (R)-2-amino-3-methyl-1-butanol (627 mg, 6.08 mmol) and magnesium sulphate (3.02 g, 25.05 mmol) are suspended in dry DCM (9 mL) at 0° C. and stirred for 2 hours at 0° C. and then overnight at room temperature. The mixture is passed through a filter and the solvent removed under reduced pressure. The residue is dissolved in DCM (11 mL) and chlorotrimethylsilane (845 μL, 6.69 mmol) and triethylamine (932 μL, 6.69 mmol) are added. The mixture is stirred overnight, passed through a filter and the solvent removed. The residue is suspended in 1:1 diethyl ether/n-hexane (50 mL), passed through a filter and the solvent removed to give compound 8-1.

Yield: 1.88 g
ES mass spectrum: [M+H]$^+$=322
Retention time HPLC: 1.63 min (UPLC method 2)

Compound 8-2 (516 mg, 1.85 mmol) is dissolved in methanol (8 mL), methylamine (40% in water, 2.46 mL), periodic acid (1.38 g, 6.04 mmol) and water (2.5 mL) are added and the mixture stirred for 3 hours. The mixture is diluted with water and extracted with diethyl ether. The organic extracts are dried over magnesium sulphate and concentrated under slightly reduced pressure to give crude compound 8-3 as a mixture with diethyl ether.

Yield: 530 mg
ES mass spectrum: [M-NH3]$^+$=177
Retention time HPLC: 0.73 min (UPLC method 1)

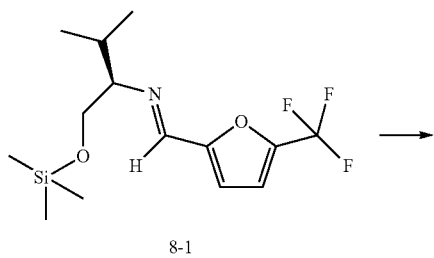

8-1

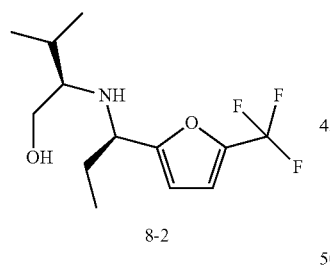

8-2

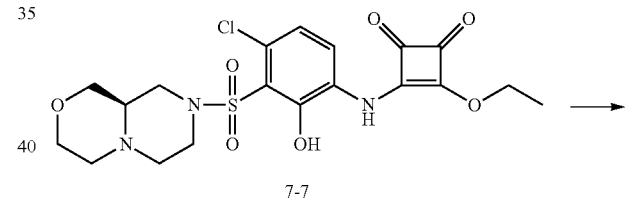

7-7

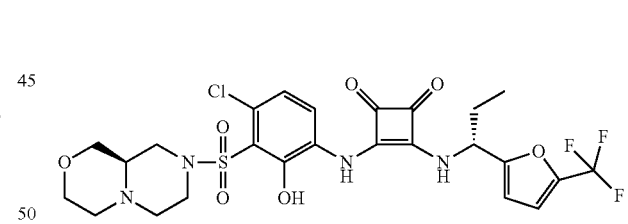

Example 8

Iodoethane (568 μL, 7.03 mmol) is dissolved in dry diethyl ether (11 mL) under an argon atmosphere, cooled to −78° C. and tert-butyl lithium (1.7 M in pentane, 8.27 mmol, 14.06 mmol) is added dropwise with cooling. After 10 minutes the mixture is warmed to room temperature, stirred for 1 hour and then cooled to −70° C. Compound 8-1 (1.88 g, 5.9 mmol) in dry diethyl ether (8 mL) is added dropwise, the mixture is stirred at −70° C. for 90 minutes then hydrochloric acid (1 M, 15 mL) is added. The mixture is warmed to room temperature, the phases separated and the aqueous phase washed with diethyl ether. The aqueous phase is basified with 32% NaOH solution and extracted with diethyl ether. The organic extracts are dried over magnesium sulphate and the solvent removed to give compound 8-2.

Yield: 516 mg
ES mass spectrum: [M+H]$^+$=280
Retention time HPLC: 0.85 min (UPLC method 1)

Compound 7-7 (50 mg, 0.11 mmol) is allowed to react with compound 8-3 in a manner analogous to that described for the preparation of Example 1 to give Example 8.

Yield: 40 mg
ES mass spectrum: [M+H]$^+$=619
Retention time HPLC: 9.96 min (HPLC method 7)
1H NMR (Varian 400 MHz. DMSO-d6; 28° C.) 10.4 (1H, br); 9.40 (1H, s); 8.79 (1H, d); 7.98 (1H, d); 7.18-7.25 (2H, m); 6.65 (1H, d); 5.27 (1H, m); 3.69 (3H, m); 3.49 (2H, m); 3.04 (2H, m); 2.76-2.52 (3H, m); 2.19 (3H, m); 1.94 (2H, m); 0.94 (3H, t).

Synthesis of Example 9

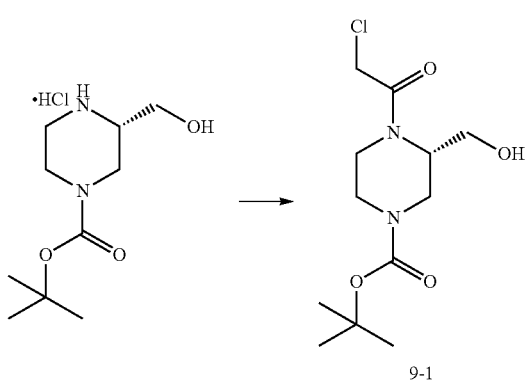 [SMILES: CC(C)(C)OC(=O)N1CCN[C@H](CO)C1 ; Cl ; CC(C)(C)OC(=O)N1CCN(C(=O)CCl)[C@H](CO)C1]

9-1

(S)-4-N-Boc-2-Hydroxymethyl-piperazine hydrochloride (3.98 g, 18.40 mmol) is treated in a manner analogous to that described of compound 7-1 to give compound 9-1.

Yield: 5.4 g
ES mass spectrum: $[M-tBu+H]^+=237$
Retention time HPLC: 0.82 min (UPLC analitica_NH4COOH).

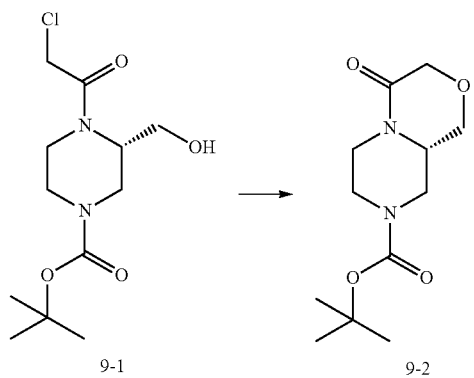 [SMILES: CC(C)(C)OC(=O)N1CCN(C(=O)CCl)[C@H](CO)C1 ; CC(C)(C)OC(=O)N1CCN2C(=O)COC[C@@H]2C1]

9-1  9-2

Compound 9-1 (5.39 g, 18.4 mmol) is treated in a manner analogous to that described for the synthesis of compound 7-2 to give compound 9-2.

Yield: 1100 mg
EI mass spectrum: $[M]^+=256$
Retention time GC: 11.91 min (GCMS method 8).

9-2  9-3

Compound 9-2 (1100 mg, 4.29 mmol) is treated in a manner analogous to that described for the synthesis of compound 7-3 to give compound 9-3.

Yield: 827 mg
ES mass spectrum: $[M+H]^+=157$
Retention time HPLC: 0.25 min (UPLC method 1).

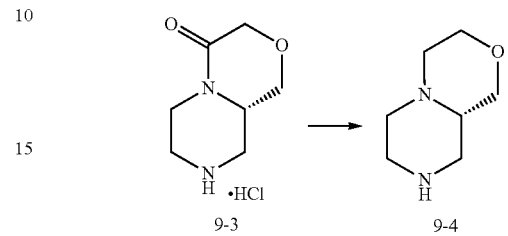

9-3  9-4

Compound 9-3 (827 mg, 4.29 mmol) is treated in a manner analogous to that described for the synthesis of compound 7-4 to give compound 9-4.

Yield: 230 mg
ES mass spectrum: $[M]^+=142$
Retention time GC: 7.35 min (3A.2).

9-4

9-5

Compound 9-4 (90 mg, 0.63 mmol) is treated in a manner analogous to that described for the preparation of Compound 1-1 to give compound 9-5

Yield: 260 mg
ES mass spectrum: $[M+H]^+=414$
Retention time UPLC: 1.14 min (UPLC method 2)

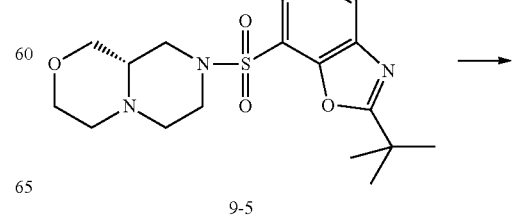

9-5

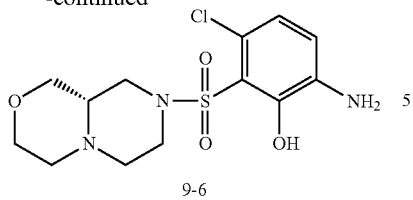

9-6

Compound 9-5 (260 mg, 0.63 mmol) is treated in a manner analogous to that described for the preparation of Compound 1-2 to give compound 9-6.
Yield: 195 mg
ES mass spectrum: [M+H]$^+$=348
Retention time UPLC: 0.88 min (UPLC method 2)

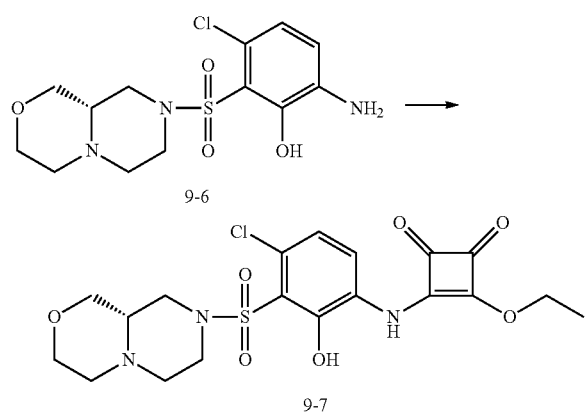

Compound 9-6 (195 mg, 0.56 mmol) is treated in a manner analogous to that described for the preparation of Compound 1-3 to give compound 9-7.
Yield: 120 mg
ES mass spectrum: [M+H]$^+$=472
Retention time UPLC: 0.89 min (UPLC method 2)

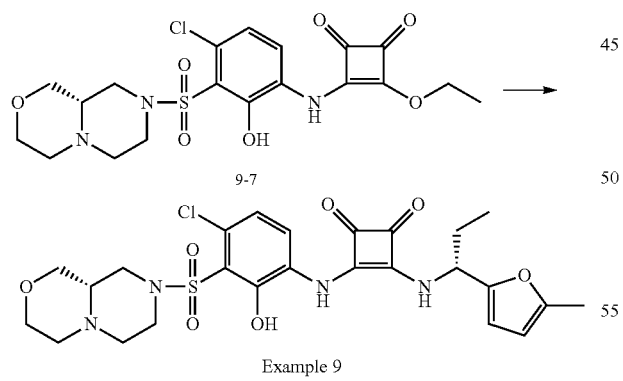

Example 9

Compound 9-7 (60 mg, 0.13 mmol) is treated in a manner analogous to that described for the preparation of Example 2 to give Example 9.
Yield: 56 mg
ES mass spectrum: [M+H]$^+$=565
Retention time HPLC: 9.23 min (HPLC method 7)
1H NMR (Varian Inova 500 MHz. DMSO-d6; 27° C.) 9.41 (1H, s); 8.75 (1H, d); 7.99 (1H, d); 7.18 (1H, br); 6.26 (1H, d); 6.05 (1H, d); 5.13 (1H, m); 3.70 (3H, m); 3.54 (1H, m); 3.47 (1H, m); 3.06 (2H, m); 2.78 (1H, m); 2.65 (1H, m); 2.56 (1H, m); 2.29 (3H, s); 2.17 (3H, m); 1.91 (2H, m); 0.93 (3H, t).

Synthesis of Example 10

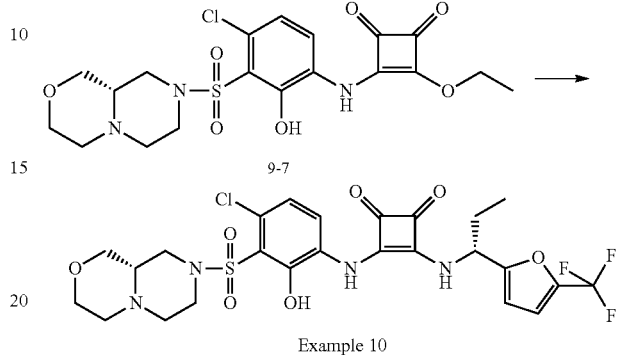

Example 10

Compound 9-7 (60 mg, 0.13 mmol) is allowed to react with compound 8-3 in a manner analogous to that described for the preparation of Example 1 to give Example 10.
Yield: 23 mg
ES mass spectrum: [M+H]$^+$=619
Retention time HPLC: 9.95 min (HPLC method 7)
1H NMR (Varian 400 MHz. DMSO-d6; 28° C.) 10.58 (1H, br); 9.42 (1H, s); 8.78 (1H, d); 7.44 (1H, d), 7.22 (1H, d); 7.14 (1H, m br); 6.66 (1H, d); 5.25 (1H, m); 3.66 (3H, m); 3.48 (2H, m); 2.95 (2H, m); 2.76-2.52 (3H, m); 2.14 (3H, m); 1.90 (2H, m); 0.92 (3H, t).

Synthesis of Example 11

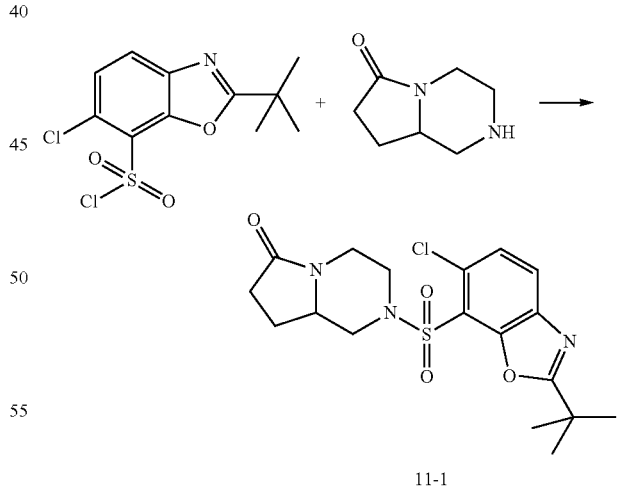

11-1

Hexahydro-pyrrolo[1,2-a]pyrazin-6-one hydrochloride (283 mg, 1.6 mmol) is treated in a manner analogous to that described for the preparation of Compound 1-1 to give Compound 11-1.
Yield: 492 mg
ES mass spectrum: [M+H]$^+$=412
Retention time UPLC: 1.07 min (UPLC method 2)

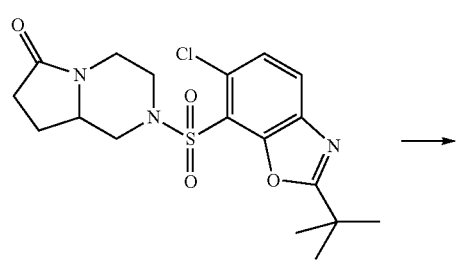

11-1

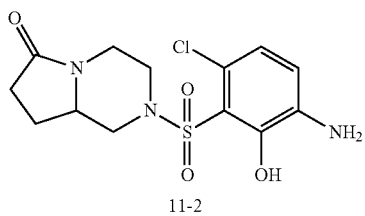

11-2

Compound 11-1 (492 mg, 1.19 mmol) is treated in a manner analogous to that described for the preparation of Compound 1-2 to give Compound 11-2.

Yield: 400 mg

ES mass spectrum: $[M+H]^+=345$

Retention time UPLC: 0.85 min (UPLC method 2)

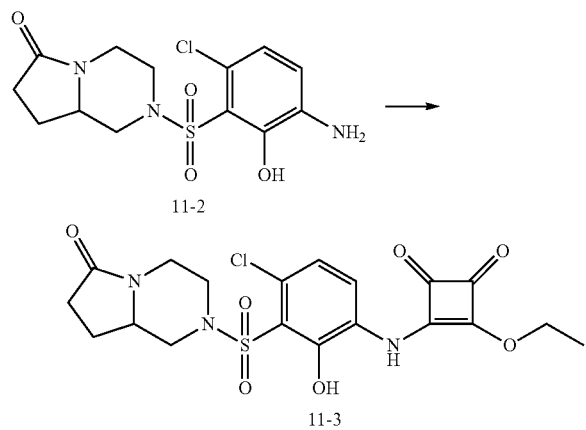

11-2

11-3

Compound 11-2 (400 mg, 1.16 mmol) is treated in a manner analogous to that described for the preparation of Compound 1-3 to give Compound 11-3.

Yield: 207 mg

ES mass spectrum: $[M+H]^+=470$

Retention time HPLC: 9.38 min (HPLC method 7)

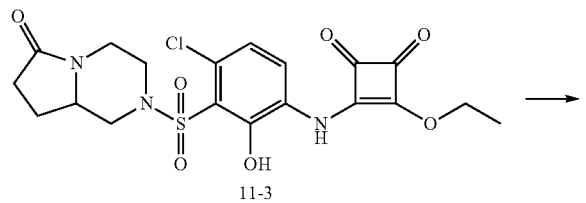

11-3

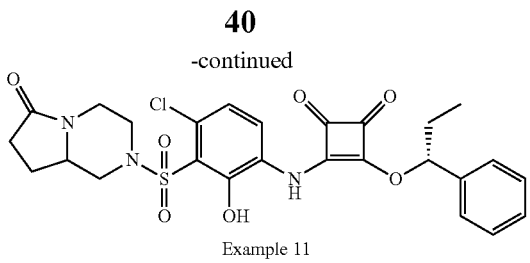

Example 11

Compound 11-3 (40 mg, 0.093 mmol) is treated in a manner analogous to that described for the preparation of Example 1 to give Example 11.

Yield: 26 mg

ES mass spectrum: $[M+H]^+=559$

Retention time HPLC: 8.12 min (HPLC method 6)

1H NMR (Varian Inova 500 MHz. DMSO-d6; 27° C.) 10.4 (1H, s); 9.40 (1H, s); 8.74 (1H, d); 8.00 (1H, d); 7.30-7.40 (5H, m); 7.15 (1H, d); 5.10 (1H, m); 3.84-3.9 (2H, m); 3.74 (1H, m); 3.57 (1H, m); 2.80 (2H, m); 2.69 (1H, m); 2.23 (2H, m); 2.11 (1H, m); 1.93 (2H, m); 1.56 (1H, m); 0.91 (3H, t).

Synthesis of Example 12

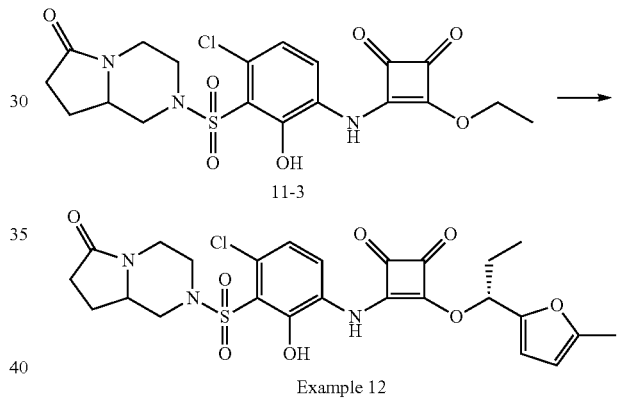

11-3

Example 12

Compound 11-3 (40 mg, 0.09 mmol) is treated in a manner analogous to that described for the preparation of Example 2 to give Example 12.

Yield: 21 mg

ES mass spectrum: $[M+H]^+=563$

Retention time HPLC: 8.05 min (HPLC method 6)

1H NMR (Varian Inova 500 MHz. DMSO-d6; 27° C.) 10.42 (1H, s); 9.41 (1H, s); 8.73 (1H, d); 8.01 (1H, d); 7.19 (1H, br); 6.25 (1H, d); 6.04. (1H, dd); 5.11 (1H, m); 3.88 (2H, m); 3.74 (1H, m); 3.56 (1H, m); 2.81 (2H, m); 2.70 (1H, m); 2.26 (3H, s); 2.25 (2H, m); 2.10 (1H, m); 1.91 (2H, m); 1.56 (1H, m); 0.88 (3H, t).

Synthesis of Example 13

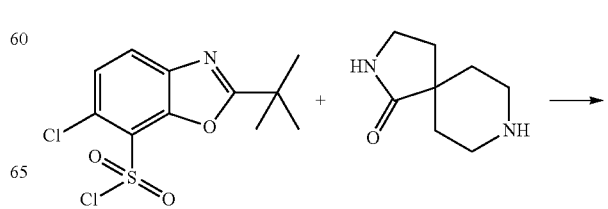

-continued

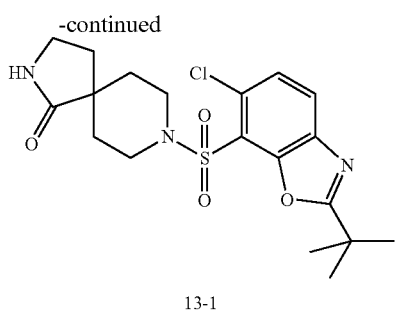

13-1

2,8-Diaza-spiro[4.5]decan-1-one hydrochloride (309 mg, 1.62 mmol) is treated in a manner analogous to that described for the preparation of Compound 1-1 to give compound 13-1.

Yield: 432 mg

ES mass spectrum: [M+H]$^+$=426

Retention time UPLC: 1.04 min (UPLC method 2)

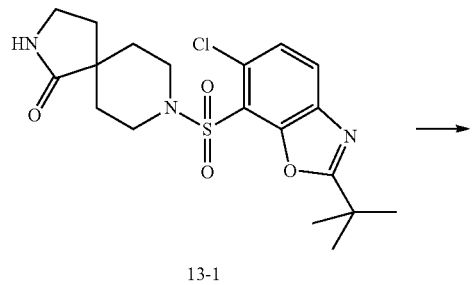

13-1

Compound 13-1 (432 mg, 1.19 mmol) is treated in a manner analogous to that described for the preparation of Compound 1-2 to give compound 13-2.

Yield: 284 mg

ES mass spectrum: [M+H]$^+$=360

Retention time UPLC: 0.79 min (UPLC method 2)

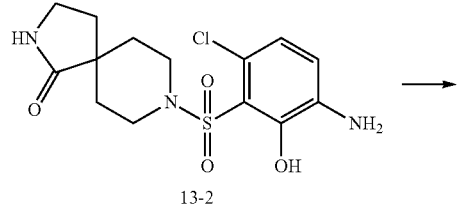

13-2

-continued

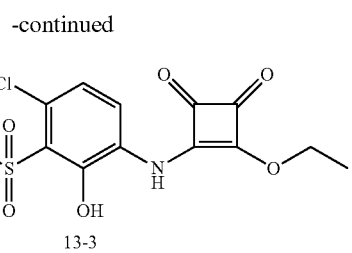

13-3

Compound 13-2 (150 mg, 1.16 mmol) is treated in a manner analogous to that described for the preparation of Compound 1-3 to give compound 13-3.

Yield: 80 mg

ES mass spectrum: [M+H]$^+$=484

Retention time HPLC: 9.51 min (HPLC method 7)

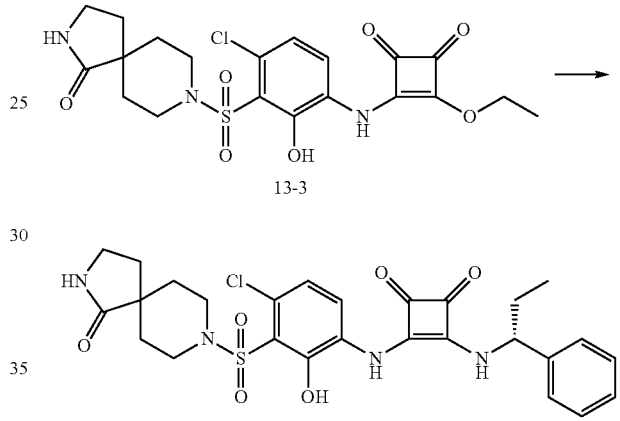

Example 13

Compound 13-3 (45 mg, 0.09 mmol) is treated in a manner analogous to that described for the preparation of Example 1 to give Example 13.

Yield: 23 mg

ES mass spectrum: [M+H]$^+$=573

Retention time HPLC: 11.25 min (HPLC method 7)

1H NMR (Varian Inova 500 MHz. DMSO-d6; 27° C.) 10.5 (1H, br); 9.43 (1H, s); 8.77 (1H, d); 7.99 (1H, d); 7.60 (1H, s); 7.36 (5H, m); 7.15 (1H, br); 5.09 (1H, m); 3.64 (2H, m); 3.15 (2H, m); 3.05 (2H, m); 1.92 (4H, m) 1.67 (2H, m); 1.44 (2H, m); 0.91 (3H, t).

Synthesis of Example 14

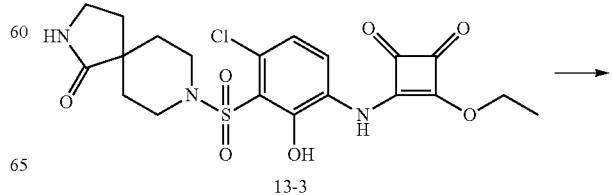

13-3

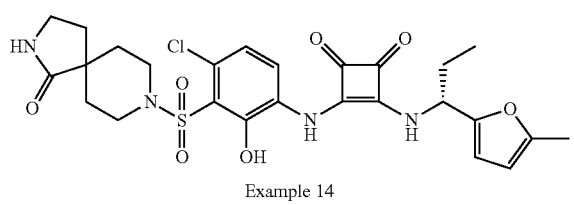

Example 14

Compound 13-3 (25 mg, 0.05 mmol) is treated in a manner analogous to that described for the preparation of Example 2 to give Example 14.

Yield: 21 mg

ES mass spectrum: [M+H]$^+$=577

Retention time HPLC: 11.32 min (HPLC method 7)

1H NMR (Varian 400 MHz. DMSO-d6; 28° C.) 10.5 (1H, br); 9.40 (1H, s); 8.75 (1H, d); 7.97 (1H, br); 7.62 (1H, s); 7.19 (1H, br); 6.24 (1H, s); 6.04 (1H, s); 5.10 (1H, m); 3.65 (2H, m); 3.14 (2H, m); 3.05 (2H, m); 2.26 (3H, s); 1.90 (4H, m); 1.67 (2H, m); 1.43 (2H, m); 0.92 (3H, t).

Synthesis of Example 15

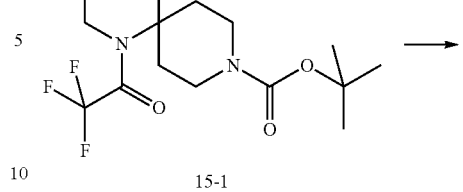

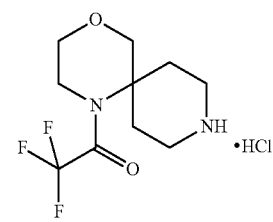

1-Oxa-4,9-diazaspiro[5.5]undecane-9-carboxylic acid tert-butyl ester (600 mg, 2.34 mmol) and pyridine (377 µL, 4.68 mmol) are dissolved in DCM (15 mL) and cooled to 0° C. Trifluoroacetic anhydride (496 µL, 3.51 mmol) is added dropwise and the mixture is stirred at room temperature overnight. The mixture is diluted with DCM, washed with 5% hydrochloric acid solution, 5% NaHCO$_3$ solution and brine, dried and the solvent is removed to give compound 15-1.

Yield: 642 mg

ES mass spectrum: [M+H]$^+$=353

Retention time HPLC: 2.53 min (HPLC method 5)

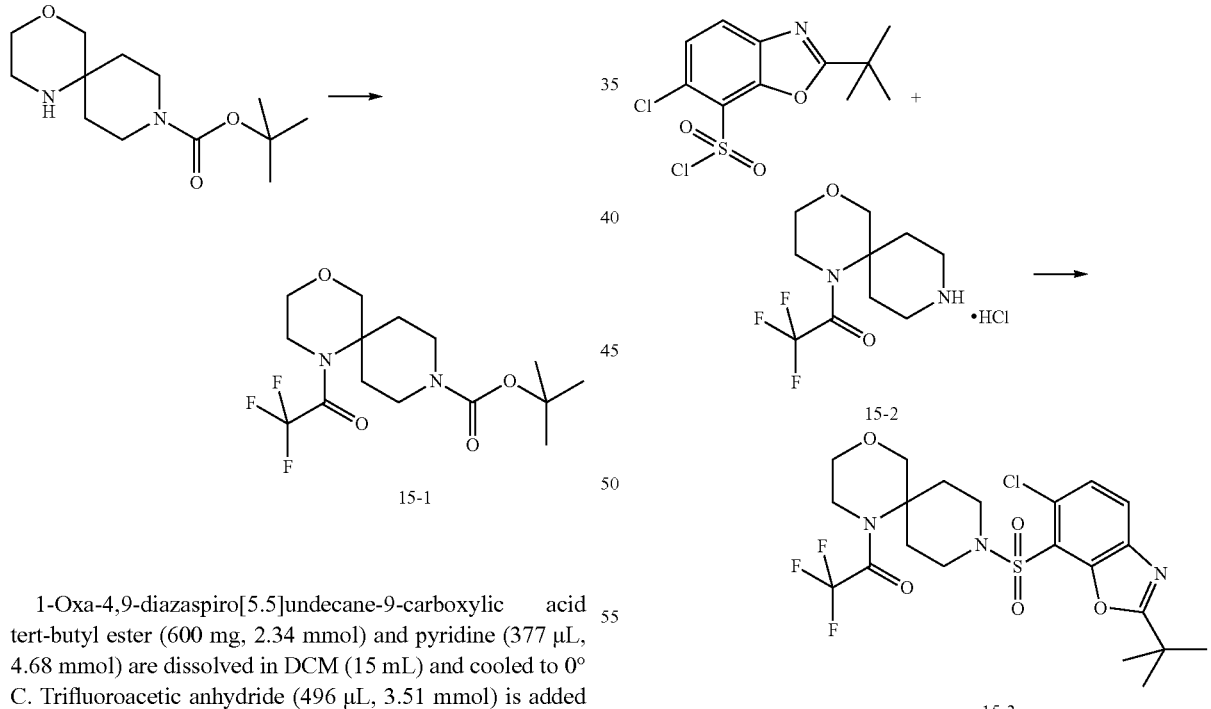

Compound 15-1 (642 mg, 1.73 mmol) is dissolved in dioxane (15 mL) and 4 M hydrogen chloride in dioxane (4.56 mL, 18.22 mmol) is added dropwise. The mixture is stirred overnight and the solvent removed under vacuum to give compound 15-2.

Yield: 470 mg

ES mass spectrum: [M+H]$^+$=253

Retention time HPLC: 0.53 min (HPLC method 5)

Compound 15-2 (470 mg, 1.63 mmol) is treated in a manner analogous to that described for the preparation of Compound 1-1 to give Compound 15-3.

Yield: 802 mg

ES mass spectrum: [M+H]$^+$=523

Retention time HPLC: 3.12 min (HPLC method 5)

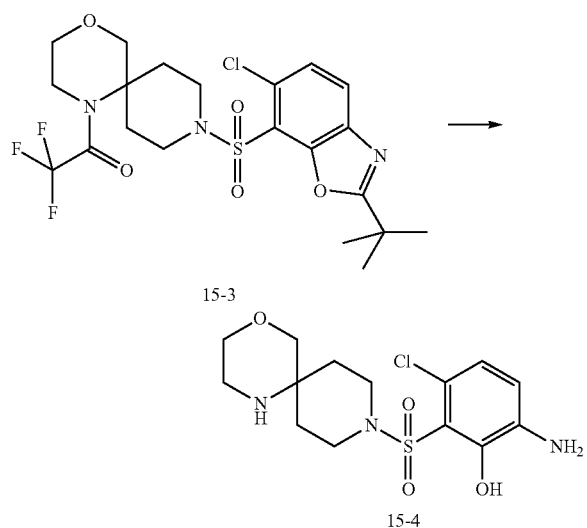

15-3

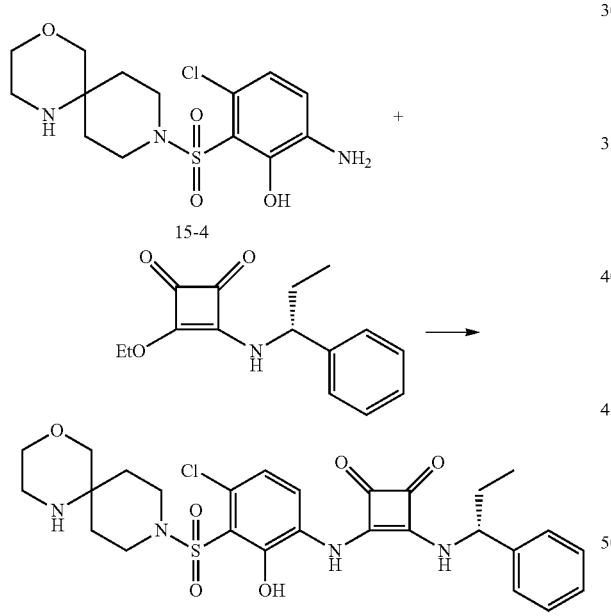

15-4

Compound 15-3 (802 mg, 1.53 mmol) is treated in a manner analogous to that described for the preparation of Compound 1-2 to give Compound 15-4.
Yield: 343 mg
ES mass spectrum: [M+H]$^+$=362
Retention time HPLC: 0.54 min (HPLC method 5)

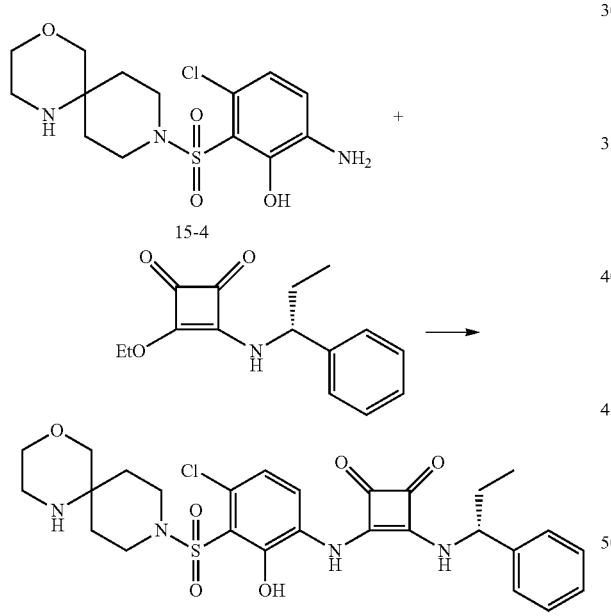

Example 15

Compound 15-4 (37 mg, 0.1 mmol), 3-ethoxy-4-((R)-1-phenyl-propylamino)-cyclobut-3-ene-1,2-dione (40 mg, 0.15 mmol, US2004/147559) and triethylamine (22 mL, 0.15 mmol) are combined in ethanol (4 mL) and heated under reflux for 5 hours. The solvent is removed and the residue purified by semi-preparative reverse phase HPLC to give Example 15.
Yield: 18 mg
ES mass spectrum: [M+H]$^+$=575
Retention time HPLC: 8.23 min (HPLC method 6)
1H NMR (Varian 400 MHz. DMSO-d6; 28° C.) 9.42 (1H, s); 8.76 (1H, d); 7.95 (1H, d); 7.32 (5H, m); 7.08 (2H, br); 5.08 (1H, m); 4.0 (3H, m); 3.73 (4H, m); 3.52 (2H, m); 3.16 (2H, m); 1.90 (4H, m); 1.74 (2H, m); 0.88 (3H, t).

Synthesis of Example 16

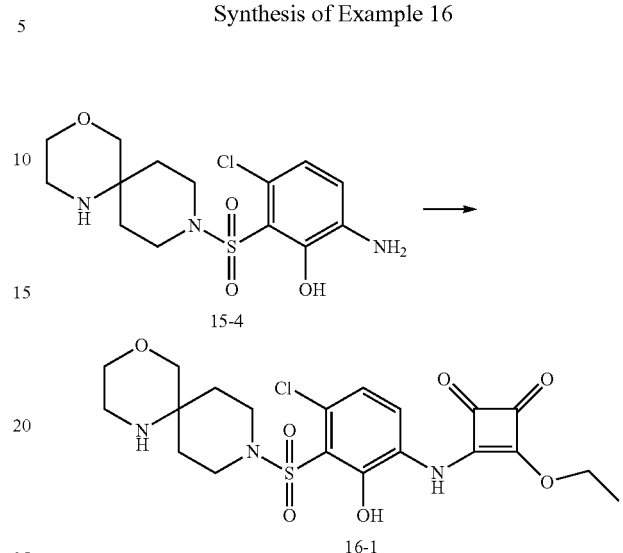

15-4

16-1

Compound 15-4 (110 mg, 0.3 mmol) is treated in a manner analogous to that described for the preparation of Compound 1-3 to give Compound 16-1.
Yield: 97 mg
ES mass spectrum: [M+H]$^+$=486
Retention time HPLC: 6.52 min (HPLC method 6)

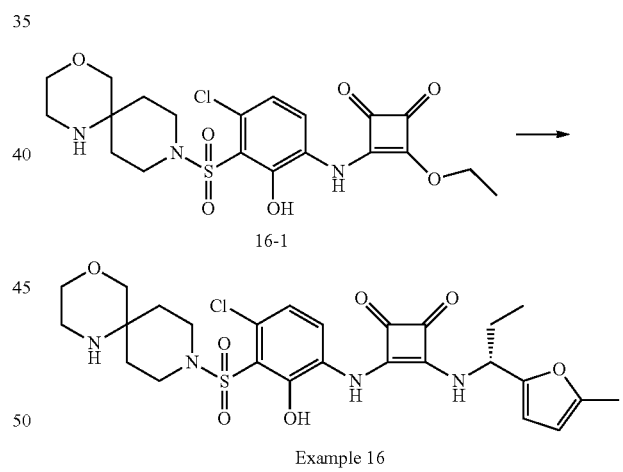

16-1

Example 16

Compound 16-1 (80 mg, 0.16 mmol) is treated in a manner analogous to that described for the preparation of Example 2 to give Example 16.
Yield: 18 mg
ES mass spectrum: [M+H]$^+$=579
Retention time HPLC: 7.50 min (HPLC method 7)
1H NMR (Varian Inova 500 MHz. DMSO-d6; 27° C.) 10.3 (1H, br); 9.41 (1H, s); 9.05 (1H, br), 8.73 (1H, d); 7.98 (1H, d), 7.15 (1H, br); 6.27 (1H, d); 6.06 (1H, d); 5.13 (1H, m); 3.74 (4H, m); 3.53 (2H, m); 3.27 (3H, m); 3.16 (2H, m); 2.27 (3H, s); 1.98 (3H, m); 1.86 (1H, m); 1.78 (2H, m); 0.93 (3H, t).

Synthesis of Example 17

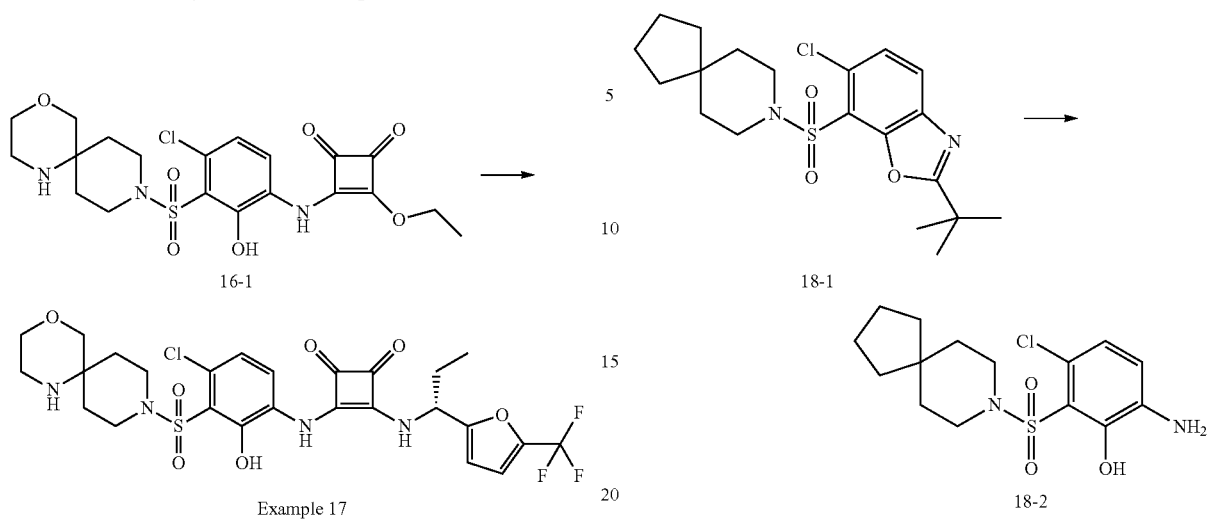

Compound 16-1 (38 mg, 0.08 mmol) is treated with Compound 8-3 in a manner analogous to that described for the preparation of Example 2 to give Example 17.

Yield: 8 mg

ES mass spectrum: [M+H]$^+$=633

Retention time HPLC: 8.65 min (HPLC method 6)

1H NMR (Varian 400 MHz. DMSO-d6; 27° C.) 10.1 (1H, br); 9.42 (1H, s); 8.80 (1H, d); 7.90 (1H, d); 7.22 (1H, d); 6.94 (1H, br); 6.65 (1H, d); 5.28 (1H, m); 3.71 (4H, m); 3.52 (3H, m); 3.15 (4H, m); 1.93 (4H, m), 1.78 (2H, m); 0.91 (3H, t).

Synthesis of Example 18

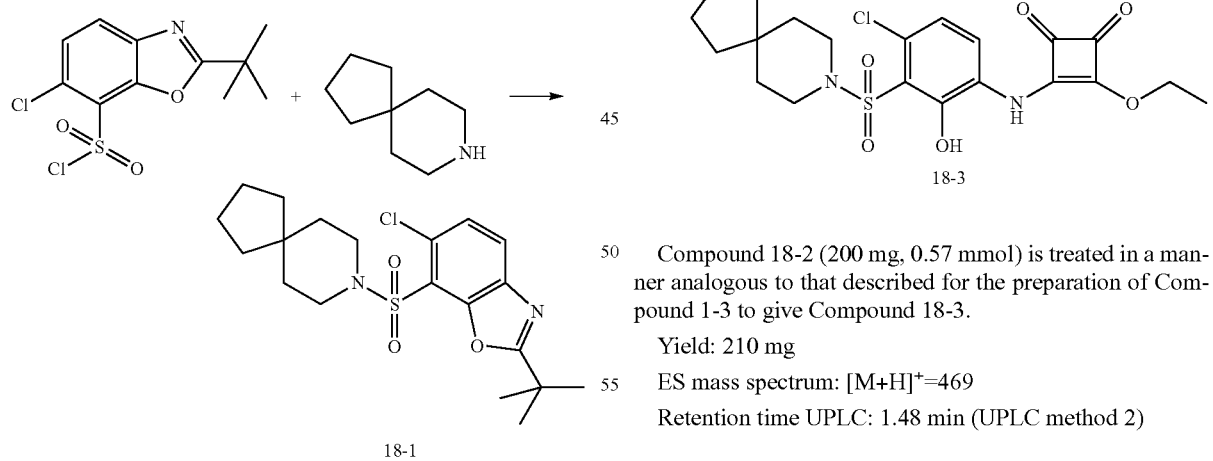

8-Aza-spiro[4.5]decane hydrochloride (140 mg, 0.8 mmol) is treated in a manner analogous to that described for the preparation of Compound 1-1 to give Compound 18-1.

Yield: 233 mg

ES mass spectrum: [M+H]$^+$=411

Retention time UPLC: 0.87 min (UPLC method 3)

Compound 18-1 (233 mg, 0.57 mmol) is treated in a manner analogous to that described for the preparation of Compound 1-2 to give Compound 18-2.

Yield: 200 mg

ES mass spectrum: [M+H]$^+$=345

Retention time UPLC: 1.49 min (UPLC method 2)

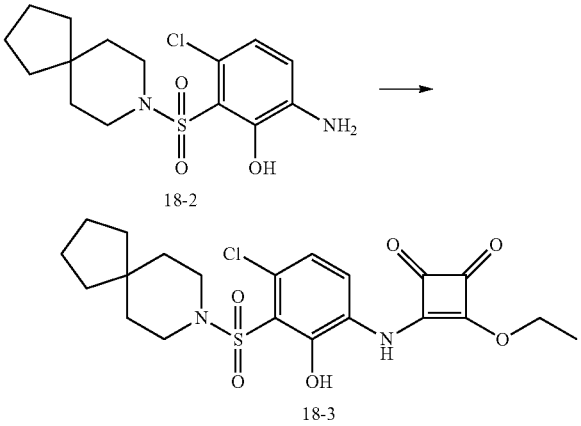

Compound 18-2 (200 mg, 0.57 mmol) is treated in a manner analogous to that described for the preparation of Compound 1-3 to give Compound 18-3.

Yield: 210 mg

ES mass spectrum: [M+H]$^+$=469

Retention time UPLC: 1.48 min (UPLC method 2)

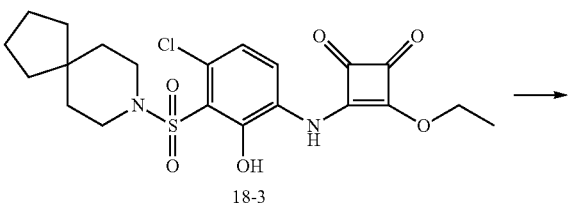

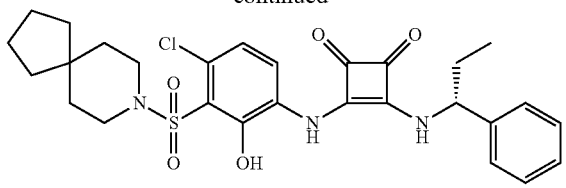

Example 18

Compound 18-3 (70 mg, 0.15 mmol) is treated in a manner analogous to that described for the preparation of Example 1 to give Example 18.

Yield: 2 mg
ES mass spectrum: [M+H]$^+$=558
Retention time HPLC: 11.22 min (HPLC method 7)
1H NMR (Varian Inova 500 MHz. CD3OD; 27° C.) 8.02 (1H, d); 7.21-7.29 (4H, m); 7.20 (1H, m); 6.96 (1H, d); 5.07 (1H, m); 3.33 (4H, m); 1.89 (2H, m); 1.54 (4H, m); 1.44 (4H, m); 1.35 (4H, m); 0.89 (3H, t). 3H not observed.

Synthesis of Example 19

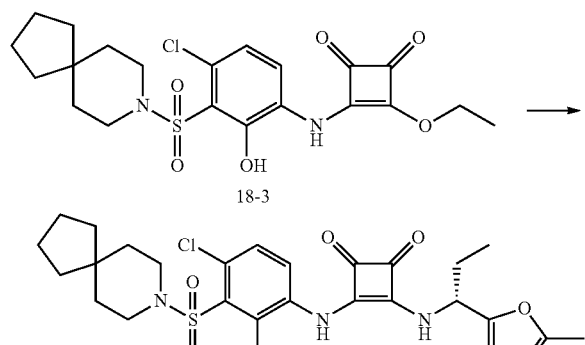

Example 19

Compound 18-3 (70 mg, 0.15 mmol) is treated in a manner analogous to that described for the preparation of Example 2 to give Example 19.

Yield: 2 mg
ES mass spectrum: [M+H]$^+$=562
Retention time HPLC: 11.18 min (HPLC method 7)
1H NMR (Varian Inova 500 MHz. CD3OD 27° C.) 8.13 (1H, d); 7.08 (1H, d); 6.19 (1H, d); 5.96 (1H, d); 5.21 (1H, m); 3.19 (1H, m); 2.26 (3H, s); 2.00 (2H, m); 1.64 (4H, m); 1.54 (4H, m); 1.46 (4H, m); 1.28 (2H, m); 0.99 (3H, t). 3H not observed.

Synthesis of Example 20

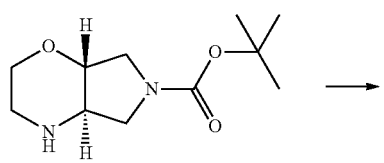

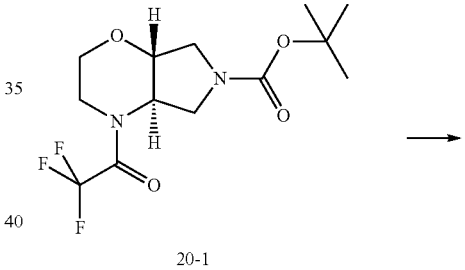

20-1

(4aR,7aR)-Hexahydro-pyrrolo[3,4-b][1,4]oxazine-6-carboxylic acid tert-butyl ester (380 mg, 1.66 mmol) and pyridine (268 µL, 3.33 mmol) are dissolved in DCM (10 mL) and cooled to 0° C. Trifluoroacetic acid (353 µL, 2.5 mmol) is added and the mixture stirred overnight at room temperature. The mixture is diluted with DCM, washed with 5% hydrochloric acid, 5% NaHCO$_3$ solution and brine, dried and the solvent removed to give compound 20-1.

Yield: 495 mg
ES mass spectrum: [M+H-tBu]$^+$=269
Retention time HPLC: 2.34 min (HPLC method 5)

20-1

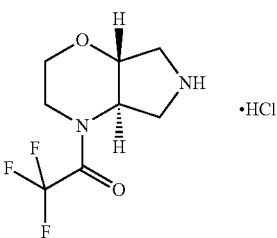

20-2

Compound 20-1 (495 mg, 1.53 mmol) is suspended in dioxane (15 mL) and 4 M hydrogen chloride in dioxane (3.82 mL, 15.26 mmol) is added. The mixture is stirred overnight then the solvent removed under vacuum to give Compound 20-2.

Yield: 347 mg
ES mass spectrum: [M+H]$^+$=225
Retention time HPLC: 0.52 min (HPLC method 5)

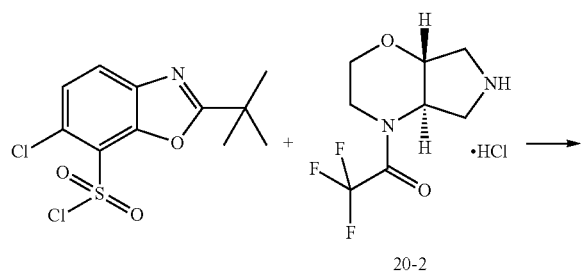

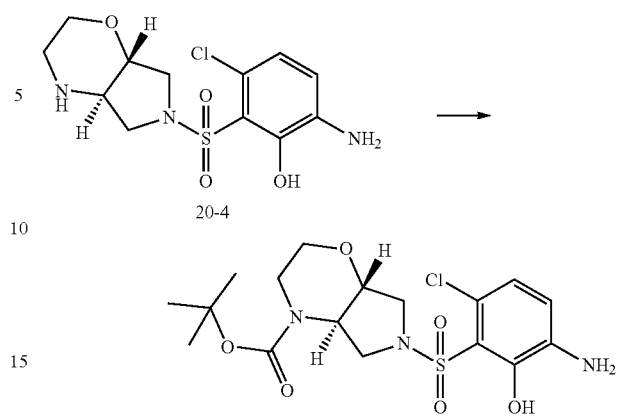

Compound 20-2 (347 mg, 1.29 mmol) is treated in a manner analogous to that described for the preparation of Compound 1-1 to give Compound 20-3.

Yield: 605 mg

ES mass spectrum: [M+H]$^+$=496

Retention time HPLC: 3.03 min (HPLC method 5)

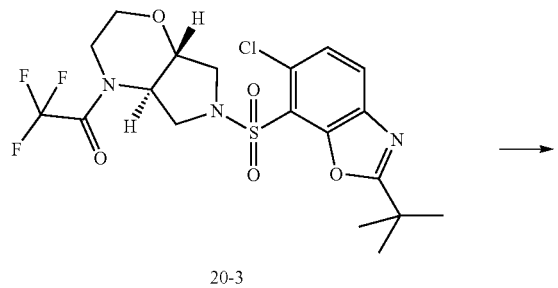

Compound 20-3 (600 mg, 1.13 mmol) is treated in a manner analogous to that described for the preparation of Compound 1-2 to give Compound 20-4.

Yield: 410 mg

ES mass spectrum: [M+H]$^+$=334

Retention time HPLC: 0.53 min (HPLC method 5)

Compound 20-4 (250 mg, 0.75 mmol) and di-tert-butyldicarbonate (163 mg, 0.75 mmol) are suspended in dry THF at 0° C. and stirred for 90 minutes. The mixture is concentrated under vacuum, the residue dissolved in DCM, washed with 5% NaHCO$_3$ solution, dried and the solvent removed to give compound 20-5.

Yield: 320 mg

ES mass spectrum: [M+H]$^+$=434

Retention time HPLC: 12.36 (HPLC method 7)

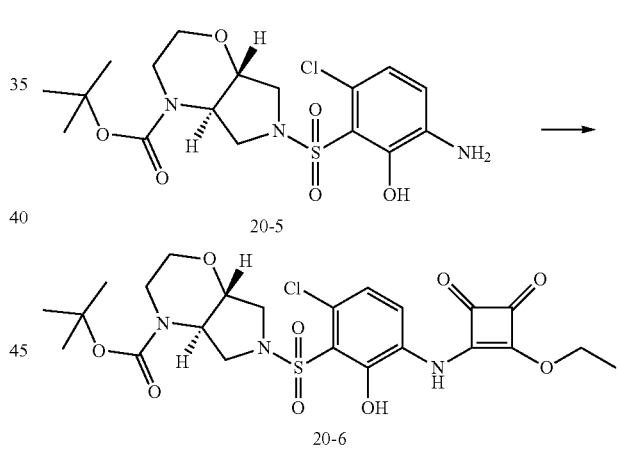

Compound 20-5 (320 mg, 0.72 mmol) is treated in a manner analogous to that described for the preparation of Compound 1-3 to give compound 20-6.

Yield: 300 mg

ES mass spectrum: [M+H]$^+$=580

Retention time HPLC: 12.24 min (HPLC method 7)

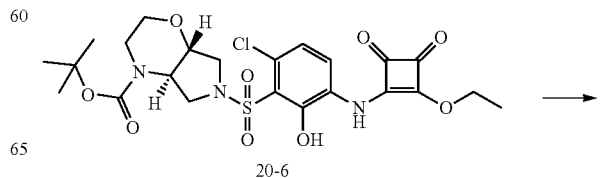

-continued

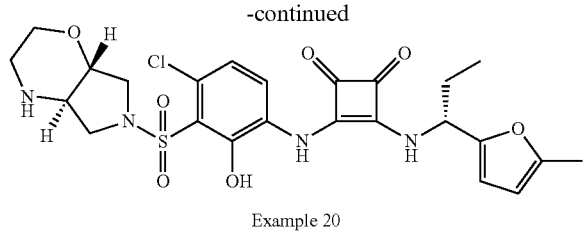

Example 20

Compound 20-6 (90 mg, 0.16 mmol) is suspended in dioxane (4 mL) and 4 M hydrogen chloride in dioxane (0.4 mL, 1.6 mmol) is added at 0° C. The mixture is stirred for 7 hours at room temperature then left in a freezer overnight. NaHCO$_3$ is added until slightly basic, then (R)-1-(5-methyl-furan-2-yl)propylamine (42 mg, 0.3 mmol, Journal of Medicinal Chemistry, 2006, vol. 49, p. 7603-7606) and ethanol (5 mL) are added. The mixture is heated at 65° C. for 6 hours then the solvent removed. The residue is suspended in DCM and washed with water, dried and concentrated under vacuum. The residue is purified by semi-preparative reverse phase HPLC to give Example 20.

Yield: 12 mg

ES mass spectrum: $[M+H]^+=551$

Retention time HPLC: 7.88 min (HPLC method 6)

1H NMR (Varian 400 MHz. DMSO-d6; 28° C.) 9.41 (1H, br); 8.75 (1H, d); 7.80 (1H, d); 6.80 (1H, br); 6.27 (1H, d); 6.07 (1H, d); 5.14 (1H, m) 4.04 (1H, m); 3.90 (2H, m); 3.74 (2H, m); 3.56 (2H, m); 3.12 (4H, m); 2.09 (3H, s); 1.90 (2H, m); 0.91 (3H, t).

EXAMPLES

Other features and advantages of the present invention will become apparent from the following more detailed examples which illustrate, by way of example, the principles of the invention.

Chemotaxis Assay 1, Transfected Cell Line:

This assay measures the inhibition of CXCL1 induced chemotaxis of BAF/3 cells expressing human CXCR2. For each assay point, 100 µL of a 3×10$^6$/mL cell suspension are incubated with 1 µL of test compound diluted in DMSO. The bottom wells of a chemotaxis plate (5 µm pore size, Neuro-probe) is filled with 305 µL of chemotaxis buffer (RPMI 1640 medium (phenol red free), containing 2% fetal calf serum) and 3 nM CXCL1. The 5 µm pore membrane is applied onto the chemotaxis plate and 80 µL of the cell suspension is cautiously pipetted onto the membrane. The lid is put on the chemotaxis plate and the plate is incubated for 4 hours in an incubator (37° C., 5% CO2). For quantification of migrated cells, the cell suspension and the lid are removed and 100 µL from the bottom chamber are transferred to an Opti plate 96 (Perkin Elmer). 100 µL of substrate solution (provided by Cell Titer Glo kit, Promega) are added. This method uses the measurement of ATP present in metabolically active cells. After 10 min incubation at room temperature the plate is measured at Luminoscan for quantification of ATP-dependent generation of oxyluciferin. IC50s of the tested compound are calculated by non-linear regression and using a sigmoidal dose-response curve as fitting algorithm (provided by GraphPadPrism). Determination of a bottom value is performed by quantification of migration of buffer treated cells, migrating towards buffer only. Determination of a top value is performed by quantification of migration of buffer treated cells, migrating towards CXCL1.

Chemotaxis Assay 2, Primary Human PMN (Polymorph Nuclear Cells) from Healthy Donors:

This assay measures the inhibition of CXCL1 induced chemotaxis of primary human PMN cells isolated from healthy donors. Neutrophils, the major type of human PMN cells express both CXCR1 and CXCR2. CXCL1 specifically binds to CXCR2, not CXCR1 and therefore, upon stimulation with CXCL1 measurements are focused on CXCR2. For the isolation of PMN cells, human whole blood is mixed with DPBS and ACD buffer (38 mM citric acid, 75 mM tri-sodium citrate, 121 mM glucose) to prevent coagulation. Blood, DPBS and ACD buffer are mixed at a ratio of 4:1:1. For separation of PMN cells from mononuclear cells, the anti-coagulated blood is layered over 18-20 mL Ficoll (Ficoll-Paqu™ Plus) and centrifuged for 30 min at 300×g, without brake. Supernatant containing mononuclear cells is discarded. Pellet contains PMN cells and erythrocytes. For lysis of erythrocytes, the pellet is suspended with 30 mL of ammonium hydroxide buffer (155 mM NH$_4$Cl, 10 mM KHCO$_3$, 0.1 mM EDTA, pH 5.0) and incubated for 8 minutes on ice. After centrifugation (5 minutes at 300×g), supernatant is discarded and the pellet is treated a second time with ammonium hydroxide buffer, incubated for 8 minutes on ice. After centrifugation (5 minutes at 300×g) supernatant is discarded and the pellet containing the PMN in suspended in HBSS containing 0.1% BSA. Cell number is adjusted to 2.5×10$^6$/ml. 100 µL cell suspension is incubated with 1 µL compound dissolved in DMSO for 20 minutes at room temperature. The bottom wells of a 5 µm pore chemotaxis plate (Neuro-Probe) are filled with either 305 µL HBSS buffer (negative control) of HBSS buffer containing 10 nM CXCL1. The membrane is applied onto the chemotaxis plate and 80 µl of the cell suspension is cautiously pipetted onto the membrane. The lid is put on the chemotaxis plate and the plate is incubated for 1 hour in an incubator (37° C., 5% CO2). For quantification of migrated cells, the cell suspension and the lid are removed and 100 µl from the bottom chamber are transferred to an Opti plate 96 (Perkin Elmer). 100 µl of substrate solution (provided by Cell Titer Glo kit, Promega) are added. After 10 min incubation at room temperature the plate is measured at Luminoscan. IC50s of the tested compound are calculated by non-linear regression and using a sigmoidal dose-response curve as fitting algorithm (provided by GraphPadPrism). Determination of a bottom value was performed by quantification of migration of buffer treated cells, migrating towards buffer only. Determination of a top value was performed by quantification of migration of buffer treated cells, migrating towards CXCL1.

The above mentioned pharmacokinetic properties are measured using methods similar to those described in E. H. Kerns, D. Li: Drug-like Properties: Concepts, Structure, Design and Methods: from ADME to Toxicity Optimization. Academic Press 2008, Burlington, Mass., USA. Chapter 19: Pharmacokinetics, pp 228-241.

All of the referenced examples have been found to have an activity in the above described chemotaxis assay 1 as reported below.

| Example | IC$_{50}$ (nM) |
|---------|----------------|
| 1       | 0.7            |
| 2       | 0.9            |
| 3       | 5.1            |
| 4       | 0.6            |
| 5       | 6.8            |

-continued

| Example | IC$_{50}$ (nM) |
|---|---|
| 6 | 37.8 |
| 7 | 4.9 |
| 8 | 56.6 |
| 9 | 13.4 |
| 10 | 64.8 |
| 11 | 2.6 |
| 12 | 14.4 |
| 13 | 22.6 |
| 14 | 47.1 |
| 15 | 33.8 |
| 16 | 8.7 |
| 17 | 54.4 |
| 18 | 149.0 |
| 19 | 11.6 |
| 20 | 58.6 |

Combinations

The compounds of formula 1 may be used on their own or in conjunction with other active substances of formula 1 according to the invention. If desired the compounds of formula 1 may also be used in combination with other pharmacologically active substances. It is preferable to use for this purpose active substances selected for example from among β2-adrenoceptor-agonists (short and long-acting betamimetics), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, statins, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK (spleen tyrosine kinase-inhibitors), ZAP-70, FYN, BTK or ITK, inhibitors of MAP kinases as for example p38, ERK1, ERK2, JNK1, JNK2, JNK3 or SAP, inhibitors of the NF-kappaB signalling pathway as for example IKK2 kinase inhibitors, iNOS inhibitors (inducible nitric oxide synthase-inhibitors), MRP4 inhibitors, leukotriene antagonists, leukotriene biosynthese inhibitors as for example 5-Lipoxygenase (5-LO) inhibitors, cPLA2 inhibitors, Leukotriene A4 Hydrolase inhibitors or FLAP inhibitors, non-steroidal antiinflammatory drugs (NSAIDs) including COX-2 inhibitors, CRTH2 antagonists, DP1-receptor modulators, Thromboxane receptor antagonists, CCR1 antagonists, CCR2 antagonists, CCR4 antagonists, CCR5 antagonists, CCR6 antagonists, CCR7 antagonists, CCR8 antagonists, CCR9 antagonists, CCR10 antagonists, CCR11 antagonists, CXCR1 antagonists, CXCR2 antagonists, CXCR3 antagonists, CXCR4 antagonists, CXCR5 antagonists, CXCR6 antagonists, CX3CR1 antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic rezeptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Melanocortin receptor (MC1R, MC2R, MC3R, MC4R, MC5R) modulators, CGRP antagonists, Endothelin antagonists, Somatostatin receptor agonists, TNFalpha antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds agianst swelling of the airways, compounds against cough, antiviral drugs, opiate receptor agonists, cannabionoid agonists, sodium channel blockers, N-type calcium channel blockers, serotonergic and noradrenergic modulators, proton pump inhibitors, local anesthetics, VR1 agonists and antagonists, Nicotinic acetylcholine receptor agonists, P2X3 receptor antagonists, NGF agonists and antagonists, NMDA antagonist, potassium channel modulators, GABA modulators, serotonergic and noradrenergic modulators, anti-migraine drugs. The invention also encompasses combinations of three active substances, each selected from one of the above-mentioned categories of compounds. Said list is not considered to have a limiting character.

The compounds of formula 1 may be used on their own or in conjunction with other active substances of formula 1 according to the invention. If desired the compounds of formula 1 may also be used in combination with other pharmacologically active substances. It is preferable to use for this purpose active substances selected for example from among β2-adrenoceptor-agonists (short and long-acting betamimetics), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, statins, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK (spleen tyrosine kinase-inhibitors), ZAP-70, FYN, BTK or ITK, inhibitors of MAP kinases as for example p38, ERK1, ERK2, JNK1, JNK2, JNK3 or SAP, inhibitors of the NF-kappaB signalling pathway as for example IKK2 kinase inhibitors, iNOS inhibitors (inducible nitric oxide synthase-inhibitors), MRP4 inhibitors, leukotriene antagonists, leukotriene biosynthese inhibitors as for example 5-Lipoxygenase (5-LO) inhibitors, cPLA2 inhibitors, Leukotriene A4 Hydrolase inhibitors or FLAP inhibitors, non-steroidal antiinflammatory drugs (NSAIDs) including COX-2 inhibitors, CRTH2 antagonists, DP1-receptor modulators, Thromboxane receptor antagonists, CCR1 antagonists, CCR4 antagonists, CCR5 antagonists, CCR6 antagonists, CCR7 antagonists, CCR8 antagonists, CCR9 antagonists, CCR10 antagonists, CCR11 antagonists, CXCR1 antagonists, CXCR2 antagonists, CXCR3 antagonists, CXCR4 antagonists, CXCR5 antagonists, CXCR6 antagonists, CX3CR1 antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic rezeptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Melanocortin receptor (MC1R, MC2R, MC3R, MC4R, MC5R) modulators, CGRP antagonists, Endothelin antagonists, TNFalpha antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds agianst swelling of the airways, compounds against cough, antiviral drugs, opiate receptor agonists, cannabionoid agonists, sodium channel blockers, N-type calcium channel blockers, serotonergic and noradrenergic modulators, proton pump inhibitors, local anesthetics, VR1 agonists and antagonists, Nicotinic acetylcholine receptor agonists, P2X3 receptor antagonists, NGF agonists and antagonists, NMDA antagonist, potassium channel modulators, GABA modulators, serotonergic and noradrenergic modulators, anti-migraine drugs. The invention also encompasses combinations of three active substances, each selected from one of the above-mentioned categories of compounds. Said list is not considered to have a limiting character.

Examples of preferred betamimetics which may be mentioned include Albuterole, Arformoterole, Bambuterole, Bitolterole, Broxaterole, Carbuterole, Clenbuterole, Fenoterole, Formoterole, Hexoprenaline, Ibuterole, Isoetharine, Isoprenaline, Levosalbutamole, Mabuterole, Meluadrine, Metaproterenole, Milveterol, Orciprenaline, Pirbuterole, Procaterole, Reproterole, Rimiterole, Ritodrine, Salmefamole, Salmeterole, Soterenole, Sulphonterole, Terbutaline, Tiaramide, Tolubuterole, Zinterole, Nolomirole, and 1-(2-chloro-4-hydroxyphenyl)-t-butylaminoethanole, (−)-2-[7(S)-[2(R)-Hydroxy-2-(4-hydroxyphenyl)-ethylamino]-5,6,7,8-tetrahydro-2-naphthyloxy]-N,N-dimethylacetamide hydrochloride monohydrate, 3-(4-{6-[2-Hydroxy-2-(4-hydroxy-3-hydroxymethyl-phenyl)-ethylamino]-hexyloxy}-butyl)-benzyl-sulfonamide 5-[2-(5,6-Diethyl-indan-2-ylamino)-1-hydroxy-ethyl]-8-hydroxy-1H-quinoline-2-one 4-Hydroxy-7-[2-{[2-{[3-(2-phenylethoxy)propyl]sulphonyl}ethyl]-amino}ethyl]-2(3H)-benzothiazolone 1-(2-Fluoro-4-hydroxyphenyl)-2-[4-(1-benzimidazolyl)-2-methyl-2-butylamino]ethanole 1-[3-(4-Methoxybenzyl-amino)-4-hydroxyphenyl]-2-[4-(1-benzimidazolyl)-2-methyl-2-butylamino]ethanole 1-[2H-5-hydroxy-3-oxo-4H-1,4-benzoxazin-8-yl]-2-[3-(4-N,N-dimethylaminophenyl)-2-methyl-2-propylamino]ethanole 1-[2H-5-hydroxy-3-oxo-4H-1,4-benzoxazin-8-yl]-2-[3-(4-methoxyphenyl)-2-methyl-2-propylamino]ethanole 1-[2H-5-hydroxy-3-oxo-4H-1,4-benzoxazin-8-yl]-2-[3-(4-n-butyloxyphenyl)-2-methyl-2-propylamino]ethanole 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanole 5-Hydroxy-8-(1-hydroxy-2-isopropylaminobutyl)-2H-1,4-benzoxazin-3-(4H)-one 1-(4-Amino-3-chloro-5-trifluormethylphenyl)-2-tert.-butylamino)ethanole 6-Hydroxy-8-{1-hydroxy-2-[2-(4-methoxy-phenyl)-1,1-dimethyl-ethylamino]-ethyl}-4H-benzo[1,4]oxazin-3-one 6-Hydroxy-8-{1-hydroxy-2-[2-(4-phenoxy-acetic acid ethylester)-1,1-dimethyl-ethylamino]-ethyl}-4H-benzo[1,4]oxazin-3-one 6-Hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-Dimethyl-2-(2,4,6-trimethylphenyl)-ethylamino]-1-hydroxy-ethyl}-6-hydroxy-4H-benzo[1,4]oxazin-3-one 6-Hydroxy-8-{1-hydroxy-2-[2-(4-hydroxy-phenyl)-1,1-dimethyl-ethylamino]-ethyl}-4H-benzo[1,4]oxazin-3-one 6-Hydroxy-8-{1-hydroxy-2-[2-(4-isopropyl-phenyl)-1,1-dimethyl-ethylamino]-ethyl}-4H-benzo[1,4]oxazin-3-one 8-{2-[2-(4-Ethyl-phenyl)-1,1-dimethyl-ethylamino]-1-hydroxy-ethyl}-6-hydroxy-4H-benzo[1,4]oxazin-3-one 8-{2-[2-(4-Ethoxy-phenyl)-1,1-dimethyl-ethylamino]-1-hydroxy-ethyl}-6-hydroxy-4H-benzo[1,4]oxazin-3-one 4-(4-{2-[2-Hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-Difluor-phenyl)-1,1-dimethyl-ethylamino]-1-hydroxy-ethyl}-6-hydroxy-4H-benzo[1,4]oxazin-3-one 1-(4-Ethoxy-carbonylamino-3-cyano-5-fluorophenyl)-2-(tert.-butylamino)ethanole N-[2-Hydroxy-5-(1-hydroxy-2-{2-[4-(2-hydroxy-2-phenyl-ethylamino)-phenyl]-ethylamino}-ethyl)-phenyl]-formamide 8-Hydroxy-5-(1-hydroxy-2-{2-[4-(6-methoxy-biphenyl-3-ylamino)-phenyl]-ethylamino}-ethyl)-1H-quinolin-2-one 8-Hydroxy-5-[1-hydroxy-2-(6-phenethylamino-hexylamino)-ethyl]-1H-quinolin-2-one 5-[2-(2-{4-[4-(2-Amino-2-methyl-propoxy)-phenylamino]-phenyl}-ethylamino)-1-hydroxy-ethyl]-8-hydroxy-1H-quinolin-2-one

[3-(4-{6-[2-Hydroxy-2-(4-hydroxy-3-hydroxymethyl-phenyl)-ethylamino]-hexyloxy}-butyl)-5-methyl-phenyl]-urea 4-(2-{6-[2-(2,6-Dichloro-benzyloxy)-ethoxy]-hexylamino}-1-hydroxy-ethyl)-2-hydroxymethyl-phenole 3-(4-{6-[2-Hydroxy-2-(4-hydroxy-3-hydroxymethyl-phenyl)-ethylamino]-hexyloxy}-butyl)-benzenesulfonamide 3-(3-{7-[2-Hydroxy-2-(4-hydroxy-3-hydroxymethyl-phenyl)-ethylamino]-heptyloxy}-propyl)-benzenesulfonamide 4-(2-{6-[4-(3-Cyclopentanesulfonyl-phenyl)-butoxy]-hexylamino}-1-hydroxy-ethyl)-2-hydroxymethyl-phenole N-Adamantan-2-yl-2-(3-{2-[2-hydroxy-2-(4-hydroxy-3-hydroxymethyl-phenyl)-ethylamino]-propyl}-phenyl)-acetamide (R,S)-4-(2-{[6-(2,2-Difluoro-4-phenylbutoxy)hexyl]amino}-1-hydroxy-ethyl)-2-(hydroxymethyl)phenole (R,S)-4-(2-{[6-(2,2-Difluoro-2-phenylethoxy)hexyl]amino}-1-hydroxy-ethyl)-2-(hydroxymethyl)phenole (R,S)-4-(2-{[4,4-Difluoro-6-(4-phenylbutoxy)hexyl]amino}-1-hydroxy-ethyl)-2-(hydroxymethyl)phenole (R,S)-4-(2-{[6-(4,4-Difluoro-4-phenylbutoxy)hexyl]amino}-1-hydroxy-ethyl)-2-(hydroxymethyl)phenole (R,S)-5-(2-{[6-(2,2-Difluoro-2-phenylethoxy)hexyl]amino}-1-hydroxy-ethyl)-8-hydroxyquinolin-2(1H)-one (R,S)-2-({6-[2,2-Difluoro-2-(3-methylphenyl)ethoxy]hexyl}amino)-1-hydroxyethyl]-2-(hydroxymethyl)phenole 4-(1R)-2-{[6-(2,2-Difluoro-2-phenylethoxy)hexyl]amino}-1-hydroxyethyl)-2-(hydroxymethyl)phenol (R,S)-2-(Hydroxymethyl)-4-(1-hydroxy-2-{[4,4,5I5-tetrafluoro-6-(3-phenylpropoxy)-hexyl]amino}ethyl)phenole (R,S)-5-(2-{[6-(2,2-Difluoro-2-phenylethoxy)hexyl]amino}-1-hydroxy-ethyl)-2-hydroxyphenyl]formamide (R,S)-4-[2-({6-[2-(3-Bromophenyl)-2,2-difluoroethoxy]hexyl}amino)-1-hydroxyethyl]-2-(hydroxymethyl)phenole (R,S)—N-[3-(1,1-Difluoro-2-{[6-({2-hydroxy-2-[4-hydroxy-3-(hydroxymethyl)phenyl]-ethyl}amino)hexyl]oxy}ethyl)phenyl]urea 3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidine-2,4-dione (R,S)-4-[2-({6-[2,2-difluoro-2-(3-methoxyphenyl)ethoxy]hexyl}amino)-1-hydroxyethyl]-2-(hydroxymethyl)phenole 5-((1R)-2-{[6-(2,2-difluoro-2-phenylethoxy)hexyl]amino}-1-hydroxyethyl)-8-hydroxyquinolin-2(1H)-one 4-((1R)-2-{[4,4-Difluoro-6-(4-phenylbutoxy)hexyl]amino}-1-hydroxy-ethyl)-2-(hydroxymethyl)phenole (R,S)-4-(2-{[6-(3,3-Difluoro-3-phenylpropoxy)hexyl]amino}-1-hydroxy-ethyl)-2-(hydroxymethyl)phenole (R,S)-(2-{[6-(2,2-Difluoro-2-phenylethoxy)-4,4-difluoro-hexyl]amino}-1-hydroxyethyl)-2-(hydroxymethyl)phenole (R,S)-4-(2-{[6-(2,2-difluoro-3-phenylpropoxy)hexyl]amino}-1-hydroxy ethyl)-2-(hydroxymethyl)phenole 3-[2-(3-Chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide 7-[2-(2-{3-[2-(2-Chloro-phenyl)-ethylamino]-propylsulfanyl}-ethylamino)-1-hydroxy-ethyl]-4-hydroxy-3H-benzothiazol-2-one and 7-[(1R)-2-(2-{3-[2-(2-Chloro-phenyl)-ethylamino]-propylsulfanyl}-ethylamino)-1-hydroxy-ethyl]-4-hydroxy-3H-benzothiazol-2-one optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred anticholinergics which may be mentioned include Tiotropium salts, preferred the bromide salt, Oxitropium salts, preferred the bromide salt, Flutropium salts, preferred the bromide salt, Ipratropium salts, preferred the bromide salt, Aclidinium salts, preferred the bromide salt, Glycopyrronium salts, preferred the bromide salt, Trospium salts, preferred the chloride salt, Tolterodin. From the above mentioned salts the pharmacologically active part is the cation, possible anions are chloride, bromide, iodide, sulfate, phosphate, methansulfonate, nitrate, maleate, acetate, citrate, fumarate, tartrate, oxalate, succinate, benzoate or p-toluenesulfonate. Further examples of preferred anticholinergics are selected from among 2,2-Diphenylpropionic acid tropenole ester-methobromide
2,2-Diphenylpropionic acid scopine ester-methobromide
2-Fluor-2,2-Diphenylacetic acid scopine ester-methobromide
2-Fluor-2,2-Diphenylacetic acid tropenole ester-methobromide
3,3',4,4'-Tetrafluorbenzil acid tropenole ester-methobromide
3,3',4,4'-Tetrafluorbenzil acid scopine ester-methobromide
4,4'-Difluorbenzil acid tropenole ester-methobromide
4,4'-Difluorbenzil acid scopine ester-methobromide
3,3'-Difluorbenzil acid tropenole ester-methobromide
3,3'-Difluorbenzil acid scopine ester-methobromide
9-Hydroxy-fluorene-9-carbon acid tropenole ester-methobromide
9-Fluor-fluorene-9-carbon acid tropenole ester-methobromide
9-Hydroxy-fluorene-9-carbon acid scopine ester-methobromide
9-Fluor-fluorene-9-carbon acid scopine ester methobromide
9-Methyl-fluorene-9-carbon acid tropenole estermethobromide
9-Methyl-fluorene-9-carbon acid scopine estermethobromide
Benzil acid cyclopropyl tropine ester-methobromide
2,2-Diphenylpropionic acid cyclopropyl tropine ester-methobromide
9-Hydroxy-xanthene-9-carbon acid cyclopropyl tropine ester-methobromide
9-Methyl-fluorene-9-carbon acid cyclopropyl tropine ester-methobromide
9-Methyl-xanthene-9-carbon acid cyclopropyl tropine ester-methobromide
9-Hydroxy-fluorene-9-carbon acid cyclopropyl tropine ester-methobromide
4,4'-Difluorbenzil acid methylester cyclopropyl tropine ester-methobromide
9-Hydroxy-xanthene-9-carbon acid tropenole ester-methobromide
9-Hydroxy-xanthene-9-carbon acid scopine ester methobromide
9-Methyl-xanthene-9-carbon acid tropenole ester-methobromide
9-Methyl-xanthene-9-carbon acid scopine estermethobromide
9-Ethyl-xanthene-9-carbon acid tropenole ester methobromide
9-Difluormethyl-xanthene-9-carbon acid tropenole ester-methobromide
9-Hydroxymethyl-xanthene-9-carbon acid scopine ester-methobromide.

Examples of preferred corticosteroids which may be mentioned include Beclomethasone, Betamethasone, Budesonide, Butixocorte, Ciclesonide, Deflazacorte, Dexamethasone, Etiprednole, Flunisolide, Fluticasone, Loteprednole, Mometasone, Prednisolone, Prednisone, Rofleponide, Triamcinolone, Tepredane, and {20R-16α,17α-[butylidenebis(oxy)]-6α,9α-difluoro-11β-hydroxy-17β-(methylthio)androsta-4-en-3-one}, 9-fluoro-11beta,17,21-trihydroxy-16alpha-methylpregna-1,4-diene-3,20-dione 21-cyclohexanecarboxylate 17-cyclopropanecarboxylate, 16,17-butylidene dioxy-6,9-difluoro-11-hydroxy-17-(methylthio)androst-4-en-3-one Flunisolide-21-[4'-(nitrooxymethyl)benzoate]

6,9-Difluoro-17-[(2-furanylcarbonyl)oxy]-11-hydroxy-16-methyl-3-oxo-androsta-1,4-dien-17-carbothion acid (S)-fluoromethylester, 6,9-Difluoro-11-hydroxy-16-methyl-3-oxo-17-propionyloxy-androsta-1,4-dien-17-carbothion acid (S)-(2-oxo-tetrahydro-furan-3S-yl)ester, and 6α,9α-difluoro-11β-hydroxy-16α-methyl-3-oxo-17α-(2,2,3,3-tertamethylcyclopropylcarbonyl)oxy-androsta-1,4-diene-17β-carboxylic acid cyanomethyl ester optionally in racemic form, as enantiomers, diastereomeres or as pharmacologically acceptable salts, solvates or hydrates. Examples for preferred salts and derivatives are alkali salts, i.e. sodium or potassium salts, sulfobenzoates, phosphates, isonicotinates, acetates, dichloroacetates, propionates, dihydrogenphosphates, palmitates, pivalates or furoates.

Examples of preferred PDE4-inhibtors which may be mentioned include Enprofylline, Theophylline, Roflumilaste, Ariflo (Cilomilaste), Tofimilaste, Pumafentrine, Lirimilaste, Apremilaste, Arofylline, Atizorame, Oglemilastum, Tetomilaste and 5-[(N-(2,5-dichloro-3-pyridinyl)-carboxamide]-8-methoxyquinoline 5-[N-(3,5-dichloro-1-oxido-4-pyridinyl)-carboxamide]-8-methoxy-2-(trifluoromethyl)-quinoline
N-(3,5-dichloropyrid-4-yl)-[1-(4-fluorobenzyl)-5-hydroxy-indole-3-yl]glyoxyl acid amide), 9-[(2-fluorophenyl)methyl]-N-methyl-2-(trifluoromethyl)-9H-purine-6-amine 4-[(2R)-2-[3-(cyclopentyloxy)-4-methoxyphenyl]-2-phenylethyl]-pyridine,
N-[(3R)-3,4,6,7-tetrahydro-9-methyl-4-oxo-1-phenylpyrrolo[3,2,1-jk][1,4]benzodiazepin-3-yl]-4-Pyridinecarboxamide,
4-[6,7-diethoxy-2,3-bis(hydroxymethyl)-1-naphthalenyl]-1-(2-methoxyethyl)-2(1H)-pyridinone
2-[4-[6,7-diethoxy-2,3-bis(hydroxymethyl)-1-naphthalenyl]-2-pyridinyl]-4-(3-pyridinyl)-1(2H)-Phthalazinone,
(3-(3-cyclopenyloxy-4-methoxybenzyl)-6-ethylamino-8-isopropyl-3H-purine,
beta-[3-(cyclopentyloxy)-4-methoxyphenyl]-1,3-dihydro-1,3-dioxo-2H-isoindole-2-propanamide,
9-ethyl-2-methoxy-7-methyl-5-propyl-imidazo[1,5-a]pyrido[3,2-e]pyrazin-6(5H)-one
5-[3-(cyclopentyloxy)-4-methoxyphenyl]-3-[(3-methylphenyl)methyl](3S,5S)-2-piperidinone,
4-[1-[3,4-bis(difluoromethoxy)phenyl]-2-(3-methyl-1-oxido-4-pyridinyl)ethyl]-alpha,alpha-bis(trifluoromethyl)-Benzenemethanol
N-(3,5-Dichloro-1-oxo-pyridine-4-yl)-4-difluoromethoxy-3-cyclopropylmethoxybenzamide
(−)p-[(4aR*,10bS*)-9-Ethoxy-1,2,3,4,4a,10b-hexahydro-8-methoxy-2-methylbenzo[s][1,6]naphthyridin-6-yl]-N,N-diisopropylbenzamide
(R)-(+)-1-(4-Bromobenzyl)-4-[(3-cyclopentyloxy)-4-methoxyphenyl]-2-pyrrolidone
3-(Cyclopentyloxy-4-methoxyphenyl)-1-(4-N'-[N-2-cyano-5-methyl-isothioureido]benzyl)-2-pyrrolidone
cis[4-Cyano-4-(3-cyclopentyloxy-4-methoxyphenyl)cyclohexan-1-carbon acid]
2-carbomethoxy-4-cyano-4-(3-cyclopropylmethoxy-4-difluoromethoxyphenyl)cyclohexan-1-one
cis[4-Cyano-4-(3-cyclopropylmethoxy-4-difluoromethoxyphenyl)cyclohexan-1-ol]
(R)-(+)-Ethyl[4-(3-cyclopentyloxy-4-methoxyphenyl)pyrrolidine-2-yliden]acetate
(S)-(−)-Ethyl[4-(3-cyclopentyloxy-4-methoxyphenyl)pyrrolidine-2-yliden]acetate
9-Cyclopentyl-5,6-dihydro-7-ethyl-3-(2-thienyl)-9H-pyrazolo[3,4-c]-1,2,4-triazolo[4,3-a]pyridine
9-Cyclopentyl-5,6-dihydro-7-ethyl-3-(tert-butyl)-9H-pyrazolo[3,4-c]-1,2,4-triazolo[4,3-a]pyridine
optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred EGFR-inhibitors which may be mentioned include Cetuximab, Trastuzumab, Panitumumab Gefitinib, Canertinib, Erlotinib, Mab ICR-62 and
4-[(3-Chlor-4-fluorphenyl)amino]-6-{[4-(morpholine-4-yl)-1-oxo-2-butene-1-yl]amino}-7-cyclopropylmethoxy-quinazoline
4-[(3-Chlor-4-fluorphenyl)amino]-6-{[4-(N,N-diethyl-lamino)-1-oxo-2-butene-1-yl]amino}-7-cyclopropyl-methoxy-quinazoline
4-[(3-Chlor-4-fluorphenyl)amino]-6-{[4-(N,N-dimethylamino)-1-oxo-2-butene-1-yl]amino}-7-cyclopropyl-methoxy-quinazoline
4-[(R)-(1-Phenyl-ethyl)amino]-6-{[4-(morpholine-4-yl)-1-oxo-2-butene-1-yl]amino}-7-cyclopentyloxy-quinazoline
4-[(3-Chlor-4-fluor-phenyl)amino]-6-{[4-((R)-6-methyl-2-oxo-morpholine-4-yl)-1-oxo-2-butene-1-yl]amino}-7-cyclopropylmethoxy-quinazoline
4-[(3-Chlor-4-fluor-phenyl)amino]-6-{[4-((R)-6-methyl-2-oxo-morpholine-4-yl)-1-oxo-2-butene-1-yl]amino}-7-[(S)-(tetrahydrofuran-3-yl)oxy]-quinazoline
4-[(3-Chlor-4-fluor-phenyl)amino]-6-{[4-((R)-2-methoxymethyl-6-oxo-morpholine-4-yl)-1-oxo-2-butene-1-yl]amino}-7-cyclopropylmethoxy-quinazoline
4-[(3-Chlor-4-fluor-phenyl)amino]-6-[2-((S)-6-methyl-2-oxo-morpholine-4-yl)-ethoxy]-7-methoxy-quinazoline
4-[(3-Chlor-4-fluorphenyl)amino]-6-({4-[N-(2-methoxy-ethyl)-N-methyl-amino]-1-oxo-2-butene-1-yl}amino)-7-cyclopropylmethoxy-quinazoline
4-[(3-Chlor-4-fluorphenyl)amino]-6-{[4-(N,N-dimethylamino)-1-oxo-2-butene-1-yl]amino}-7-cyclopentyloxy-quinazoline
4-[(R)-(1-Phenyl-ethyl)amino]-6-{[4-(N,N-bis-(2-methoxyethyl)-amino)-1-oxo-2-butene-1-yl]amino}-7-cyclopropylmethoxy-quinazoline
4-[(R)-(1-Phenyl-ethyl)amino]-6-({4-[N-(2-methoxyethyl)-N-ethyl-amino]-1-oxo-2-butene-1-yl}amino)-7-cyclopropylmethoxy-quinazoline
4-[(R)-(1-Phenyl-ethyl)amino]-6-({4-[N-(2-methoxyethyl)-N-methyl-amino]-1-oxo-2-butene-1-yl}amino)-7-cyclopropylmethoxy-quinazoline
4-[(R)-(1-Phenyl-ethyl)amino]-6-({4-[N-(tetrahydropyran-4-yl)-N-methyl-amino]-1-oxo-2-butene-1-yl}amino)-7-cyclopropylmethoxy-quinazoline
4-[(3-Chlor-4-fluorphenyl)amino]-6-{[4-(N,N-dimethylamino)-1-oxo-2-butene-1-yl]amino}-7-((R)-tetrahydrofuran-3-yloxy)-quinazoline
4-[(3-Chlor-4-fluorphenyl)amino]-6-{[4-(N,N-dimethylamino)-1-oxo-2-butene-1-yl]amino}-7-((S)-tetrahydrofuran-3-yloxy)-quinazoline
4-[(3-Chlor-4-fluorphenyl)amino]-6-({4-[N-(2-methoxyethyl)-N-methyl-amino]-1-oxo-2-butene-1-yl}amino)-7-cyclopentyloxy-quinazoline
4-[(3-Chlor-4-fluorphenyl)amino]-6-{[4-(N-cyclopropyl-N-methyl-amino)-1-oxo-2-butene-1-yl]amino}-7-cyclopentyloxy-quinazoline
4-[(3-Chlor-4-fluorphenyl)amino]-6-{[4-(N,N-dimethylamino)-1-oxo-2-butene-1-yl]amino}-7-[(R)-(tetrahydrofuran-2-yl)methoxy]-quinazoline
4-[(3-Chlor-4-fluorphenyl)amino]-6-{[4-(N,N-dimethylamino)-1-oxo-2-butene-1-yl]amino}-7-[(S)-(tetrahydrofuran-2-yl)methoxy]-quinazoline
4-[(3-Ethinyl-phenyl)amino]-6,7-bis-(2-methoxy-ethoxy)-quinazoline
4-[(3-Chlor-4-fluorphenyl)amino]-7-[3-(morpholine-4-yl)-propyloxy]-6-[(vinylcarbonyl)amino]-quinazoline
4-[(R)-(1-Phenyl-ethyl)amino]-6-(4-hydroxy-phenyl)-7H-pyrrolo[2,3-d]pyrimidine
3-Cyano-4-[(3-chlor-4-fluorphenyl)amino]-6-{[4-(N,N-dimethylamino)-1-oxo-2-butene-1-yl]amino}-7-ethoxy-quinoline
4-{[3-Chlor-4-(3-fluor-benzyloxy)-phenyl]amino}-6-(5-{[(2-methansulfonyl-ethyl)amino]methyl}-furan-2-yl)quinazoline
4-[(R)-(1-Phenyl-ethyl)amino]-6-{[4-((R)-6-methyl-2-oxo-morpholine-4-yl)-1-oxo-2-butene-1-yl]amino}-7-methoxy-quinazoline 4-[(3-Chlor-4-fluorphenyl)amino]-6-{[4-(morpholine-4-yl)-1-oxo-2-butene-1-yl]amino}-7-[(tetrahydrofuran-2-yl)methoxy]-quinazoline 4-[(3-Chlor-4-fluorphenyl)amino]-6-({4-[N,N-bis-(2-methoxy-ethyl)-amino]-1-oxo-2-butene-1-yl}amino)-7-[(tetrahydrofuran-2-yl)methoxy]-quinazoline 4-[(3-Ethinyl-phenyl)amino]-6-{[4-(5,5-dimethyl-2-oxo-morpholine-4-yl)-1-oxo-2-butene-1-yl]amino}-quinazoline 4-[(3-Chlor-4-fluor-phenyl)amino]-6-[2-(2,2-dimethyl-6-oxo-morpholine-4-yl)-ethoxy]-7-methoxy-quinazoline 4-[(3-Chlor-4-fluor-phenyl)amino]-6-[2-(2,2-dimethyl-6-oxo-morpholine-4-yl)-ethoxy]-7-[(R)-(tetrahydrofuran-2-yl)methoxy]-quinazoline 4-[(3-Chlor-4-fluor-phenyl)amino]-7-[2-(2,2-dimethyl-6-oxo-morpholine-4-yl)-ethoxy]-6-[(S)-(tetrahydrofuran-2-yl)methoxy]-quinazoline 4-[(3-Chlor-4-fluor-phenyl)amino]-6-{2-[4-(2-oxo-morpholine-4-yl)-piperidin-1-yl]-ethoxy}-7-methoxy-quinazoline 4-[(3-Chlor-4-fluor-phenyl)amino]-6-[1-(tert.-butyloxycarbonyl)-piperidine-4-yloxy]-7-methoxy-quinazoline 4-[(3-Chlor-4-fluor-phenyl)amino]-6-(trans-4-amino-cyclohexane-1-yloxy)-7-methoxy-quinazoline 4-[(3-Chlor-4-fluor-phenyl)amino]-6-(trans-4-methansulfonylamino-cyclohexane-1-yloxy)-7-methoxy-quinazoline 4-[(3-Chlor-4-fluor-phenyl)amino]-6-(tetrahydropyran-3-yloxy)-7-methoxy-quinazoline 4-[(3-Chlor-4-fluor-phenyl)amino]-6-(1-methyl-piperidine-4-yloxy)-7-methoxy-quinazoline 4-[(3-Chlor-4-fluor-phenyl)amino]-6-{1-[(morpholine-4-yl)carbonyl]-piperidine-4-yloxy}-7-methoxy-quinazoline 4-[(3-Chlor-4-fluor-phenyl)amino]-6-{1-[(methoxymethyl)carbonyl]-piperidine-4-yloxy}-7-methoxy-quinazoline 4-[(3-Chlor-4-fluor-phenyl)amino]-6-(piperidine-3-yloxy)-7-methoxy-quinazoline 4-[(3-Chlor-4-fluor-phenyl)amino]-6-[1-(2-acetylamino-ethyl)-piperidine-4-yloxy]-7-methoxy-quinazoline 4-[(3-Chlor-4-fluor-phenyl)amino]-6-(tetrahydropyran-4-yloxy)-7-ethoxy-quinazoline 4-[(3-Chlor-4-fluor-phenyl)amino]-6-((S)-tetrahydrofuran-3-yloxy)-7-hydroxy-quinazoline 4-[(3-Chlor-4-fluor-phenyl)amino]-6-(tetrahydropyran-4-yloxy)-7-(2-methoxy-ethoxy)-quinazoline 4-[(3-Chlor-4-fluor-phenyl)amino]-6-{trans-4-[(dimethylamino)sulfonylamino]-cyclohexane-1-yloxy}-7-methoxy-quinazoline 4-[(3-Chlor-4-fluor-phenyl)amino]-6-{trans-4-[(morpholine-4-yl)carbonylamino]-cyclohexane-1-yloxy}-7-methoxy-quinazoline 4-[(3-Chlor-4-fluor-phenyl)amino]-6-{trans-4-[(morpholine-4-yl)sulfonylamino]-cyclohexane-1-yloxy}-7-methoxy-quinazoline 4-[(3-Chlor-4-fluor-phenyl)amino]-6-(tetrahydropyran-4-yloxy)-7-(2-acetylamino-ethoxy)-quinazoline 4-[(3-Chlor-4-fluor-phenyl)amino]-6-(tetrahydropyran-4-yloxy)-7-(2-methansulfonylamino-ethoxy)-quinazoline 4-[(3-Chlor-4-fluor-phenyl)amino]-6-{1-[(piperidine-1-yl)carbonyl]-piperidine-4-yloxy}-7-methoxy-quinazoline 4-[(3-Chlor-4-fluor-phenyl)amino]-6-(1-aminocarbonylmethyl-piperidine-4-yloxy)-7-methoxy-quinazoline 4-[(3-Chlor-4-fluor-phenyl)amino]-6-(cis-4-{N-[(tetrahydropyran-4-yl)carbonyl]-N-methyl-amino}-cyclohexane-1-yloxy)-7-methoxy quinazoline 4-[(3-Chlor-4-fluor-phenyl)amino]-6-(cis-4-{N-[(morpholine-4-yl)carbonyl]-N-methyl-amino}-cyclohexane-1-yloxy)-7-methoxy-quinazoline 4-[(3-Chlor-4-fluor-phenyl)amino]-6-(cis-4-{N-[(morpholine-4-yl)sulfonyl]-N-methyl-amino}-cyclohexane-1-yloxy)-7-methoxy-quinazoline 4-[(3-Chlor-4-fluor-phenyl)amino]-6-(trans-4-ethansulfonylamino-cyclohexane-1-yloxy)-7-methoxy-quinazoline 4-[(3-Chlor-4-fluor-phenyl)amino]-6-(1-methansulfonyl-piperidine-4-yloxy)-7-ethoxy-quinazoline 4-[(3-Chlor-4-fluor-phenyl)amino]-6-(1-methansulfonyl-piperidine-4-yloxy)-7-(2-methoxy-ethoxy)-quinazoline 4-[(3-Chlor-4-fluor-phenyl)amino]-6-[1-(2-methoxy-acetyl)-piperidine-4-yloxy]-7-(2-methoxy-ethoxy)-quinazoline 4-[(3-Chlor-4-fluor-phenyl)amino]-6-(cis-4-acetylamino-cyclohexane-1-yloxy)-7-methoxy-quinazoline 4-[(3-Ethinyl-phenyl)amino]-6-[1-(tert-butyloxycarbonyl)-piperidine-4-yloxy]-7-methoxy-quinazoline 4-[(3-Ethinyl-phenyl)amino]-6-(tetrahydropyran-4-yloxy]-7-methoxy-quinazoline 4-[(3-Chlor-4-fluor-phenyl)amino]-6-(cis-4-{N-[(piperidine-1-yl)carbonyl]-N-methyl-amino}-cyclohexane-1-yloxy)-7-methoxy-quinazoline 4-[(3-Chlor-4-fluor-phenyl)amino]-6-(cis-4-{N-[(4-methyl-piperazine-1-yl)carbonyl]-N-methyl-amino}-cyclohexane-1-yloxy)-7-methoxy-quinazoline 4-[(3-Chlor-4-fluor-phenyl)amino]-6-{cis-4-[(morpholine-4-yl)carbonylamino]-cyclohexane-1-yloxy}-7-methoxy-quinazoline 4-[(3-Chlor-4-fluor-phenyl)amino]-6-{1-[2-(2-oxopyrrolidine-1-yl)ethyl]-piperidine-4-yloxy}-7-methoxy-quinazoline 4-[(3-Chlor-4-fluor-phenyl)amino]-6-{1-[(morpholine-4-yl)carbonyl]-piperidine-4-yloxy}-7-(2-methoxy-ethoxy)-quinazoline 4-[(3-Ethinyl-phenyl)amino]-6-(1-acetyl-piperidine-4-yloxy)-7-methoxy-quinazoline 4-[(3-Ethinyl-phenyl)amino]-6-(1-methyl-piperidine-4-yloxy)-7-methoxy-quinazoline 4-[(3-Ethinyl-phenyl)amino]-6-(1-methansulfonyl-piperidine-4-yloxy)-7-methoxy-quinazoline 4-[(3-Chlor-4-fluor-phenyl)amino]-6-(1-methyl-piperidine-4-yloxy)-7(2-methoxy-ethoxy)-quinazoline 4-[(3-Chlor-4-fluor-phenyl)amino]-6-(1-isopropyloxycarbonyl-piperidine-4-yloxy)-7-methoxy-quinazoline 4-[(3-Chlor-4-fluor-phenyl)amino]-6-(cis-4-methylamino-cyclohexane-1-yloxy)-7-methoxy-chinazoline 4-[(3-Chlor-4-fluor-phenyl)amino]-6-{cis-4-[N-(2-methoxy-acetyl)-N-methyl-amino]-cyclohexane-1-yloxy}-7-methoxy-quinazoline 4-[(3-Ethinyl-phenyl)amino]-6-(piperidine-4-yloxy)-7-methoxy-quinazoline 4-[(3-Ethinyl-phenyl)amino]-6-[1-(2-methoxy-acetyl)-piperidine-4-yloxy]-7-methoxy-quinazoline 4-[(3-Ethinyl-phenyl)amino]-6-{1-[(morpholine-4-yl)carbonyl]-piperidine-4-yloxy}-7-methoxy-quinazoline 4-[(3-Chlor-4-fluor-phenyl)amino]-6-{1-[(cis-2,6-dimethyl-morpholine-4-yl)carbonyl]-piperidine-4-yloxy}-7-methoxy-quinazoline 4-[(3-Chlor-4-fluor-phenyl)amino]-6-{1-[(2-methyl-morpholine-4-yl)carbonyl]-piperidine-4-yloxy}-7-methoxy-quinazoline 4-[(3-Chlor-4-fluor-phenyl)amino]-6-{1-[(S,S)-(2-oxa-5-aza-bicyclo[2.2.1]hept-5-yl)carbonyl]-piperidine-4-yloxy}-7-methoxy-quinazoline 4-[(3-Chlor-4-fluor-phenyl)amino]-6-{1-[(N-methyl-N-2-methoxyethyl-amino)carbonyl]-piperidine-4-yloxy}-7-methoxy-quinazoline 4-[(3-Chlor-4-fluor-phenyl)amino]-6-(1-ethyl-piperidine-4-yloxy)-7-methoxy-quinazoline 4-[(3-Chlor-4-fluor-phenyl)amino]-6-{1-[(2-methoxyethyl)carbonyl]-piperidine-4-yloxy}-7-methoxy-quinazoline 4-[(3-Chlor-4-fluor-phenyl)amino]-6-{1-[(3-methoxypropyl-amino)-carbonyl]-piperidine-4-yloxy}-7-methoxy-quinazoline 4-[(3-Chlor-4-fluor-phenyl)amino]-6-[cis-4-(N-methansulfonyl-N-methyl-amino)-cyclohexane-1-yloxy]-7-methoxy-quinazoline 4-[(3-Chlor-4-fluor-phenyl)amino]-6-[cis-4-(N-acetyl-N-methyl-amino)-cyclohexane-1-yloxy]-7-methoxy-quinazoline 4-[(3-Chlor-4-fluor-phenyl)amino]-6-(trans-4-methylamino-cyclohexane-1-yloxy)-7-methoxy-quinazoline 4-[(3-Chlor-4-fluor-phenyl)amino]-6-[trans-4-(N-methansulfonyl-N-methyl-amino)-cyclohexane-1-yloxy]-7-methoxy-quinazoline 4-[(3-Chlor-4-fluor-phenyl)amino]-6-(trans-4-dimethylamino-cyclohexane-1-yloxy)-7-methoxy-quinazoline 4-[(3-Chlor-4-fluor-phenyl)amino]-6-(trans-4-{N-[(morpholine-4-yl)carbonyl]-N-methyl-amino}-cyclohexane-1-yloxy)-7-methoxy-quinazoline 4-[(3-Chlor-4-fluor-phenyl)amino]-6-[2-(2,2-dimethyl-6-oxo-morpholine-4-yl)-ethoxy]-7-[(S)-(tetrahydrofuran-2-yl)methoxy]-quinazoline 4-[(3-Chlor-4-fluor-phenyl)amino]-6-(1-methansulfonyl-piperidine-4-yloxy)-7-methoxy-quinazoline 4-[(3-Chlor-4-fluor-phenyl)amino]-6-(1-cyano-piperidine-4-yloxy)-7-methoxy-quinazoline optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred SYK-inhibitors which may be mentioned include

2-[(2-aminoethyl)amino]-4-[(3-bromophenyl)amino]-5-pyrimidinecarboxamide;

2-[[7-(3,4-dimethoxyphenyl)imidazo[1,2-c]pyrimidine-5-yl]amino]-3-pyridinecarboxamide;

6-[[5-fluoro-2-[3,4,5-trimethoxyphenyl)amino]-4-pyrimidinyl]amino]-2,2-dimethyl-2H-pyrido[3,2-b]-1,4-oxazin-3(4H)-one;

N-[3-bromo-7-(4-methoxyphenyl)-1,6-naphthyridine-5-yl]-1,3-propanediamine;

7-(4-methoxyphenyl)-N-methyl-1,6-naphthyridine-5-amine;

N-[7-(4-methoxyphenyl)-1,6-naphthyridine-5-yl]-1,3-propanediamine;

N-[7-(2-thienyl)-1,6-naphthyridine-5-yl]-1,3-propanediamine;

N-[7-[4-(dimethylamino)phenyl]-1,6-naphthyridine-5-yl]-1,2-ethanediamine;

N-[7-(4-methoxyphenyl)-2-(trifluoromethyl)-1,6-naphthyridine-5-yl]-1,3-propanediamine;

N-[7-(4-methoxyphenyl)-3-phenyl-1,6-naphthyridine-5-yl]-1,3-propanediamine;

N-(7-phenyl-1,6-naphthyridine-5-yl)-1,3-propanediamine;

N-[7-(3-fluorophenyl)-1,6-naphthyridine-5-yl]-1,3-propanediamine;

N-[7-(3-chlorophenyl)-1,6-naphthyridine-5-yl]-1,3-propanediamine;

N-[7-[3-(trifluoromethoxy)phenyl]-1,6-naphthyridine-5-yl]-1,3-propanediamine;

N-[7-(4-fluorophenyl)-1,6-naphthyridine-5-yl]-1,3-propanediamine;

N-[7-(4-fluorophenyl)-1,6-naphthyridine-5-yl]-1,3-propanediamine;

N-[7-(4-chlorophenyl)-1,6-naphthyridine-5-yl]-1,3-propanediamine;

N-[7-(4'-methyl[1,1'-biphenyl]-4-yl]-1,6-naphthyridine-1,3-propanediamine;

N-[7-[4-(dimethylamino)phenyl]-1,6-naphthyridine-5-yl]-1,3-propanediamine;

N-[7-[4-(diethylamino)phenyl]-1,6-naphthyridine-5-yl]-1,3-propanediamine;

N-[7-[4-(4-morpholinyl)phenyl]-1,6-naphthyridine-5-yl]-1,3-propanediamine;

N-[7-[4-[[2-(dimethylamino)ethyl]methylamino]phenyl]-1,6-naphthyridine-5-yl]-1,3-propanediamine;

N-[7-(4-bromophenyl)-1,6-naphthyridine-5-yl]-1,3-propanediamine;

N-[7-(4-methylphenyl)-1,6-naphthyridine-5-yl]-1,3-propanediamine;

N-[7-[4-(methylthio)phenyl]-1,6-naphthyridine-5-yl]-1,3-propanediamine;

N-[7-[4-(1-methylethyl)phenyl]-1,6-naphthyridine-5-yl]-1,3-propanediamine;

7-[4-(dimethylamino)phenyl]-N-methyl-1,6-naphthyridine-5-amine;

7-[4-(dimethylamino)phenyl]-N,N-dimethyl-1,6-naphthyridine-5-amine;

N-[7-[4-(dimethylamino)phenyl]-1,6-naphthyridine-5-yl]-1,4-butanediamine;

N-[7-[4-(dimethylamino)phenyl]-1,6-naphthyridine-5-yl]-1,5-pentanediamine;

3-[[7-[4-(dimethylamino)phenyl]-1,6-naphthyridine-5-yl]oxy]-1-propanole;

4-[5-(4-aminobutoxy)-1,6-naphthyridine-7-yl]-N,N-dimethyl-benzenamine;

4-[[7-[4-(dimethylamino)phenyl]-1,6-naphthyridine-5-yl]amino]-1-butanole;

N-[7-[4-(dimethylamino)phenyl]-1,6-naphthyridine-5-yl]-N-methyl-1,3-propanediamine;

N-[7-[4-(dimethylamino)phenyl]-1,6-naphthyridine-5-yl]-N'-methyl-1,3-propanediamine;

N-[7-[4-(dimethylamino)phenyl]-1,6-naphthyridine-5-yl]-N,N'-dimethyl-1,3-propanediamine;

1-amino-3-[[7-[4-(dimethylamino)phenyl]-1,6-naphthyridine-5-yl]amino]-2-propanole;

N-[7-[4-(dimethylamino)phenyl]-1,6-naphthyridine-5-yl]-2,2-dimethyl-1,3-propanediamine;

7-[4-(dimethylamino)phenyl]-N-(3-pyridinylmethyl)-1,6-naphthyridine-5-amine;

N-[(2-aminophenyl)methyl]-7-[4-(dimethylamino)phenyl]-1,6-naphthyridine-5-amine;

N-[7-[6-(dimethylamino)[1,1'-biphenyl]-3-yl]-1,6-naphthyridine-5-yl]-1,3-propanediamine;

N-[7-[3-chloro-4-(diethylamino)phenyl]-1,6-naphthyridine-5-yl]-1,3-propanediamine;

N-[7-[4-(dimethylamino)-3-methoxyphenyl]-1,6-naphthyridine-5-yl]-1,3-propanediamine;

N-[7-[4-(diethylamino)phenyl]-3-methyl-1,6-naphthyridine-5-yl]-1,3-propanediamine;

N-[7-(3'-fluoro[1,1'-biphenyl]-3-yl)-1,6-naphthyridine-5-yl]-1,2-ethanediamin,

N-[7-(4-methoxyphenyl)-1,6-naphthyridine-5-yl]-1,6-naphthyridine-1,3-propanediamine;

N,N'-bis(3-aminopropyl)-7-(4-methoxyphenyl)-2,5-diamine;
N-[7-(4-methoxyphenyl)-2-(phenylmethoxy)-1,6-naphthyridine-5-yl]-1,6-naphthyridine-1,3-propanediamine;
N5-(3-aminopropyl)-7-(4-methoxyphenyl)-N-2-(phenylmethyl)-2,5-diamine;
N-[7-(2-naphthalenyl)-1,6-naphthyridine-5-yl]-1,3-propanediamine;
N-[7-(2'-fluoro[1,1'-biphenyl]-4-yl)-1,6-naphthyridine-5-yl]-1,3-propanediamine;
N-[7-(3,4,5-trimethoxyphenyl)-1,6-naphthyridine-5-yl]-1,3-propanediamine;
N-[7-(3,4-dimethylphenyl)-1,6-naphthyridine-5-yl]-1,3-propanediamine;
1-amino-3-[[7-(2-naphthalenyl)-1,6-naphthyridine-5-yl]amino]-2-propanole;
1-amino-3-[[7-(2'-fluoro[1,1'-biphenyl]-4-yl)-1,6-naphthyridine-5-yl]amino]-2-propanole;
1-amino-3-[[7-(4'-methoxy[1,1'-biphenyl]-4-yl)-1,6-naphthyridine-5-yl]amino]-2-propanole;
1-amino-3-[[7-(3,4,5-trimethoxyphenyl)-1,6-naphthyridine-5-yl]amino]-2-propanole;
1-amino-3-[[7-(4-bromophenyl)-1,6-naphthyridine-5-yl]amino]-2-propanole;
N-[7-(4'-methoxy[1,1'-biphenyl]-4-yl)-1,6-naphthyridine-5-yl]-2,2-dimethyl-1,3-propanediamine;
1-[[7-[4-(dimethylamino)phenyl]-1,6-naphthyridine-5-yl]amino]-2-propanole;
2-[[2-[[7-[4-(dimethylamino)phenyl]-1,6-naphthyridine-5-yl]amino]ethyl]thio]-ethanole;
7-[4-(dimethylamino)phenyl]-N-(3-methyl-5-isoxazolyl)-1,6-naphthyridine-5-amine;
7-[4-(dimethylamino)phenyl]-N-4-pyrimidinyl-1,6-naphthyridine-5-amine;
N-[7-[4-(dimethylamino)phenyl]-1,6-naphthyridine-5-yl]-1,3-cyclohexane diamine;
N,N-dimethyl-4-[5-(1-piperazinyl)-1,6-naphthyridine-7-yl]-benzenamine;
4-[5-(2-methoxyethoxy)-1,6-naphthyridine-7-yl]-N,N-dimethyl-benzenamine;
1-[7-[4-(dimethylamino)phenyl]-1,6-naphthyridine-5-yl]-4-piperidinole;
1-[7-[4-(dimethylamino)phenyl]-1,6-naphthyridine-5-yl]-3-pyrrolidinole;
7-[4-(dimethylamino)phenyl]-N-(2-furanylmethyl)-1,6-naphthyridine-5-amine;
7-[4-(dimethylamino)phenyl]-N-[3-(1H-imidazole-1-yl)propyl]-1,6-naphthyridine-5-amine;
1-[7-[4-(dimethylamino)phenyl]-1,6-naphthyridine-5-yl]-4-piperidine carboxamide;
1-[3-[[7-[4-(dimethylamino)phenyl]-1,6-naphthyridine-5-yl]amino]propyl]-2-pyrrolidinone;
N-[3'-[5-[(3-aminopropyl)amino]-1,6-naphthyridine-7-yl][1,1'-biphenyl]-3-yl]-acetamide;
N-[7-(4'-fluoro[1,1'-biphenyl]-4-yl)-1,6-naphthyridine-5-yl]-1,3-propanediamine;
N-[4'-[5-[(3-aminopropyl)amino]-1,6-naphthyridine-7-yl][1,1'-biphenyl]-3-yl]-acetamide;
N-[7-[4-(1,3-benzodioxol-5-yl)phenyl]-1,6-naphthyridine-5-yl]-1,3-propanediamine;
N-[7-[4-(2-thienyl)phenyl]-1,6-naphthyridine-5-yl]-1,3-propanediamine;
N-[7-[4-fluoro-3-(trifluoromethyl)phenyl]-1,6-naphthyridine-5-yl]-1,3-propanediamine;
N-[7-[4-(3-pyridinyl)phenyl]-1,6-naphthyridine-5-yl]-1,3-propanediamine;
N-[7-(1,3-benzodioxol-5-yl)-1,6-naphthyridine-5-yl]-1,3-propanediamine;
N-[7-(6-methoxy-2-naphthalenyl)-1,6-naphthyridine-5-yl]-1,3-propanediamine;
7-[4-(dimethylamino)phenyl]-N-(4-pyridinylmethyl)-1,6-naphthyridine-5-amine;
3-[[7-[4-(dimethylamino)phenyl]-1,6-naphthyridine-5-yl]methylamino]-propanenitrile;
7-[4-(dimethylamino)phenyl]-N-[1-(phenylmethyl)-4-piperidinyl]-1,6-naphthyridine-5-amine;
N-[7-[4-(dimethylamino)phenyl]-1,6-naphthyridine-5-yl]-1,2-cyclohexanediamin,
N-[7-[4-(dimethylamino)phenyl]-1,6-naphthyridine-5-yl]-1,2-Cyclohexanediamine, (1R,2S)-rel-.
N-[7-[4-(dimethylamino)phenyl]-1,6-naphthyridine-5-yl]-1,2-benzene dimethanamine;
N-[7-[4-(diethylamino)phenyl]-1,6-naphthyridine-5-yl]-1,4-butanediamine;
N-[7-[3',5'-bis(trifluoromethyl)[1,1'-biphenyl]-4-yl]-1,6-naphthyridine-5-yl]-,3-propanediamine;
N-[7-(3'-methoxy[1,1'-biphenyl]-4-yl)-1,6-naphthyridine-5-yl]-1,3-propanediamine;
N-[7-(3'-fluoro[1,1'-biphenyl]-4-yl)-1,6-naphthyridine-5-yl]-1,3-propanediamine;
4-[[7-[4-(dimethylamino)phenyl]-1,6-naphthyridine-5-yl]oxy]-1-butanole;
N-[7-[4-(dimethylamino)phenyl]-1,6-naphthyridine-5-yl]-1,4-cyclohexanediamine;
7-[4-(dimethylamino)phenyl]-N-(2,2,6,6-tetramethyl-4-piperidinyl)-1,6-naphthyridine-5-amine;
N-[7-[3-bromo-4-(dimethylamino)phenyl]-1,6-naphthyridine-5-yl]-1,3-propanediamine;
N-[7-(1-methyl-1H-indole-5-yl)-1,6-naphthyridine-5-yl]-1,3-propanediamine;
N-[7-[3-(trifluoromethyl)phenyl]-1,6-naphthyridine-5-yl]-1,3-propanediamine;
N-[7-[4-(trifluoromethyl)phenyl]-1,6-naphthyridine-5-yl]-1,3-propanediamine;
N-[7-(3-bromo-4-methoxyphenyl)-1,6-naphthyridine-5-yl]-1,3-propanediamine;
N-[7-[4-[[3-(dimethylamino)propyl]methylamino]phenyl]-1,6-naphthyridine-5-yl]-1,4-cyclohexanediamine;
N-[7-[4-[[2-(dimethylamino)ethyl]methylamino]phenyl]-1,6-naphthyridine-5-yl]-1,4-cyclohexanediamine;
N-[7-[4-(dimethylamino)-3-methoxyphenyl]-1,6-naphthyridine-5-yl]-1,4-cyclohexanediamine;
N-[7-[4-(4-morpholinyl)phenyl]-1,6-naphthyridine-5-yl]-1,4-cyclohexanediamine;
N-[7-[3-bromo-4-(4-morpholinyl)phenyl]-1,6-naphthyridine-5-yl]-1,4-cyclohexanediamine;
4-[[7-[4-[[2-(dimethylamino)ethyl]methylamino]phenyl]-1,6-naphthyridine-5-yl]oxy]-cyclohexanole;
N-[7-[3-bromo-4-(4-morpholinyl)phenyl]-1,6-naphthyridine-5-yl]-1,3-propanediamine;
N,N-dimethyl-4-[5-(4-methyl-1-piperazinyl)-1,6-naphthyridine-7-yl]-benzenamine;
4-[[7-[4-[[3-(dimethylamino)propyl]methylamino]phenyl]-1,6-naphthyridine-5-yl]oxy]-cyclohexanole;
N-[7-[4-[[2-(dimethylamino)ethyl]methylamino]phenyl]-1,6-naphthyridine-5-yl]-1,4-butanediamin;
[3-[[5-[(3-aminopropyl)amino]-7-(4-methoxyphenyl)-1,6-naphthyridine-2-yl]amino]propyl]-carbamic acid-1,1-dimethylethyl ester, optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred antiallergic agents which may be mentioned include Epinastine, Cetirizine, Azelastine, Fexofenadine, Levocabastine, Loratadine, Mizolastine, Ketotifene, Emedastine, Dimetindene, Clemastine, Bamipine, Cexchlorpheniramine, Pheniramine, Doxylamine, Chlorphenoxamine, Dimenhydrinate, Diphenhydramine, Promethazine, Ebastine, Olopatadine, Desloratidine and Meclozine, optionally in racemic form, as enantiomers, diastereomeres or as pharmacologically acceptable salts, solvates or hydrates.

Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred MAP kinase inhibitors which may be mentioned include
Bentamapimod (AS-602801)
Doramapimod (BIRB-796),
5-Carbamoylindole (SD-169),
6-[(aminocarbonyl)(2,6-difluorophenyl)amino]-2-(2,4-difluorophenyl)-3-pyridine carboxamide (VX-702),
alpha-[2-[[2-(3-pyridinyl)ethyl]amino]-4-pyrimidinyl]-2-benzothiazole acetonitrile (AS-601245),
9,12-Epoxy-1H-diindolo[1,2,3-fg:3',2',1'-kl]pyrrolo[3,4-i][1,6]benzodiazocine-10-Carboxylic acid (CEP-1347),
4-[3-(4-chlorophenyl)-5-(1-methyl-4-piperidinyl)-1H-pyrazole-4-yl]-pyrimidine (SC-409),
optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Indications

The present invention is directed to compounds of general formula 1 which are useful in the prevention and/or treatment of a disease and/or condition wherein the activity of CXCR2 antagonism is of therapeutic benefit, including but not limited to the treatment and/or prevention of inflammatory diseases. Examples include respiratory or gastrointestinal diseases or complaints, inflammatory diseases of the joints, skin, or eyes, cancers and also diseases of the peripheral or central nervous system.

The compounds of general formula 1 are useful for the prevention and/or treatment of diseases of the airways and of the lung which are accompanied by increased mucus production, inflammations, and/or obstructive diseases of the airways. Examples include acute, allergic, or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyper-reactive airways, infections, bronchitis, pneumonitis, paediatric asthma, bronchiectases, pulmonary fibrosis, ARDS (acute adult respiratory distress syndrome), bronchial edema, pulmonary edema, bronchitis, pneumonia or interstitial pneumonia triggered by various causes, such as aspiration, inhalation of toxic gases, or bronchitis, pneumonia or interstitial pneumonia or interstitial pneumonia as a result of heart failure, irradiation, chemotherapy, cystic fibrosis, or mucoviscidosis, or alpha1-antitrypsin deficiency.

Accordingly, the present invention relates to a compound of general formula 1 as a medicament.

Furthermore, the present invention relates to the use of a compound of general formula 1 for the treatment and/or prevention of a disease and/or condition wherein the activity of CXCR2 antagonism is of therapeutic benefit.

Furthermore, the present invention relates to the use of a compound of general formula 1 for the treatment and/or prevention of inflammatory diseases. Examples include respiratory or gastrointestinal diseases or complaints, inflammatory diseases of the joints, skin, or eyes, cancers and also diseases of the peripheral or central nervous system.

Furthermore, the present invention relates to the use of a compound of general formula 1 for the treatment and/or prevention of diseases of the airways and of the lung which are accompanied by increased mucus production, inflammations, and/or obstructive diseases of the airways. Examples include acute, allergic, or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyper-reactive airways, infections bronchitis or pneumonitis, paediatric asthma, bronchiectases, pulmonary fibrosis, ARDS (acute adult respiratory distress syndrome), bronchial edema, pulmonary edema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis, or mucoviscidosis, or alpha1-antitrypsin deficiency.

In a further aspect of the present invention the present invention relates to methods for the treatment or prevention of above mentioned diseases and conditions, which method comprises the administration of an effective amount of a compound of general formula 1 to a human being.

The dose range of the compounds of general formula 1 applicable per day is usually from 0.1 mg to 500 mg, preferably from 1 mg to 50 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Formulations

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised in that they contain one or more compounds of formula I according to the preferred embodiments above.

It is particularly preferable if the compounds of formula I are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula I are administered by inhalation, particularly preferably if they are administered once or twice a day. For this purpose, the compounds of formula I have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also include concentrates or sterile ready-to-use inhalable solutions. The preparations which may be used according to the invention are described in more detail in the next part of the specification.

Inhalable Powders

If the active substances of formula I are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula I according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a pteridine and one or more combination partners selected from those described above.

What we claim:

1. A compound of the formula 1,

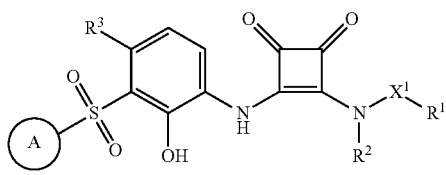

wherein
$R^1$ is selected from the group consisting of phenyl and furanyl, optionally substituted by one or two residues selected from halogen or $C_{1-6}$-alkyl, optionally substituted with one or more F atoms;
$X^1$ is absent or methylene optionally substituted with $C_{1-5}$-alkyl, said alkyl optionally substituted with one or more F atoms, $C_{1-4}$-alkyl-O—, CN or $C_{3-8}$-cycloalkyl, wherein optionally one carbon atom is replaced by an O;
$R^2$ is H;
$R^3$ is H, halogen, CN, $C_{1-6}$-alkyl, optionally substituted with one or more F atoms;
A is a N-linked 7-13 membered non-aromatic bicyclic system in which the two rings are either condensed to each other or joined in a spiro system and in which if present one CH group can be optionally replaced by N and one, two three or four $CH_2$ groups in said system are optionally replaced by NH, CO, O, S, SO, $SO_2$, and one, two three or four positions on said ring system are optionally substituted with one or more F atoms, $C_{1-6}$-alkyl, optionally substituted with one or more F atoms, $C_{1-6}$-alkyl-OC(O)—, HO—$C_{1-6}$-alkyl or $C_{1-6}$-alkyl-O—$C_{1-6}$-alkyl- and in which optionally two of these substituents are joined to form an additional ring
or a pharmaceutically acceptable salt thereof.

2. A compound of the formula 1, according to claim 1, wherein
$R^2$ is H;
$R^3$ is H, halogen, CN, $C_{1-6}$-alkyl, optionally substituted with one or more F atoms;
A is a N-linked four-, five- or six membered non-aromatic ring, with an additional condensed or spiro attached four-, five- or six membered ring, forming a bicyclic heterocyclic ring system, wherein
if present one CH group is optionally replaced by N; and one, two or three $CH_2$ groups are optionally replaced by NH, CO, O or $SO_2$ and one, two or three positions on said ring system are optionally substituted with $C_{1-6}$alkyl-OC(O)— or one or more $C_{1-6}$alkyl or HO—$C_{1-6}$alkyl;
or a pharmaceutically acceptable salt thereof.

3. A compound of the formula I, according to claim 1, wherein
$R^1$ is selected from the group consisting of phenyl and furanyl, optionally substituted by one or two residues selected from halogen or $C_{1-4}$-alkyl, optionally substituted with one or more F atoms;
$R^2$ is H;
$R^3$ is H, halogen, CN, $C_{1-4}$-alkyl, optionally substituted with one or more F atoms;
A is a N-linked four-, five- or six membered non-aromatic ring, with an additional condensed or spiro attached four-, five- or six membered ring, forming a bicyclic heterocyclic ring system, wherein
if present one CH group is optionally replaced by N; and one, two or three $CH_2$ groups are optionally replaced by NH, CO, O or $SO_2$ and one, two or three positions on said ring system are optionally substituted with $C_{1-6}$alkyl-OC(O)— or one or more $C_{1-6}$alkyl or HO—$C_{1-6}$alkyl;
or a pharmaceutically acceptable salt thereof.

4. A compound of the formula 1, according to claim 1, wherein
$R^1$ is selected from the group consisting of phenyl and furanyl, optionally substituted by one or two residues selected from Me, $CF_3$, F, Cl;
$R^2$ is H;
$R^3$ is H, Cl, CN, $CF_3$;
A is a bicyclic heterocyclic system of the formula -continued

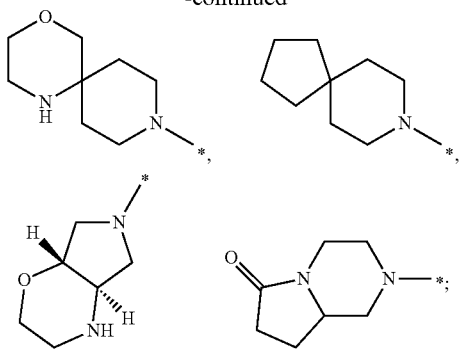

or a pharmaceutically acceptable salt thereof.

5. A compound of the formula 1, according to claim 1, wherein
$R^1$ is selected from the group consisting of phenyl and furanyl, optionally substituted by one or two residues selected from Me, $CF_3$, F, Cl;
$R^2$ is H;
$R^3$ is H, Cl, CN, $CF_3$;

A is a bicyclic heterocyclic system of the formula

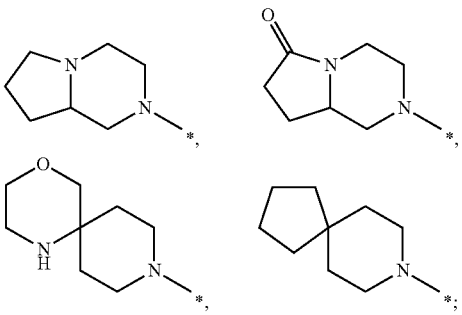

or a pharmaceutically acceptable salt thereof.

6. A pharmaceutical composition comprising a compound of the formula 1, according to claim 1, or a pharmaceutically acceptable salt thereof, and a pharmaceutically acceptable carrier.

* * * * *